US011986659B2

(12) United States Patent
Ahmed

(10) Patent No.: US 11,986,659 B2
(45) Date of Patent: May 21, 2024

(54) MODULATION OF NEURONAL NKCC1 AS A THERAPEUTIC STRATEGY FOR SPASTICITY AND RELATED DISORDERS

(71) Applicant: Research Foundation of the City University of New York, New York, NY (US)

(72) Inventor: Zaghloul Ahmed, Staten Island, NY (US)

(73) Assignee: Research Foundation of the City University of New York, New York, NY (US)

( * ) Notice: Subject to any disclaimer, the term of this patent is extended or adjusted under 35 U.S.C. 154(b) by 362 days.

(21) Appl. No.: 17/040,373

(22) PCT Filed: Mar. 22, 2019

(86) PCT No.: PCT/US2019/023675
§ 371 (c)(1),
(2) Date: Sep. 22, 2020

(87) PCT Pub. No.: WO2019/183536
PCT Pub. Date: Sep. 26, 2019

(65) Prior Publication Data
US 2021/0060341 A1 Mar. 4, 2021

Related U.S. Application Data

(60) Provisional application No. 62/646,574, filed on Mar. 22, 2018.

(51) Int. Cl.
*A61N 1/36* (2006.01)
*A61K 31/196* (2006.01)
(Continued)

(52) U.S. Cl.
CPC ........ *A61N 1/36121* (2013.01); *A61K 31/196* (2013.01); *A61K 45/06* (2013.01);
(Continued)

(58) Field of Classification Search
CPC ...... A61N 1/0529; A61N 1/0551; A61N 1/20; A61N 1/205; A61N 1/24; A61N 1/36062; A61N 1/36121; A61N 1/36157
(Continued)

(56) References Cited

U.S. PATENT DOCUMENTS 4,919,140 A 4/1990 Borgens et al.
8,380,304 B2 2/2013 Lozano
(Continued)

FOREIGN PATENT DOCUMENTS

EP 3581239 5/2021
WO WO2006053186 5/2006
(Continued)

OTHER PUBLICATIONS

ISA/US; International Search Report/Written Opinion for PCT/US2016/018167 dated May 2, 2016.
(Continued)

*Primary Examiner* — Carl H Layno
*Assistant Examiner* — Jane C Kalinock
(74) *Attorney, Agent, or Firm* — Peter J. Mikesell; Schmeiser, Olsen & Watts, LLP

(57) ABSTRACT

Methods, devices, and systems for treating spasticity, hypertonia or dystonia are disclosed. Treatment involves applying a source of direct current to one or more locations in a subject (animal, human, or other sentient being). Locations for application of direct current include the spinal column, peripheral nerves, and the cranium. The delivery of direct
(Continued)

current is adjusted to change biological activity of or level of gene expression and/or protein expression of target molecule NKCC1.

8 Claims, 25 Drawing Sheets

(51) Int. Cl.
    *A61K 45/06*     (2006.01)
    *A61N 1/05*     (2006.01)
    *A61N 1/20*     (2006.01)
    *A61N 1/24*     (2006.01)
    *A61P 25/14*     (2006.01)

(52) U.S. Cl.
    CPC ......... *A61N 1/0529* (2013.01); *A61N 1/0551* (2013.01); *A61N 1/20* (2013.01); *A61N 1/24* (2013.01); *A61N 1/36062* (2017.08); *A61N 1/36157* (2013.01); *A61P 25/14* (2018.01)

(58) Field of Classification Search
    USPC .......................................................... 607/3
    See application file for complete search history.

(56) References Cited

U.S. PATENT DOCUMENTS

| | | | |
|---|---|---|---|
| 9,283,391 | B2 | 3/2016 | Ahmed |
| 11,331,424 | B2* | 5/2022 | Imran ............... A61M 5/14276 |
| 2005/0119712 | A1 | 6/2005 | Shafer |
| 2005/0267103 | A1 | 12/2005 | Hochman |
| 2010/0274305 | A1 | 10/2010 | Gliner et al. |
| 2013/0035745 | A1 | 2/2013 | Ahmed et al. |
| 2013/0053922 | A1 | 2/2013 | Ahmed et al. |
| 2013/0090542 | A1 | 4/2013 | Kipke et al. |
| 2014/0017214 | A1 | 1/2014 | Cost |
| 2014/0148872 | A1 | 5/2014 | Goldwasser et al. |
| 2014/0249601 | A1 | 9/2014 | Bachinski et al. |
| 2014/0302007 | A1 | 10/2014 | Blanda et al. |
| 2015/0196767 | A1* | 7/2015 | Ahmed ............... A61N 1/36062 607/117 |
| 2015/0239832 | A1 | 8/2015 | Hochman et al. |
| 2017/0312505 | A1 | 11/2017 | Ahmed |
| 2018/0071525 | A1 | 3/2018 | Ahmed |
| 2020/0101291 | A1* | 4/2020 | Yakovlev ............... A61N 2/006 |
| 2021/0128920 | A1 | 5/2021 | Grill et al. |

FOREIGN PATENT DOCUMENTS

| | | |
|---|---|---|
| WO | WO2006110187 | 10/2006 |
| WO | WO2012018635 | 2/2012 |
| WO | WO2014039454 | 3/2014 |
| WO | WO2015095880 | 6/2015 |
| WO | WO2016133960 | 8/2016 |
| WO | WO2016209997 | 12/2016 |
| WO | WO2019183536 | 9/2019 |

OTHER PUBLICATIONS

EPO; European Supplementary Partial Search Report dated Jan. 17, 2022 for related European Application 19772271.3.
Ahmed, Z.; Trans-Spinal Direct Current Stimulation Alters Muscle Tone in Mice with and without Spinal Cord Injury with Spasticity; the Journal of Neuroscience; Jan. 29, 2014; pp. 1701-1709; 34(5).
Gifondorwa, D. et al.; Exogenous Delivery of Heat Shock Protein 70 Increases Lifespan in a Mouse Model of Amyotrophic Lateral Sclerosis; the Journal of Neuroscience; Nov. 28, 2007; pp. 13173-13180; 27(48).
Robinson, M. et al.; Extracellular Heat Shock Protein 70: A Critical Component for Motoneuron Survival; the Journal of Neuroscience; Oct. 19, 2005; pp. 9735-9745; 25(42).
Keuters, M. et al.; Transcranial direct current stimulation promotes the mobility of engrafted NSCs in the rat brain; NBR in Biomedicine; Dec. 17, 2014; pp. 231-239; vol. 28.
McKenzie, I. et al.; Motor skill learning requires active central myelination; Research; Oct. 17, 2014; pp. 318-322; vol. 346, Issue 6207.
ISA/US; International Search Report/Written Opinion dated Jul. 17, 2019 for corresponding International Application PCT/US19/23675 filed Mar. 22, 2019.
Hsieh, P. et al; Effect of acetazolamide for long-lasting paroxysmal dystonia in a patient with multiple sclerosis: a case report and review of literature; Neuropsychiatric Disease and Treatment; Apr. 3, 2013; pp. 445-448; vol. 9.
Brashear, A.; Botulinum toxin type A in the treatment of patients with cervical dystonia; Biologics: Targets & Therapy; Jul. 13, 2009; pp. 1-7; vol. 3.
ISA/US; International Search Report/Written Opinion for related International Application PCT/US2022/030655 dated Sep. 2, 2022.
EPO; Extended European Search Report dated Nov. 4, 2022 in related European Application 19772271.3.

\* cited by examiner

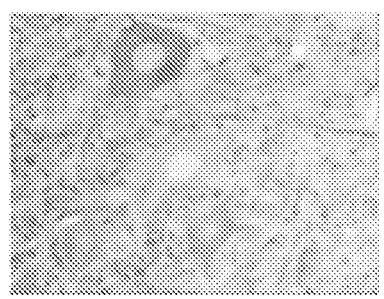 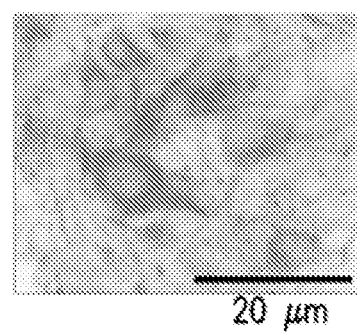
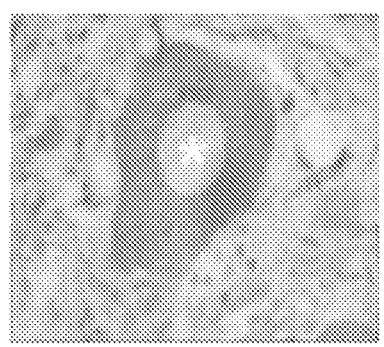 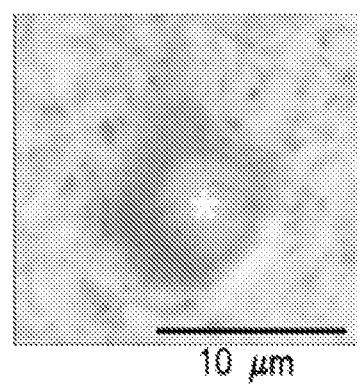
FIG.8A  FIG.8B
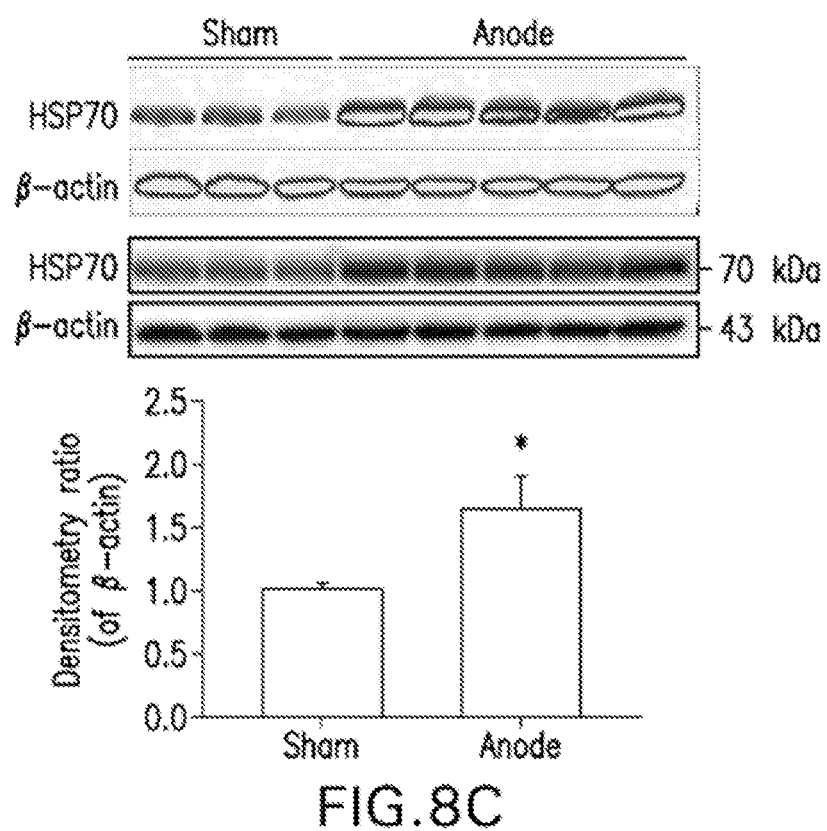
FIG.8C

MODULATION OF NEURONAL NKCC1 AS A THERAPEUTIC STRATEGY FOR SPASTICITY AND RELATED DISORDERS

CROSS-REFERENCE TO RELATED APPLICATIONS

This application claims priority to 62/646,574 filed Mar. 22, 2018, which is incorporated herein by reference for all purposes.

FIELD

The present invention relates to methods and systems for treating spasticity, hypertonia or dystonia.

BACKGROUND

Spinal hyperexcitability is highly prevalent following spinal cord injury (SCI) and is problematic in at least one-third of patients (Holtz et al., 2017). Spinal hyperexcitability is also present in a variety of neurological conditions and disorders. Spasticity is a form of involuntary contraction of muscles following sensory input induced by muscle stretch and it has been characterized as a velocity-dependent phenomenon (Lance, 1990) due to the primary endings that are highly sensitive to the velocity of stretch (Brown and Matthews, 1966). Velocity-dependent spasticity also develops in rats (Bennett et al., 1999; Bose et al. 2002; Vlarsala et al., 2005) and mice (Ahmed, 2014) following SCI. Due to its characteristics, spasticity negatively interferes with functional movements (Knutsson and Richards, 1979; Lamontagne et al., 2001). Spasticity can cause pain and fatigue, sleep disturbances, it can restrict daily activities such as walking, sitting and bathing, and it can complicate rehabilitation efforts. Thus, spasticity negatively influences an individual's quality of life and novel therapeutic interventions are needed.

SUMMARY

In one or more embodiments, the present invention is directed to methods, devices and systems for treating spasticity, hypertonia or dystonia by applying a source of direct current to one or more locations in animals, including humans and other sentient beings. The locations for application of direct current include the spinal column, peripheral nerves and the cranium.

A permanent reduction in spasticity was associated with an increase in rate-dependent depression of spinal reflexes, and ground and skill locomotion were improved, following anodal trans-spinal direct current stimulation (tsDCS). It is shown herein that neuronal Na—K—Cl cotransporter isoform 1 (NKCC1) is significantly up-regulated in mice that exhibit spasticity following induced SCI. When mice were treated with anodal tsDCS, down regulation of NKCC1 was detected, and this down regulation was to a level that did not significantly differ from that in non-injured control mice. Thus, in one or more embodiments, the present invention is directed to at least the long lasting reduction of spasticity by down-regulation of NKCC1 and/or inhibition of NKCC1 activity via the methods, systems and devices disclosed herein.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In addition, the materials, methods, and examples are illustrative only and not intended to be limiting.

Where applicable or not specifically disclaimed, any one of the embodiments described herein are contemplated to be able to combine with any other one or more embodiments, even though the embodiments are described under different aspects of the disclosure.

These and other embodiments are disclosed and/or encompassed by, the following detailed description.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A (left) depicts a stretch apparatus constructed from a stepper motor, movement arm, isometric force transducer, and mouse restrainer. The system was controlled by computer software. FIG. 1A (right) shows how a limb would be positioned in the mouse holder. FIG. 1B is a representative example of the muscle resistance traces recorded at: Speed 1=18 deg/s; Speed 2=180 deg/s; and Speed 3=1800 deg/s. The trace on the left is from an animal that was awake, while the trace on the right was obtained with an animal that was asleep due to isoflurane administration. FIG. 1C, the bottom two traces represent raw and root squared EMG. * denotes EMG during deep anesthesia. FIG. 1D shows force traces recorded for awake and asleep mice at Speed 1 are superimposed to show the effect of isoflurane on measured active resistance, rising slope, and peak.

FIG. 3A represents a general setup of the DigiGait system. Locomotion was tested at two speeds: 10 cm/s and 20 cm/s. A typical recording is shown at the top right, with corresponding rising slope, peak paw area, and falling slope data labeled. The bottom recordings represent the stance phases from representative animals from each group. FIG. 3B shows how control healthy animals were evaluated twice with a two week interval in between testing. The gray bars represent left hind limb (LHL) data and the blue bars represent right hind limb (RHL) data. E1, E2: see Methods. The control animals exhibited no difference in paw area, rising slope, or falling slope between E1 and E2 for either limb. FIG. 3C shows how sham-treated animals exhibited significant decreases in paw area for the LHL during E1-E3 at slow speed (p=0.009). Paw area did not decrease for the RHL. At the faster speed paw area for the LHL significantly decreased during E1-E3 (p=0.005), yet it did not significantly change for the RHL. Rising slope significantly decreased during E1 at the slow speed for the LHL (p=0.039), and not for the RHL. At the faster speed, rising slope did not change significantly for either hind limb. Falling slope did not significantly decrease for either hind limb at slow speed. Meanwhile, at the faster speed, falling slope significantly decreased during E1-E3 for the LHL (p=0.012), and not for the RHL. *p<0.05, Holm-Sidak method. FIG. 3D shows how anodal tsDCS-treated animals exhibited a significant increase in paw area during E1-E3 at the slow speed for the LHL, while only during E1 and E2 for the RHL (p<0.001 for both hind limbs). Paw area significantly increased during E1 at the faster speed for both the LHL and the RHL (each p<0.001). Rising slope significantly increased at the slow speed during E1 and E2 for the RHL (p=0_002), yet did not increase for the LHL. Rising slope significantly increased during E1 at the faster speed only for the RHL (p=0.011). Falling slope significantly increased during E1 and E2 at the slow speed for the LHL and the RHL (each p<0.001). Falling slope significantly increased during E1 at the faster speed only for the RHL (p<0.001). *p<0.05, Holm-Sidak method. Last, FIG. 3E depicts how cathodal tsDCS-treated animals exhibited a significant increase in paw area during E1 at the slow speed compared to baseline (LHL: p<0.001; RHL: p<0.001), yet did not during E2 or E3. No significant change in paw area was observed at E1-E3 at the faster speed. Rising slope also remained unchanged at both speeds. Falling slope significantly increased during E1 and E2 for the LHL (p<0.001), and only during E1 for the RHL (p=0.025). *p<0.05, Holm-Sidak method. There was no significant change in falling slope at the faster speed. Data are presented as mean±SEM.

FIG. 4B depicts bar graphs which show the mean scores of skilled locomotion for the four time points evaluated (see Methods). Sham, SCI group that was sham-treated; Anode, SCI group that was treated daily for 7 d with anode tsDCS: Cathode, SCI group that was treated daily for 7 d with cathode tsDCS; Healthy, no injury/no treatment; FIG. 4C shows the bar graphs of the percent change from pre-treatment evaluations or first evaluations for the healthy controls (Pre-eval) to E2-E4. Data are presented as the mean±SEM. *p<0.05 compared to Pre-eval.

FIG. 5B shows the respiratory rate (RR) during deep anesthesia (blue) and 45 min after an anesthetic injection (orange) are shown. The top section of FIG. 5C shows heart rate (HR) during deep anesthesia (blue) and 45 min after an anesthetic injection (orange) are shown. The bottom section of FIG. 5C shows full recording, with breaks, that shows the HR at which RDD testing took place. FIG. 5B depicts the changes that occurred when RDD was tested during deep anesthesia (Deep) versus light anesthesia (Light). E, Left: Representative recordings from the groups indicated. The left part of FIG. 5F shows bar graphs of the average RDD for the groups indicated. RDD was significantly higher in the control group (n=12) for rates 1-5 Hz compared to rate 0.1 Hz (p<0.001) and the right part of FIG. 5F shows the cumulative probability distribution of the groups indicated for RDD at 5 Hz. "Significant difference from RDD at 0.1 Hz in the same group; **Significant from respective RDD in the sham group. Data are presented as the mean±SEM.

FIG. 6B shows how NKCC1 expression was significantly increased in the sham-treated and cathode-treated groups, while the level in the anode-treated group did not differ from that of the control group. P-NKCC1 expression was not changed between groups. Detection of li-actin was included as a loading control. *p<0.05. Data are presented as mean±SEM.

FIG. 7A shows color maps (top) and original blots (bottom) of the Western blots performed for samples collected 2 h after stimulation to detect NKCC1 and p-NKCC1. Higher levels and lower levels of NKCC1 were detected after cathodal versus anodal stimulation, respectively, compared to the Sham samples. Detection of 1-actin was included as a loading control. FIG. 7B shows bar graphs of the band density data from FIG. 7A, including calculations of p-NKCC1/total NKCC1 ratios. *p<0.05. Data are presented as mean±SEM.

FIGS. 8A-8C show an anodal tsDCS-induced HSP70 response. Since anodal tsDCS led to a reduction in NKCC1 protein levels and not NKCC1 m RNA levels, the potential for HSP70 to mediate the degradation of NKCC1 was investigated. Tissue samples were collected from sham-treated intact animals (FIG. 8A) and 2 h after intact anesthetized animals received one session of anodal tsDCS (FIG. 8B). These samples were then stained for HSP 70 (green). Top, motor neuron nuclei; bottom, enlarged images of motor neurons. Asterisks indicate cell nuclei. Scale bars are indicated. In FIG. 8C, western blots showed a significant and consistent increase in HSP70 expression in the anode-treated animal samples versus the sham-treated samples (*p=0.03). Detection of I3-actin was performed as a loading control. Both color maps and the original blots are shown. Bottom: Bar graph representing the mean band densities for HSP70 relative to j3-actin in 1037 the sham and anode samples.

In FIGS. 9B/9C and FIGS. 9E/9F, bar graphs showing decreases in muscle resistance and concurrent EMG at low speed and high speed, respectively in each case, following bumetanide injection (n=9 mice). The negative values of EMG indicate stretches caused depression of EMG relative to background activity prior to stretching. Data are presented as mean±SEM. *p<0.05 compared to baseline 2 (BL2 was measured 5 minutes following the first baseline (BL1)).

DETAILED DESCRIPTION

Figure 1A:
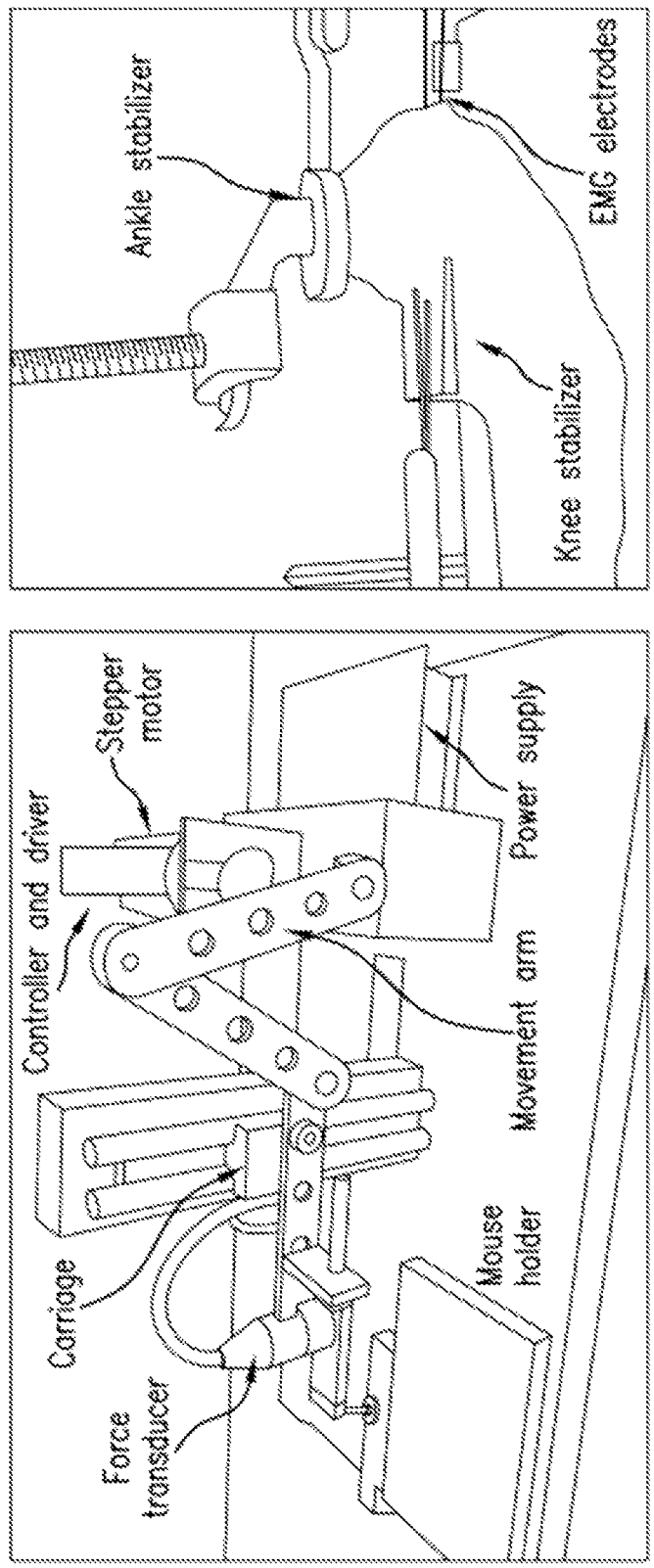
FIG. 1A-1D show a set up and procedure for testing spasticity in mice.
Figure 1B:
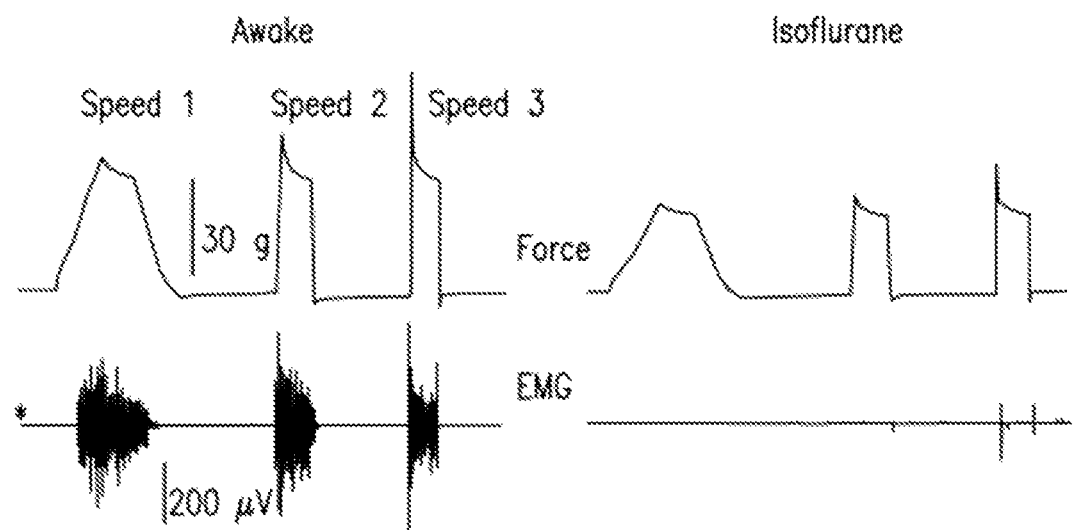
Figure 1C:
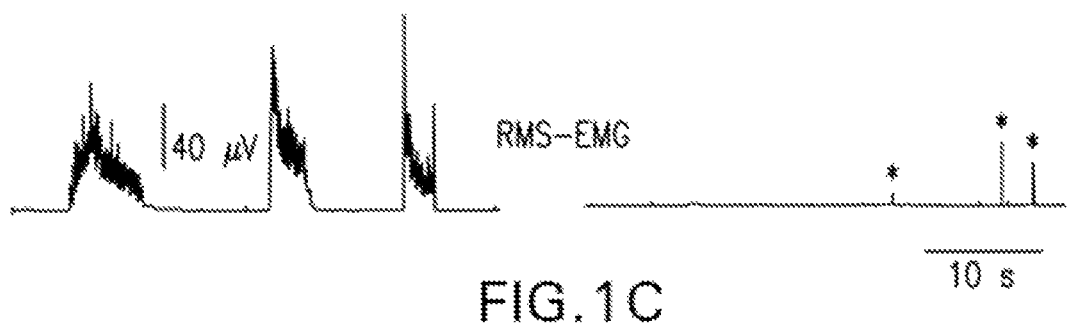
Figure 1D:
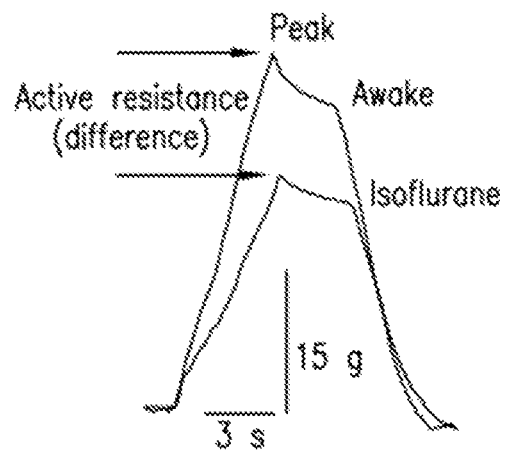

The description is not to be taken in a limiting sense, but is made merely for the purpose of illustrating the general principles of these teachings, since the scope of these teachings is best defined by the appended claims.

The above illustrative and further embodiments are described below in conjunction with the following drawings, where specifically numbered components are described and will be appreciated to be thus described in all figures of the disclosure.

As used herein, the singular forms "a," "an," and "the" include the plural reference unless the context clearly dictates otherwise.

The term "stimulation," as used herein, refers to either excitation or inhibition of nerve fibers, also referred to as up regulation or down regulation.

The term "electrical stimulation," as used here in refers to the production or introduction of current into spinal nerve, neuron, circuit or pathway, whether by applying a voltage or magnetically inducing a current.

Direct Current Stimulation (DCS) is a non-invasive methodology that encompasses using direct current to treat diseases and disorders in mammal, in particular disease and disorders affecting the nervous system of vertebrate beings. DCS includes trans-spinal direct current stimulation (tsDCS), trans-cranial direct current stimulation (tcDCS) and trans-peripheral nerve direct current stimulation (tpnDCS).

Trans-spinal direct current stimulation (tsDCS) is a non-invasive methodology that uses direct current to modulate spinal cord neurons. tsDCS can induce or suppress expression of specific proteins within the spinal cord cells. The modulation of expression of specific proteins can reduce or relieve spasticity, hypertonia and dystonia.

According to embodiments of the invention, tsDCS includes stimulation of a target spinal location or locations. The stimulation includes applying direct current along a defined current path that includes the target spinal location or locations. The stimulation in one illustrative embodiment is substantially continuous and non-varying at subthreshold level. In another illustrative embodiment the stimulation is varying in whole or in part. In another illustrative embodiment the stimulation includes a combination of varying and non-varying stimulation. In another illustrative embodiment the stimulation includes pulses of stimulation. In yet another illustrative embodiment the stimulation includes pulses of continuous current stimulation where the current flow is not monodirectional.

Trans-cranial direct current stimulation (tcDCS) is a non-invasive methodology that uses direct current to modulate cells of the brain. tcDCS can induce or suppress expression of specific proteins within the brain cells. The modulation of expression of specific proteins can be therapeutic for treating diseases and disorders including adrenoleukodystrophy (ADL), amyotrophic lateral sclerosis (ALS), Charcot-Marie-Tooth (CMT), Friedreich's ataxia (FA), Hallervorden-Spatz syndrome, hereditary spastic paraplegia (HSP), Huntington's disease, phenylketonuria, stroke, cerebral palsy, multiple sclerosis, Parkinson's disease, a neurodegenerative disease with Parkinsonian Syndromes, neonatal seizures, epilepsy, autism, spinal cord injury (SCI), traumatic brain injury (TBI), cerebral edema following ischemic and traumatic brain injury, brain damage due to lack of oxygen or exposure to carbon monoxide, encephalitis, meningitis, chronic pain, acute pain and tinnitus.

According to embodiments of the invention, tcDCS includes stimulation of a target cranial location or locations. The stimulation includes applying direct current along a defined current path that includes the target cranial location or locations. The stimulation in one illustrative embodiment is substantially continuous and non-varying at subthreshold level. In another illustrative embodiment the stimulation is varying in whole or in part. In another illustrative embodiment the stimulation includes a combination of varying and non-varying stimulation. In another illustrative embodiment the stimulation includes pulses of stimulation. In yet another illustrative embodiment the stimulation includes pulses of continuous current stimulation where the current flow is not monodirectional.

Trans-peripheral nerve direct current stimulation (tpnDCS) is a non-invasive methodology that uses direct current to modulate peripheral nerves. tpnDCS can induce or suppress expression of specific proteins within the peripheral nerve cells. The modulation of expression of specific proteins can reduce or relieve spasticity, hypertonia and dystonia.

According to embodiments of the invention, tpnDCS includes stimulation of a target peripheral nerve location or locations. The stimulation includes applying direct current along a defined current path that includes the target peripheral nerve location or locations. The stimulation in one illustrative embodiment is substantially continuous and non-varying at subthreshold level. In another illustrative embodiment the stimulation is varying in whole or in part. In another illustrative embodiment the stimulation includes a combination of varying and non-varying stimulation. In another illustrative embodiment the stimulation includes pulses of stimulation. In yet another illustrative embodiment the stimulation includes pulses of continuous current stimulation where the current flow is not monodirectional.

In practice of the invention, an electrode or array of electrodes is connected to a direct current source and placed at an area of interest, such as either directly over or near the dorsal aspect of the spinal cord, on the cranium or at or near a peripheral nerve. A return electrode or array of electrodes is placed distal therefrom to define a current flow path which in practice can be on the ventral aspect of the body, but not necessarily, directly opposite the electrode located at the area of interest. The direct current is applied to the treatment electrode located at the area of interest as either anode or cathode, depending upon function and desired stimulation.

The following terms may be understood, in the various illustrative by not limiting descriptions of embodiments of invention provided herein, to at least have the following definitions.

"Cathodal stimulation" refers to DCS where the cathode is placed at the desired area of interest for treatment.

"Anodal stimulation" refers to DCS where the anode is placed at the desired area of interest for treatment.

"Spasticity" is defined as the velocity-dependent over-activity of the stretch reflex. Thus, spasticity refers to a condition in which certain muscles are continuously contracted. This contraction causes stiffness or tightness of the muscles and can interfere with normal movement, speech and gait. Spasticity is usually caused by damage to the portion of the brain or spinal cord that controls voluntary movement. The damage causes a change in the balance of signals between the nervous system and the muscles. This imbalance leads to increased activity in the muscles.

"Hypertonia" refers to impaired ability of damaged motor neurons to regulate descending pathways giving rise to disordered spinal reflexes, increased excitability of muscle spindles, and decreased synaptic inhibition. These consequences result in abnormally increased muscle tone of symptomatic muscles. Hypertonia includes patients exhibiting increased muscle tone in the absence of stretch reflex over-activity, thus distinguishing hypertonia from spasticity.

"Dystonia" refers to a movement disorder in which a person's muscles contract uncontrollably. The contraction causes the affected body part to twist involuntarily, resulting in repetitive movements or abnormal postures. Dystonia can affect one muscle, a muscle group, or the entire body. Dystonia seems to be related to a problem in the basal ganglia, which is the pat of the brain that is responsible for initiating muscle contractions.

"Protein expression" refers to the level or amount of a protein or peptide contained within or produced by (e.g. excreted proteins or peptides) cells or tissues. "Differential expression", differential protein expression" and "differentially expressed" refer to a change in the level or amount of a protein or peptide contained within or produced by cells or tissues. Changes in protein expression can occur in response to specific external signals, such as chemical signals, mechanical signals or direct current stimulation. Such changes in expression can be an increase or a decrease in the level or amount of protein or peptide contained within or produced by cells or tissues. An increase in the level or amount of protein or peptide is also referred to as "up-regulation", and a decrease in the level or amount of protein or peptide is also referred to as "down-regulation".

"Messenger RNA expression" ("mRNA expression") refers to the level or amount of mRNA contained within cells or tissues. "Differential expression", "differential mRNA expression", "differential gene expression" and "differentially expressed" refer to a change in the level or amount of mRNA contained within cells or tissues. Changes in mRNA or gene expression can occur in response to specific external signals, such as chemical signals, mechanical signals or direct current stimulation. Such changes in expression can be an increase or a decrease in the level or amount of mRNA contained within cells or tissues. An increase in the level or amount of mRNA is also referred to as "up-regulation", and a decrease in the level or amount of mRNA is also referred to as "down-regulation". The terms "mRNA expression" and "gene expression" are used interchangeably throughout this disclosure.

In a previous study, the short-term effects of trans-spinal direct current stimulation (tsDCS) on muscle tone of the triceps surae muscle in mice was examined (Ahmed, 2014). Spinal stimulation resulted in significant modulatory effects on muscle tone, with cathodal tsDCS increasing muscle tone and anodal tsDCS reducing muscle tone. However, these were acute experiments performed in anesthetized animals. Therefore, critical questions remained, such as: How long can spinal-sciatic DC S-induced reset of spinal cord excitability be maintained? How long will this procedure influence muscle tone? How will spinal-sciatic DCS influence the recovery of unskilled and skilled locomotion following SCI?

The present invention supports the hypothesis that spinal-to-sciatic DCS (anodal tsDCS) will cause long-term normalization of spinal excitability, thereby promoting maintenance of reduced muscle tone and improved recovery of unskilled and skilled locomotion in vertebrate beings with SCI.

K—Cl co-transporter isoform 2 (KCC2) and Na—K—Cl co-transporter isoform 1 (NKCC1) are responsible for establishing chloride (Cl) concentrations across nerve cell membranes (Misgeld et at., 1986). Due to the importance of the electrochemical Cl gradient in determining the strength of inhibition mediated by GABA-A and glycine receptors, an imbalance in protein levels or the activities of KCC2 and NKCC1 has been predicted to lead to hyperexcitability and muscle dysfunction, particularly spasticity (Boulenguez et al., 2010: Modol et al., 2014). The mechanism of action underlying the long-term effects of direct current stimulation on spinal or brain excitability is largely unknown. It has been proposed that tsDCS can cause long-term changes in the excitability of spinal cord circuits (Ahmed, 2013; Ahmed, 2017; Bolzoni and Jankowska, 2015; Samaddar et al., 2016; Song et al., 2016; Wieraszko and Ahmed, 2016). Therefore, the present invention examined the effects of tsDCS on muscle tone mediated by changes in protein expression of NKCC1 and/or KCC2 in stimulated spinal tissue.

A combination of electrophysiology, a motorized system to test spasticity, and locomotor analysis were used to reveal the long-term influences of tsDCS on spasticity following SCI in awake mice. In addition, quantitative real-time PCR (qPCR), Western blotting, and immunohistochemistry were performed to identify changes in protein and/or gene expression of NKCC1 and KCC2 in stimulated spinal tissue.

Illustrative embodiments of the invention include treating diseases or disorders that include symptoms of spasticity, hypertonia or dystonia or have been associated with elevated NKCC1 expression. Representative examples of such diseases and disorders include adrenoleukodystrophy (ADL), amyotrophic lateral sclerosis (ALS), Charcot-Marie-Tooth (CMT), Friedreich's ataxia (FA), Hallervorden-Spatz syndrome, hereditary spastic paraplegia (HSP), Huntington's disease, phenylketonuria, stroke, cerebral palsy, multiple sclerosis, Parkinson's disease, a neurodegenerative disease with Parkinsonian Syndromes, neonatal seizures, epilepsy, autism, spinal cord injury (SCI), traumatic brain injury (TBI), cerebral edema following ischemic and traumatic brain injury, brain damage due to lack of oxygen or exposure to carbon monoxide, encephalitis, meningitis, chronic pain, acute pain and tinnitus.

Illustrative embodiments of the invention include methods of treating spasticity, hypertonia or dystonia comprising the step of administering a therapeutically effective amount of at least one agent that inhibits NKCC1 biological activity or at least one agent that decreases NKCC1 gene expression levels and/or protein expression levels.

In some embodiments, the at least one agent that inhibits NKCC1 biological activity or at least one agent that decreases NKCC1 gene expression levels and/or protein expression levels is at least one of pharmaceutical compounds, proteins, antibodies, nucleic acids or combinations thereof.

In some embodiments, the pharmaceutical compound that inhibits NKCC1 biological activity is at least one of sulfonamides, sulfonyl urea loop diuretics, thiazides or thiazide-like diuretics.

Representative examples of sulfonamides or sulfonyl urea loop diuretics are acetazolamide, azosemide, bumetanide, chlorthalidone, clopamide, furosemide, hydrochlorothiazide, indapamide, mefruside, metolazone, piretanide, tripamide, xipamide, dichlorphenamide, dorzolamide, ethoxzolamide, sultame, zonisamide, torsemide, phenoxycetic acid derivatives (ethacrynic acid, muzolimine), analogs thereof and combinations thereof.

Representative examples of thiazides or thiazide-like diuretics are bendoflumethiazide, benzthiazide, chlorothiazide, hydrochlorothiazide, hydroflumethiazide, methyclothiazide, polythiazide, trichlor-methiazide, chlorthalidone, indapamide, metolazone, quinethazone, analogs thereof and combinations thereof.

Additional pharmaceutical compounds that inhibit NKCC1 biological activity as well as analogs of the sulfonamides, sulfonyl urea loop diuretics, thiazides or thiazide-like diuretics listed above that can be used in the various embodiments disclosed herein are disclosed in WO2013/087090 and WO2014/191471, both of which are incorporated herein by reference in their entirety for all purposes.

Representative examples of nucleic acids that can be used to alter gene expression of a target molecule include RNA, siRNA, shRNA, micro-RNA, anti-sense RNA, RNAi, ribozymes, DNAzymes, peptide nucleic acids (PNAs), locked nucleic acids (LNAs), modified or synthetic DNA or RNA degradation-resistant polynucleoside amides, aptamers, transposons, transgenes and vectors for genetic engineering. In some embodiments, the nucleic acids described herein are used to lower or decrease levels of NKCC1 gene expression, which in turn, will result in lowered or decreased NKCC1 protein expression.

Representative examples of antibodies, which includes fragments thereof, that can be used to alter biological activity of or expression of a target molecule include monoclonal antibodies (mAb), polyclonal antibodies (pAb), humanized antibodies, antigen-binding fragments (Fab), variable fragments (Fv), single chain variable fragments (scFv), recombinant antibodies (rAb), Fab', (Fab')2, diabodies, triabodies, tetrabodies, Bis-scFv, minibodies, Fab2, Fab3, camelid/shark antibodies and nanobodies. In some embodiments, the antibodies or fragments thereof described herein are used to block or inhibit NKCC1 biological activity.

Representative examples of molecules that can be used to alter biological activity of or expression of a target molecule include proteins or combination of proteins and nucleic acids that are tools for genetic engineering such as Cas9 nucleases, CRISPR guide RNA, Cpf1 nuclease, HiFi Cas 9, Nickase Cas9, spCas9, scCas9, synthetic spCas9 and zinc finger nucleases. In some embodiments, the proteins or combination of proteins and nucleic acids are used lower or decrease levels of NKCC1 gene expression, which in turn, will result in lowered or decreased NKCC1 protein expression.

Representative examples of therapeutics that can be used in combination with the aforementioned therapeutics to treat spasticity, hypertonia or dystonia include botulinum toxin, short-acting serotype E botulinum toxin, baclofen, gabapentin, tizanidine, diazepam, clonazepam, dantrolene, phenol, clonidine, ketazepam, MDL28170, riluzole, cannabinoids, endocannabinoids and combinations thereof. Representative examples of cannabinoids and endocannabinoids include dronabinol, nabilone, nabiximols, endocannabinoid VNS16R, cannabidiol (CBD), tetrahydrocannabinol (THC) and combinations thereof.

Illustrative embodiments of the invention include methods of treating a disorder in a vertebrate being, including the steps of: applying stimulation between a first electrode and a second electrode of a direct current source with the first electrode being at or proximate to a dorsal aspect of a spinal cord of a vertebrate being or with the first electrode being on a cranium of a vertebrate being; and applying the direct current stimulation at an intensity and for a period of time sufficient to change biological activity of or level of gene expression and/or protein expression of NKCC1; wherein the second electrode is placed at a position remote from the first electrode and the first and second electrodes are oppositely charged, and wherein the direct current is at least one of constant, continuous, pulsed, intermittent, varying and non-varying.

Illustrative embodiments of the invention include methods of treating a disorder in a vertebrate being that are double stimulation methods, including the steps of applying a first stimulation between a first electrode and a second electrode of a direct current source with the first electrode being at or proximate to a dorsal aspect of a spinal cord of a vertebrate being; applying a second stimulation between a third electrode and a fourth electrode of a direct current source with one of the third electrode being at or proximate to a peripheral nerve of a vertebrate being; and applying the direct current stimulation at an intensity and for a period of time sufficient to change biological activity of or level of gene expression and/or protein expression of NKCC1; wherein the second electrode is placed at a position remote from the first electrode and the first and second electrodes are oppositely charged, and the fourth electrode is placed at a position remote from the third electrodes and the third and fourth electrodes are oppositely charged, and wherein the direct current is at least one of constant, continuous, pulsed, intermittent, varying and non-varying.

In some embodiments of the double stimulation method, the first and second stimulations are applied simultaneously or sequentially.

Illustrative embodiments of the invention include methods of treating a disorder in a vertebrate being that are triple stimulation methods, including the steps of applying a first stimulation between a first electrode and a second electrode of a direct current source with the first electrode being at or proximate to a dorsal aspect of a spinal cord of a vertebrate being; applying a second stimulation between a third electrode and a fourth electrode of a direct current source with one of the third electrode being at or proximate to a peripheral nerve of a vertebrate being; and applying the direct current stimulation at an intensity and for a period of time sufficient to change biological activity of or level of gene expression and/or protein expression of NKCC1; wherein the second electrode is placed at a position remote from the first electrode and the first and second electrodes are oppositely charged, and the fourth electrode is placed at a position remote from the third electrodes and the third and fourth electrodes are oppositely charged, and wherein the direct current is at least one of constant, continuous, pulsed, intermittent, varying and non-varying; and further comprising applying a third stimulation between a fifth electrode and a sixth electrode of a direct current source with the fifth electrode being on a cranium of a vertebrate being; and wherein the sixth electrode is placed at a position remote from the fifth electrode and the fifth and sixth electrodes are oppositely charged.

In some embodiments, of the triple stimulation method the first, second and third stimulations are applied simultaneously or sequentially.

In illustrative examples of the invention where peripheral nerves are stimulated, the peripheral nerve innervates a skeletal muscle. Representative examples of some peripheral nerves include leg nerves or arm nerves including, but not limited to a sciatic nerve, a peroneal nerve, a plantar digital nerve, a femoral nerve, a saphenous nerve, a sural nerve, a tibial nerve, a median nerve, a musculocutaneous nerve, a palmar digital nerve, a radial nerve, and an ulnar nerve.

In some embodiments of the single, double and triple stimulation methods, the stimulations are performed over a period of time that includes a series of stimulation sessions on 1 or more days, the days being consecutive or non-consecutive.

In some embodiments of the single, double and triple stimulation methods, the disorder being treated is a muscle tone disorder such as spasticity, spasticity following spinal cord injury, hypertonia and dystonia.

In some embodiments of the single, double and triple stimulation methods, the disorder being treated is a neurological disorder or condition such as adrenoleukodystrophy (ADL), amyotrophic lateral sclerosis (ALS), Charcot-Marie-Tooth (CMT), Friedreich's ataxia (FA), Hallervorden-Spatz syndrome, hereditary spastic paraplegia (HSP), Huntington's disease, phenylketonuria, stroke, cerebral palsy, multiple sclerosis, Parkinson's disease, a neurodegenerative disease with Parkinsonian Syndromes, neonatal seizures, epilepsy, autism, spinal cord injury (SCI), traumatic brain injury (TBI), cerebral edema following ischemic and traumatic brain injury, brain damage due to lack of oxygen or exposure to carbon monoxide, encephalitis, meningitis, chronic pain, acute pain and tinnitus.

In some embodiments of the single, double and triple stimulation methods, the biological activity of or the level of gene expression and/or protein expression of NKCC1 is decreased.

In some embodiments of the single, double and triple stimulation methods, the methods further include the step of administering a therapeutically effective amount of at least one agent that inhibits NKCC1 biological activity or at least one agent that decreases NKCC1 gene expression levels and/or protein expression levels.

In some embodiments of the single, double and triple stimulation methods, the methods further include the step of administering a therapeutically effective amount of at least one agent that increases KCC2 biological activity or at least one agent that increases KCC2 gene expression levels and/or protein expression levels.

In some embodiments, the agent is pharmaceutical compounds, proteins, antibodies, nucleic acids or combinations thereof.

In some embodiments, the pharmaceutical compound that increases KCC2 biological activity is N-ethylmaleimide.

Representative examples of nucleic acids that can be used to alter gene expression of a target molecule are described above. In some embodiments, the nucleic acids described herein are used to raise or increase levels of KCC2 gene expression, which in turn, will result raised or increased KCC2 protein expression.

Representative examples of antibodies, which includes fragments thereof, that can be used to alter biological activity of or expression of a target molecule are described above. In some embodiments, the antibodies or fragments thereof described herein are activating antibodies or fragments thereof that raise or increase KCC2 activity.

Representative examples of molecules that can be used to alter biological activity of or expression of a target molecule include proteins or combination of proteins and nucleic acids that are tools for genetic engineering as described above. In some embodiments, the proteins or combination of proteins and nucleic acids are used raise or increase levels of KCC2 gene expression, which in turn, will result in raise or increase KCC2 protein expression.

Illustrative embodiments of the invention include methods of treating ALS in a vertebrate being. The non-invasive electrical stimulation methods described herein are designed to halt the progression of ALS by protecting motor and cortical neurons from dying, i.e. the methods described herein prolong neuronal cell life or at least slow down the rate of motor and cortical neuron cell death. Without intending to be bound by theory, it is believed that suppressing NKCC1 expression and/or activity in spinal and cortical neurons will lead to this halt in the progression of ALS by prolonging motor and cortical neuronal cell life.

In some embodiments, the methods of treating ALS include the steps of: applying stimulation between an A electrode and a B electrode of a direct current source with the A electrode being at or proximate to a dorsal aspect of a spinal cord of a vertebrate being or with the A electrode being on a cranium of a vertebrate being; and applying the direct current stimulation at an intensity and for a period of time sufficient to prolong neuronal cell life associated with ALS disease state; wherein the B electrode is placed at a position remote from the A electrode and the A and B electrodes are oppositely charged, and wherein the direct current is at least one of constant, continuous, pulsed, intermittent, varying and non-varying.

It is envisioned that, when treating ALS patients, multiple spinal cord locations along the length of the spinal cord will be treated in order to prolong neuronal cell life at multiple locations. Accordingly, in some embodiments, the methods of treating ALS include a plurality of A electrodes located at or proximate to a plurality of positions along the dorsal aspect of the spinal cord and a plurality of B electrodes placed at positions remote from the plurality of A electrodes.

In other embodiments, one set of A and B electrodes is used, and the electrodes are moved to different locations along the length of the spinal cord in a series of treatments.

It is also envisioned that, when treating ALS patients, multiple regions of the brain associated with movement control will be treated including the motor cortex (Area 6 and Area 4, also known as the primary motor cortex), basal ganglia and the cerebellum. Accordingly, in some embodiments, the methods of treating ALS include a plurality of A electrodes located at a plurality of positions on the cranium associated with movement control and a plurality of B electrodes are placed at positions remote from the plurality of A electrodes. In other embodiments, one set of A and B electrodes is used, and the electrodes are moved to different cranial positions associated with movement control in a series of treatments.

In some embodiments of the methods of treating ALS, the stimulation applied between the plurality of A and B electrodes is applied simultaneously or sequentially.

In some embodiments, the methods of treating ALS patients include the steps of: applying a first stimulation between an A electrode and a B electrode of a direct current source with the A electrode being at or proximate to a dorsal aspect of a spinal cord of a vertebrate being; applying a second stimulation between a C electrode and a D electrode of a direct current source with the C electrode being on a cranium of a vertebrate being; and applying the direct current stimulation at an intensity and for a period of time sufficient to prolong neuronal cell life; wherein the B electrode is placed at a position remote from the A electrode and the A and B electrodes are oppositely charged, and the D electrode is placed at a position remote from the C electrode and the C and D electrodes are oppositely charged, and wherein the direct current is constant or pulsed. In some embodiments, the first and second stimulations are applied simultaneously or sequentially.

In some embodiments, the methods of treating ALS include a plurality of A electrodes located at or proximate to a plurality of positions along the dorsal aspect of the spinal cord and a plurality of B electrodes placed at positions remote from the plurality of A electrodes. In other embodiments, one set of A and B electrodes is used, and the electrodes are moved to different locations along the length of the spinal cord in a series of treatments.

In some embodiments, the methods of treating ALS include a plurality of C electrodes located at a plurality of positions on the cranium associated with movement control and a plurality of D electrodes are placed at positions remote from the plurality of C electrodes. In other embodiments, one set of C and D electrodes is used, and the electrodes are moved to different cranial positions associated with movement control in a series of treatments.

In some embodiments, the stimulation applied between the plurality of A and B electrodes and between the plurality of C and D electrodes is applied simultaneously or sequentially.

In some embodiments, the methods of treating ALS further include applying a third stimulation between an E electrode and an F electrode of a direct current source with the E electrode being at or proximate to a peripheral nerve of a vertebrate being; and wherein the F electrode is placed at a position remote from the E electrode and the E and F electrodes are oppositely charged. In some embodiments the first, second and third stimulations are applied simultaneously or sequentially.

In some embodiments, the methods of treating ALS include a plurality of E electrodes located at or proximate to a plurality of positions along a peripheral nerve or are located at or proximate to a plurality of peripheral nerves and a plurality of F electrodes are placed at positions remote from the plurality of E electrodes. In other embodiments, one set of C and D electrodes is used, and the electrodes are moved to different positions along a peripheral nerve or are moved to different peripheral nerves. In some embodiments, the stimulation applied between the plurality of E and F electrodes is applied simultaneously or sequentially. In some embodiments where peripheral nerves are stimulated, the peripheral nerve innervates a skeletal muscle. Representative examples of some peripheral nerves are disclosed above.

In some embodiments of the methods of treating ALS, the period of time comprises a series of stimulation sessions on 1 or more days, the days being consecutive or non-consecutive.

In some embodiments of the methods of treating ALS, the method includes applying the direct current stimulation at an intensity and for a period of time sufficient to change biological activity of or level of gene expression and/or protein expression of NKCC1. In some embodiments, the biological activity of or the level of gene expression and/or protein expression of NKCC1 is decreased.

In some embodiments of the methods of treating ALS, the non-invasive DCS methods are combined with the step of administering a therapeutically effective amount of at least one agent that inhibits NKCC1 biological activity or at least one agent that decreases NKCC1 gene expression levels and/or protein expression levels. In certain embodiments, the agent is pharmaceutical compounds, proteins, antibodies, nucleic acids or combinations thereof as described herein above.

In some embodiments of the methods of treating ALS, the non-invasive DCS methods are further combined with the step of administering a therapeutically effective amount of at least one agent that increases KCC2 biological activity or at least one agent that increases KCC2 gene expression levels and/or protein expression levels. In certain embodiments, the agent is pharmaceutical compounds, proteins, antibodies, nucleic acids or combinations thereof as described herein above.

Figure 12:
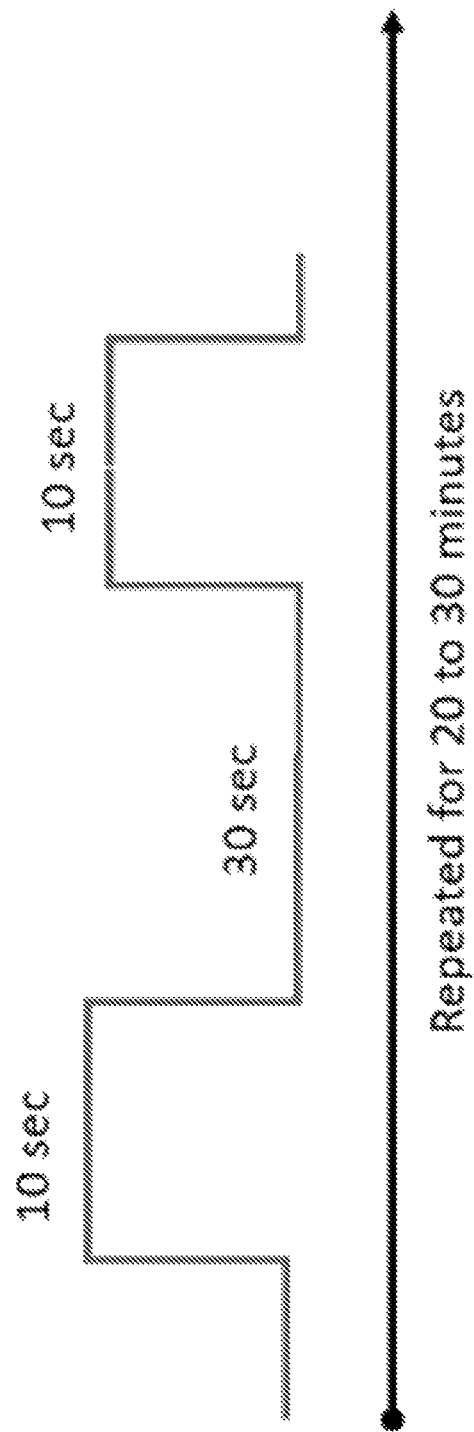
FIG. 12 is a graphic representation of a proposed stimulation prescription for deep brain structures (e.g., for stimulating basal ganglia). The proposed mode is long-pulsed monopolar direct current (DC) at an intensity of about 10 mA for a duration of about 10 seconds and with a rest period of about 30 seconds between stimulations. The treatment duration is proposed to be about 20-30 minutes.

Animals, particularly mammals including humans, are the subjects of the DCS treatments discussed herein. In illustrative and non-limiting embodiments, treatment of humans in practice of the invention can include application of tsDCS, for example, generally within a range of over 1 mA and under 6 mA, and more particularly within a range of about 3.5-4 mA, and can be applied for about 20-40 min/day. In other illustrative and non-limiting embodiments, treatments of humans in practice of the invention can include application of transcranial DCS (tcDCS). As depicted in FIG. 12, a proposed stimulation prescription for deep brain structures (e.g., for stimulating basal ganglia) includes a long-pulsed monopolar direct current (DC) at an intensity of about 10 mA for a duration of about 10 seconds and with a rest period of about 30 seconds between stimulations. The treatment duration is proposed to be about 20-30 minutes. DCS treatment can be as often as indicated on a scheduled day or alternating days, or any other treatment regime intended to affect repair or recovery.

In practicing the methods of the invention disclosed herein, the following systems or devices are used.

Illustrative embodiments of the invention include a system for treatment of spasticity, hypertonia or dystonia in a vertebrate being, the system including: a first stimulation component configured to provide peripheral direct current stimulation of a peripheral nerve associated with spasticity, hypertonia or dystonia in a vertebrate being; the first stimulation component including a neural stimulation circuit having neural stimulation poles configured to stimulate said peripheral nerve; a second stimulation component configured to provide spinal direct current stimulation at a spinal location associated with regulation of said peripheral nerve, said second stimulation component defining a spinal stimulation circuit having an active spinal stimulation pole and a spinal reference pole, said spinal stimulation circuit configured to provide constant-current trans-spinal direct current stimulation between said spinal stimulation pole and said spinal reference pole for stimulating said spinal location; the active spinal stimulation pole being relatively proximal to said spinal location; the spinal reference pole being relatively distal to said spinal location; and a controller component configured to ensure that said active spinal pole and said proximal neural pole are excited at opposite polarities, forming a resulting polarization circuit, said resulting polarization circuit being configured to provide a polarizing current flow between said active spinal pole and said proximal neural pole according to said opposite polarities, for changing biological activity of or level of gene expression and/or protein expression of a target molecule according to said polarizing current flow; said controller component being also configured to provide peripheral direct current stimulation and spinal direct current stimulation for a predetermined time period and repeat stimulation a predetermined number of times over a predetermined number of days.

In some embodiments of the system, the controller component is configured to provide said current flow including at least one of constant, continuous, pulsed, intermittent, varying and non-varying current flow.

In some embodiments of the system, the controller component is further configured to simultaneously control the range of current supplied by the first and second stimulation components.

In some embodiments of the system, the first stimulation component includes positive and negative poles for providing stimulation current to stimulation electrodes disposed for stimulation of said peripheral nerve, said positive and negative poles disposed for one electrode operatively connected to the positive pole and another electrode operatively connected to the negative pole. In some embodiments of the system, the second stimulation component includes positive and negative poles for providing stimulation current to stimulation electrodes disposed for delivering stimulation across said spinal location, said positive and negative poles disposed for one electrode operatively connected to the positive pole and another electrode operatively connected to the negative pole.

In some embodiments of the system, at least one of the stimulation electrodes is implanted.

In yet other embodiments of the system, at least one of the controller component and an electrical source are disposed in a wearable housing.

In some embodiments of the system, the predetermined time period, the predetermined number of times and the predetermined number of days are selected to change biological activity of or level of gene expression and/or protein expression of NKCC1. In certain embodiments of the system, the biological activity of or the level of gene expression and/or protein expression of NKCC1 is decreased.

Illustrative embodiments of the invention include a stimulation device for regulating biological activity associated with one of the spinal cord or the brain, comprising: a direct current voltage source having a plurality of terminals; a first of the terminals for connecting a first electrode to the direct current voltage source; the first electrode being at one of a dorsal aspect of a spinal cord of a vertebrate being or on a cranium of a vertebrate being; a second of the terminals for connecting a second electrode to the direct current voltage source; the second electrode being placed at a position remote from the first electrode; the first and second electrodes being oppositely charged; and a controller component configured to control of current flow between the electrodes; the controller component being also configured to provide direct current stimulation for a predetermined time period and repeat stimulation a predetermined number of times over a predetermined number of days.

In some embodiments of the stimulation device, the controller component is configured to provide said current flow including at least one of constant, continuous, pulsed, intermittent, varying, and non-varying current flow.

In some embodiments of the stimulation device, at least one of the first and second electrodes is implanted.

In yet other embodiments of the stimulation device, at least one of the controller component and the direct current voltage source are disposed in a wearable housing.

In some embodiments of the stimulation device, the predetermined time period, the predetermined number of times and the predetermined number of days are selected to change biological activity of or level of gene expression and/or protein expression of NKCC1. In certain embodiments of the stimulation device, the biological activity of or said level of gene expression and/or protein expression of NKCC1 is decreased.

Illustrative embodiments of the invention include systems for treatment of ALS in a vertebrate being, the system including: a plurality of A stimulation components configured to provide peripheral direct current stimulation of a peripheral nerve at a plurality of locations along the peripheral nerve or to provide peripheral direct current stimulation of a plurality of peripheral nerves in a vertebrate being; each of said A stimulation components including a neural stimulation circuit having neural stimulation poles configured to stimulate said peripheral nerve or plurality of peripheral nerves; a plurality of B stimulation components configured to provide spinal direct current stimulation at a plurality of spinal locations associated with regulation of said peripheral nerve or plurality of peripheral nerves, each of said B stimulation components defining a spinal stimulation circuit having an active spinal stimulation pole and a spinal reference pole, said spinal stimulation circuit configured to provide constant-current trans-spinal direct current stimulation between said spinal stimulation pole and said spinal reference pole for stimulating said spinal location; the active spinal stimulation pole being relatively proximal to said spinal location; the spinal reference pole being relatively distal to said spinal location; and a controller component configured to ensure that said active spinal pole and said proximal neural pole are excited at opposite polarities, forming a resulting polarization circuit, said resulting polarization circuit being configured to provide a polarizing current flow between said active spinal pole and said proximal neural pole according to said opposite polarities, for changing biological activity of or level of gene expression and/or protein expression of a target molecule according to said polarizing current flow; said controller component being also configured to provide peripheral direct current stimulation and spinal direct current stimulation for a predetermined time period and repeat stimulation a predetermined number of times over a predetermined number of days.

In some embodiments of the system, the controller component is configured to provide said current flow including at least one of constant, continuous, pulsed, intermittent, varying and non-varying current flow.

In some embodiments of the system, the controller component is further configured to simultaneously control the range of current supplied by the A and B stimulation components.

In some embodiments of the system, the A stimulation components include positive and negative poles for providing stimulation current to stimulation electrodes disposed for stimulation of said plurality of locations of a peripheral nerve or said plurality of peripheral nerves, said positive and negative poles disposed for one electrode operatively connected to the positive pole and another electrode operatively connected to the negative pole.

In some embodiments of the system, the B stimulation components include positive and negative poles for providing stimulation current to stimulation electrodes disposed for delivering stimulation across said plurality of spinal locations, said positive and negative poles disposed for one electrode operatively connected to the positive pole and another electrode operatively connected to the negative pole.

In some embodiments of the system, at least one of the stimulation electrodes is implanted.

In yet other embodiments of the system, at least one of the controller component and an electrical source are disposed in a wearable housing.

In some embodiments of the system, the predetermined time period, the predetermined number of times and the predetermined number of days are selected to change biological activity of or level of gene expression and/or protein expression of NKCC1. In certain embodiments of the system, the biological activity of or the level of gene expression and/or protein expression of NKCC1 is decreased.

Illustrative embodiments of the invention include a stimulation device for treatment of ALS, comprising: a direct current voltage source having a plurality of terminals; a plurality of A terminals for connecting a plurality of A electrodes to the direct current voltage source; the plurality of A electrodes being at a plurality of locations of a dorsal aspect of a spinal cord of a vertebrate being or at a plurality of locations on a cranium of a vertebrate being; a plurality of B terminals for connecting a plurality of B electrodes to the direct current voltage source; the plurality of B electrodes being placed positions remote from the plurality of A electrodes; the A and B electrodes being oppositely charged; and a controller component configured to control of current flow between the electrodes; the controller component being also configured to provide direct current stimulation for a predetermined time period and repeat stimulation a predetermined number of times over a predetermined number of days.

In some embodiments of the stimulation device, the controller component is configured to provide said current flow including at least one of constant, continuous, pulsed, intermittent, varying, and non-varying current flow.

In some embodiments of the stimulation device, at least one of the A and B electrodes is implanted.

In yet other embodiments of the stimulation device, at least one of the controller component and the direct current voltage source are disposed in a wearable housing.

In some embodiments of the stimulation device, the predetermined time period, the predetermined number of times and the predetermined number of days are selected to change biological activity of or level of gene expression and/or protein expression of NKCC1. In some embodiments of the stimulation device, the biological activity of or the level of gene expression and/or protein expression of NKCC1 is decreased.

The systems and stimulation devices of the present invention are further described below with reference to the figures.

Figure 13A:
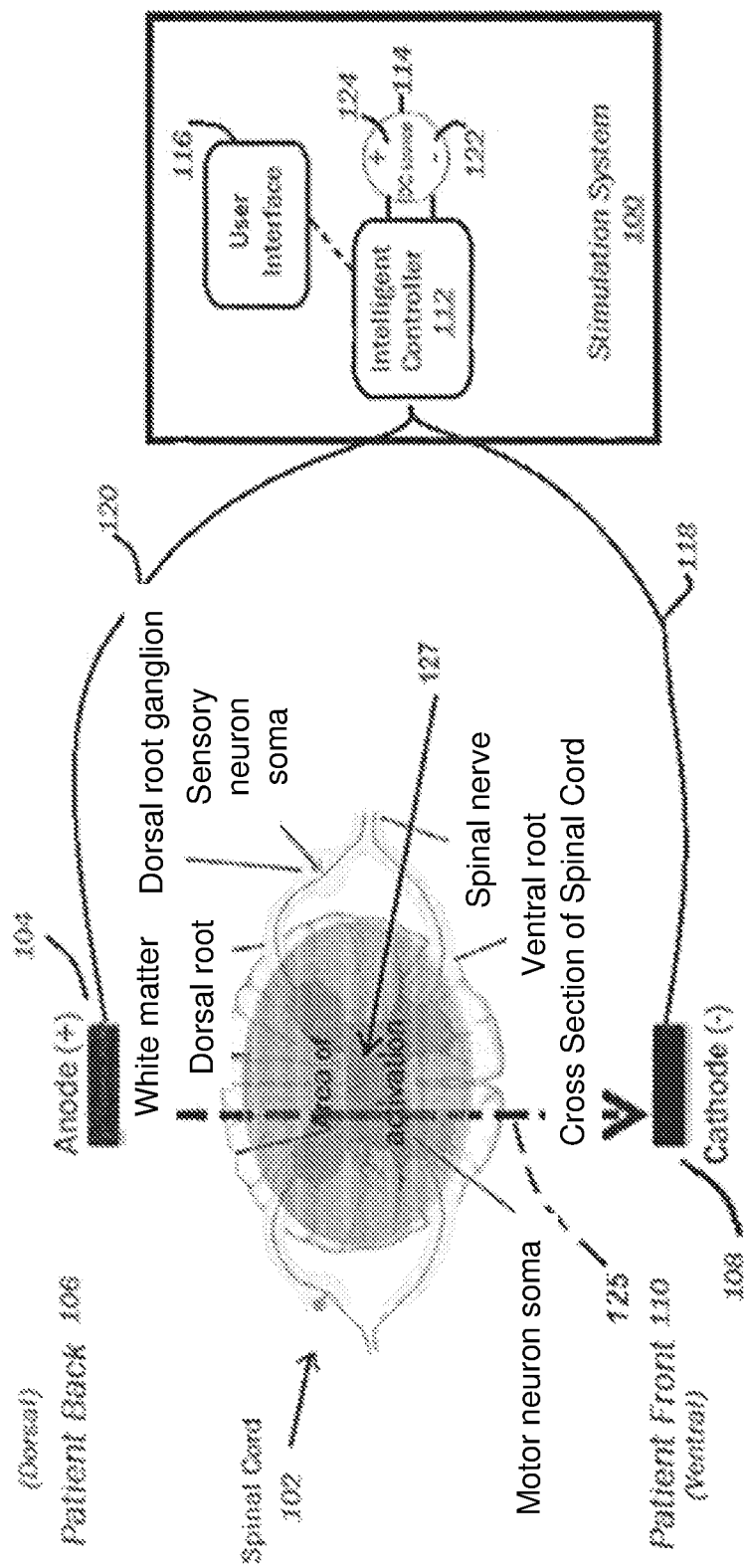
FIG. 13A shows an embodiment of a stimulation system of the invention configured to apply trans-spinal Direct Current Stimulation (tsDCS) to the spinal cord (dorsal to ventral).

FIG. 13A shows an embodiment of a stimulation system 100 of the invention configured to apply tsDCS stimulation to the spinal cord 102 (shown in cross-section) through application of electrode 104 on the dorsal side 106 at the spinal aspect 105 of the subject and location of an electrode 108 at an opposing ventral aspect 110, or other distal location, such as at the abdomen. Electrodes 104 and 108 are shown provided as anode and cathode, respectively, as an illustration only. In other embodiments, electrodes 104 and 108 are provided as cathode and anode, respectively. In various applications of the invention, the polarity of the electrode applied at the principal location, such as at the dorsal aspect 105 at a location of interest, defines the circuit configuration as either "anodal" or "cathodal".

In an illustrative embodiment of the invention of FIG. 13A, system 100 includes a direct current source 114 having terminals 122, 124. A first electrode 104 is attached to a first of the terminals and to a dorsal aspect 105 of a vertebrate being. A second electrode 108 is attached to a second of the terminals and to a target ventral location 110 of the vertebrate. The stimulation proceeds between dorsal electrode 104 and ventral side electrode 108. The current will proceed from anode to cathode, as assigned. Intelligent controller 112 controls the signal applied to such attached electrodes and thus controls the direction of current flow and thus defines the flow path 125 between the first electrode 104 and the second electrode 108.

In one illustrative practice of the invention, an anodal tsDCS configuration is established at the spinal cord 102 of a subject, as shown in FIG. 13A, where electrode 104 is made anodal as it is connected to the positive current source 124 by controller 112, and the return electrode 108 is cathodal, as connected to the negative current source 122, by controller 112, under direction of user interface 116. The return electrode is preferably applied on the corresponding ventral aspect although it may be offset or more distal depending upon the intended current flow path 125, such as shown in FIG. 13A, as will locate the area of activation 127 of such stimulation.

As will be appreciate by a person skilled in the art, in one embodiment, the intelligent controller 112 includes an internal instruction set and may be further informed via data from memory 117 or by user intervention at interface 116. Intelligent controller 112 enables application of current from DC source 114 to electrodes 104, 108. In one illustrative embodiment, the negative current source 122 of DC source 114 is connected to electrode 108 (now functioning as the cathode) via lead 118 and the positive current source 124 of DC source 114 is connected to electrode 104 via lead 120 (now functioning as the anode). In one embodiment, DC source 114 includes battery 115. In practices of the invention, the battery may be understood to include at least one of a capacitive storage device, a rechargeable device, a lithium-ion battery, and other electrical sources.

In illustrative embodiments of the invention, system 100 further includes a signal controller circuit 111 in electrical communication with at least one of the electrodes and with the direct current source, for maintaining constant current tsDCS current flow between electrodes 104, 108 in response to changes in voltage detected across the first and second terminals 122, 124, as will be understood by a person skilled in the art. In embodiments of the invention, signal controller circuit 111 is further configured to regulate the DC signal to provide the stimulation signal 126 as at least one of constant, continuous, pulsed, intermittent, varying, and non-varying as directed by controller 112. In various embodiments of the invention, several of these variations can be implemented as part of or added to the desired tsDCS stimulation of the invention to achieve a desired stimulation performance, as will be appreciated by a person skilled in the art.

In illustrative embodiments of the invention, the system of the invention has a control circuit including a signal controller circuit 111, intelligent controller circuit 112, DC source 114, battery 115, user interface 116, and memory 117 are supported in a housing 130, which may be for benchtop use or for use as a wearable or implantable device, and may be watertight, all in practice of embodiments of the invention.

Figure 14:
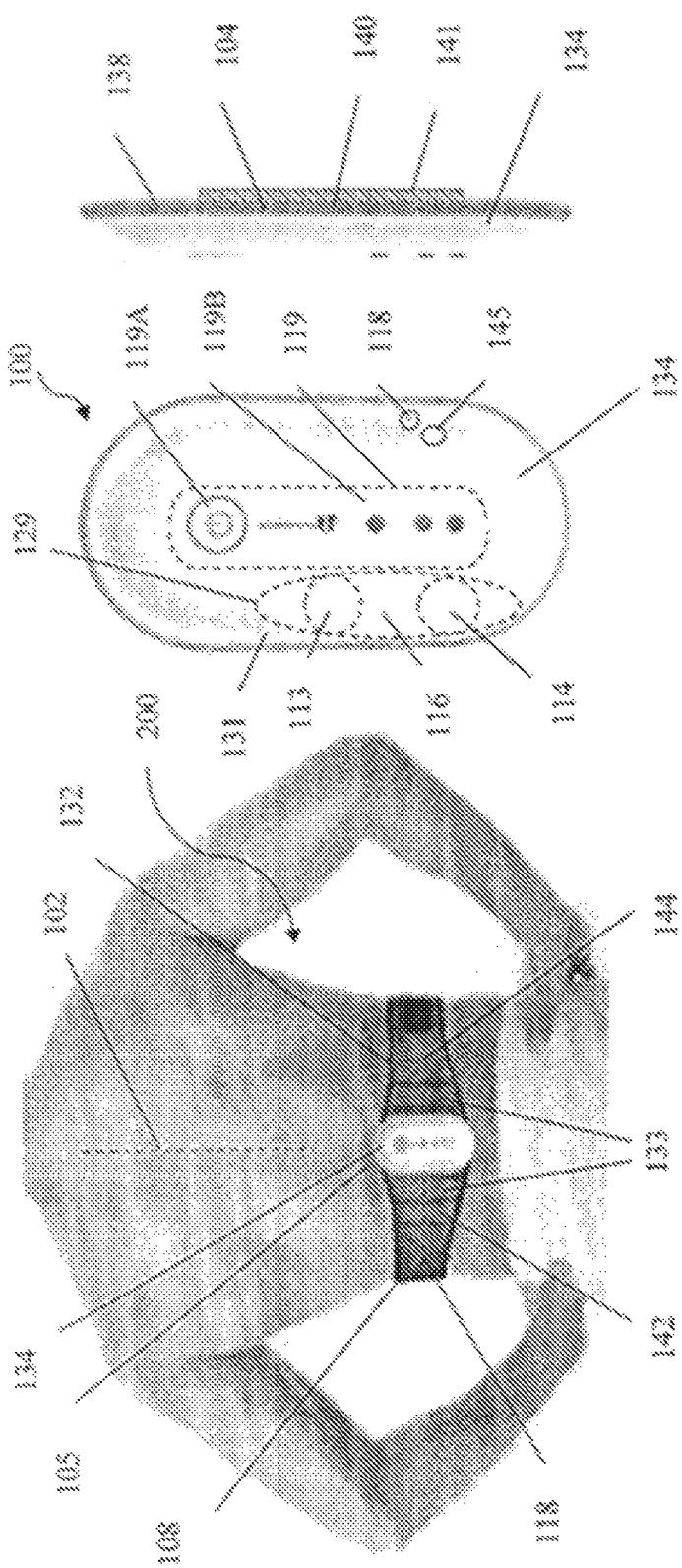
FIG. 14A shows an embodiment of a wearable tsDCS device affixed on a patient.
FIGS. 14B and 14C show in plan and side vies, respectively, an embodiment of the wearable device of FIG. 14A.

In the illustrative embodiments of FIGS. 14A-C, a wearable housing system 200 includes the system 100 in a wearable housing 131 having a wearable attachment system 132. The wearable attachment system 132 enables presentation of the housing 131 as a slim and wearable package 134. In one practice of the invention, the back surface 138 of package 134 itself is applied to the target dorsal location 105, and, in one embodiment, is provided with a conductive electrode 104 defined by surface 140 and is connected to the internal DC source 114. Surface 140 may further include an electrically conductive adhesive 141, all to provide the desired signal at electrode 104 when attached on the vertebrate patient.

As shown in FIGS. 14A-C, in one illustration, the attachment system 132 further includes wearable material 133 such as straps 142, 144 (with connecting Velcro, buckles, or the like) to further secure system 100 to the patient. The return electrode 108 is connected to DC source 114 via lead 118 which in this illustrative embodiment is connected to the current source via a sealed pass-through or port 145 of housing 131 and then affixed to and running along the skin-side of strap 142 to make electrical contact via electrode 108 to provide the desired ventral electrical connection to the patient. The electrode lead can be attached to or contained within the wearable material 133. In a further illustrative embodiment shown in FIG. 12B, user interface 116 includes user control pad 119 including operator control 119A and indicator lights 119B, for enabling switching of modes of operation and providing indication thereof.

Wearable material 133 can be a strap, cloth, elastic, harness or other wearable material configured to allow the electrode surface to be in contact with the skin of the vertebrate. Alternatively, the electrode surface can be attached or affixed to the skin surface via an adhesive mounting or by implanted magnets. In various embodiments of the invention, the wearable material can be provided in varying sizes and form factors depending on the size of the vertebrate (e.g., adult or child) and depending on the spinal location being treated. Alternatively, the wearable material can be adjustable to accommodate subjects of varying sizes and spinal location being treated. The wearable material enables positioning the electrode 104 surface on the skin in the area of the dorsal aspect of the subject. The wearable tsDCS device can be rechargeable and can be removed at night for charging and comfort of sleep. The wearable tsDCS device can be attached to the skin surface of the spine at the cervical, thoracic, lumbar or sacral levels depending on the site to be treated.

It will be appreciated by a person skilled in the art that intelligent controller 112 is controlled such as from human interface 116 or internally using data stored in memory 117 to establish circuit connection between electrodes 104, 108 and the terminals 122, 124 of source 114 according to a given treatment protocol to be implemented, whether anodal or cathodal.

The memory 117 may include one or a series of data matrices which can be accessed to inform controller 112, as will be understood by a person skilled in the art. For example, the system 100 could be applied to the human and then turned on to perform a routine whose commands are stored in memory 117, such as pulsations or periods of treatment over time, and which are accessed from time to time by a routine initiated at controller 112, for providing a desired stimulation treatment. However, it will be understood that in a simple practice of the invention, the stimulation device can be set as an anodal or cathodal system without needing the intelligent control components of stimulation system 100.

Figure 13B:
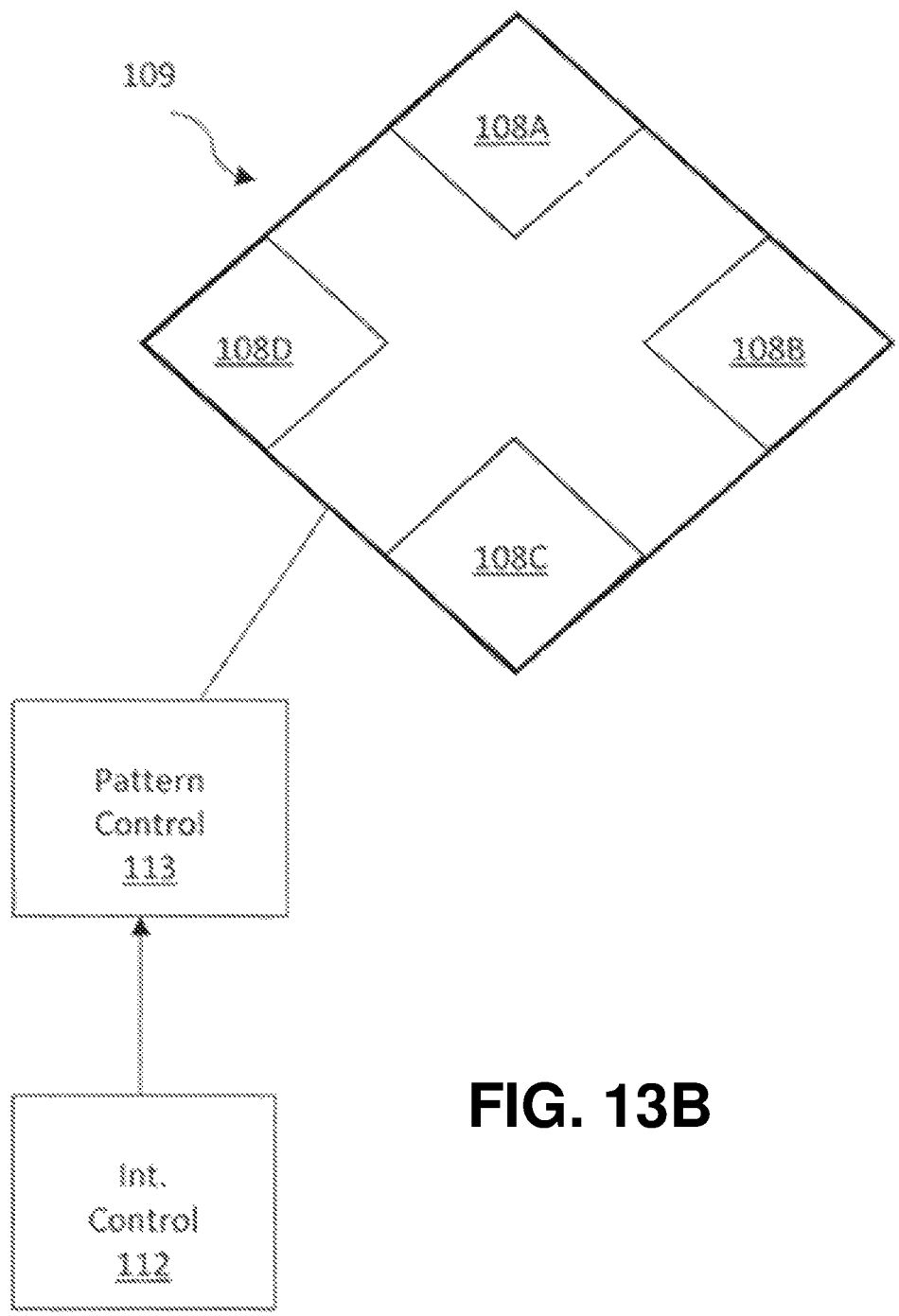
FIG. 13B shows an electrode array in practice of an embodiment of a stimulation system of the invention.

In a further illustrative embodiment, at least one of the cathode and anode electrodes is comprised of an array of component electrodes. In one illustrative practice thereof, the stimulation system 100 of FIG. 13A includes the electrodes 104 and 108 where, and as shown in the illustration of FIG. 13B, electrode 108 is comprised of an array 109 of electrodes 108A-D. In one illustrative practice of such an embodiment, each electrode of array 109 is capable of being separately stimulated whereupon the stimulated cells are favorably biased or steered toward achieving the desired stimulation goal.

In one illustrative embodiment of the invention, a pattern controller 113 is provided, and as instructed by intelligent controller 112, drives a desired stimulation pattern for the array of electrodes 108A-D. For example in one practice of this embodiment, the electrodes 108A-D of array 109 are sequentially stimulated so as to give target cells a rotational component. In another practice of this embodiment, or one or two of the electrodes is stimulated so as to give the target cells an angular component, as will enable direction of the movement of the target cells as needed to access its value at a target location. As a person skilled in the art will understand, this steering is analogous to the use of virtual steering done with DSP beam steering, such as used in the audio field, although here the purpose is steering various cells within the patient. In one embodiment, pattern controller 113 is incorporated into the wearable device 134 as shown in FIG. 12B.

It will now be appreciated that in practices of the invention, anodal tsDCS refers to stimulation with the anode associated with the dorsal aspect of the spinal cord and the cathode associated with the ventral aspect. Cathodal tsDCS refers to stimulation with the cathode associated with the dorsal aspect of the spinal cord and the anode associated with the ventral aspect.

In another illustrative practice of the invention, in a cathodal tsDCS configuration using the system of FIG. 13A, electrode 104 is connected to negative source 122 and is applied at a desired dorsal location 105 and the anodal electrode is applied ventrally and is connected to the positive source 124, by controller 112. An increase of protein in the cells at the desired spinal cord area of activation 127 under cathodal tsDCS stimulation is demonstrated by increase of HSP70 as shown in FIG. 9. In one illustrative embodiment, the stimulation session duration spans from 20 to 40 minutes to achieve this positive result. Multiple sessions are indicated for added positive results according to patient need.

It will be appreciated by a person skilled in the art that the return electrode 108 is preferably applied on the corresponding ventral aspect although it may be offset or more distal depending upon the intended current flow path 125. In an illustrative practice of the invention, the return electrode 108 is applied opposite to the distal stimulation electrode 104 at the spine or at an aspect of the cranium, the neck, torso or an extremity, depending upon the intended current flow path 125 and intended area of activation 127. The present invention is further illustrated by the following specific example of tsDCS in a mouse model. The example is provided for illustration only and is not to be construed as limiting the scope or content of the invention in any way.

In one embodiment, the system includes a first stimulation component, a second stimulation component and a controller.

In one instance, the first stimulation component includes a first electrical source with positive and negative terminals providing stimulation current to stimulation electrodes, including two electrodes disposed for stimulation of a nerve associated with a target effector organ; one electrode operatively connected to the positive terminal and another electrode operatively connected to the negative terminal; each one of the two electrodes being electrically insulated from the other one of the two electrodes. In one embodiment, the two electrodes are located noninvasively and are skin-surface electrodes. In another embodiment the two electrodes are implanted electrodes. In one instance, the first electrical sources also implanted and the controller component is operatively connected to the first electrical source by a wireless connection.

In one instance, the second stimulation component includes a second electrical source having a second positive terminal and a second negative terminal, a first electrode disposed to be placed at a spinal cord location and a second electrode disposed to be placed at a location selected from another location at the spinal column or a location distal from the spine. One of the first and second electrodes is operatively connected to the second positive terminal and another one of the first and second electrodes is operatively connected to the second negative terminal.

In one embodiment, the first and second electrical sources are the same source. In another embodiment, the first and second electrical sources and the control component are located in a wearable housing. In one embodiment, the source is a DC source. It should be noted that embodiments in which the first electrical source is a pulsed source, such as a pulsed DC source, are also within the scope of these teachings. Although less frequently used, embodiments in which the source is a pulsed AC source are also within the scope of these teachings.

Figure 15:
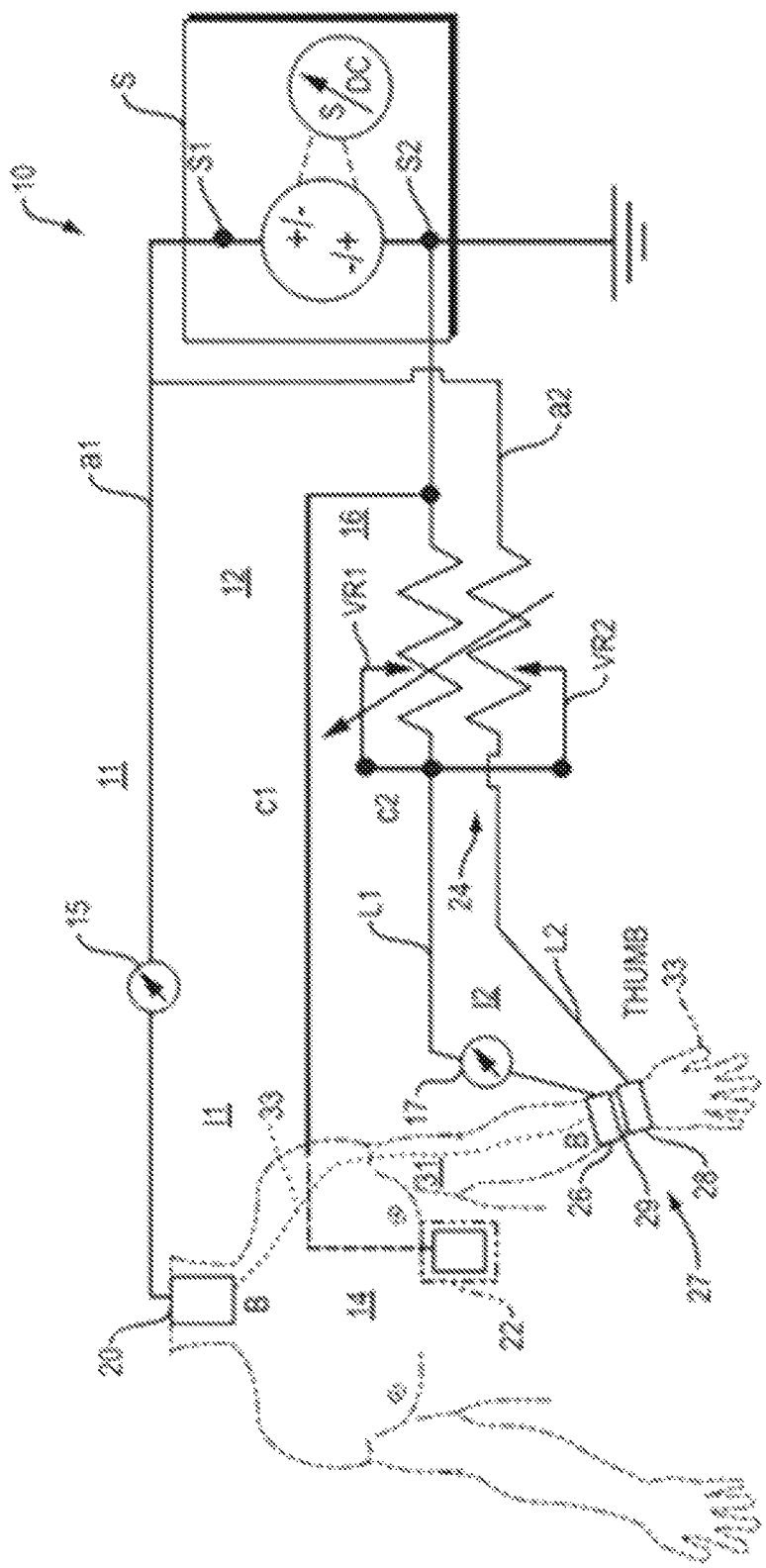
FIG. 15 illustrates an embodiment of these teachings for regulating the median nerve for resolving a chronic fisted hand and fingers with high muscle tone.

In an embodiments, these two circuits define a resulting polarization circuit defined between respective electrodes. An exemplary embodiment is shown in shown in FIG. 15 as between an anodal electrode 20 of the spinal circuit 12 and a cathodal electrode 26 of the neural circuit 16. The resulting polarization circuit 33 stimulates the spine and achieves a desired regulation of excitability of effected spinal motoneurons and interneurons that enables the desired outcome of regulation of muscle tone.

Down regulation and up regulation of muscle tone are guided by the direction of the interaction between these adjacent electrodes of the spinal and neural circuits 12, 16 that define the polarization circuit 33. For down-regulation, the spinal electrode 20 is positive ("anodal") and proximal peripheral nerve electrode 26 must be negative ("cathodal"). This defines the needed spine-to-nerve polarization circuit 33 (polarizing current flow path) between these two energized electrodes of the two polar circuits 12, 16 for down-regulation. For up-regulation, the proximal nerve electrode 26 is positive ("anodal") and spinal electrode must be negative ("cathodal"). In several embodiments, this defines the nerve-to-spine polarization circuit 33 (polarizing current flow path) between these two energized electrodes of the two polar circuits for up-regulation.

Figure 16:
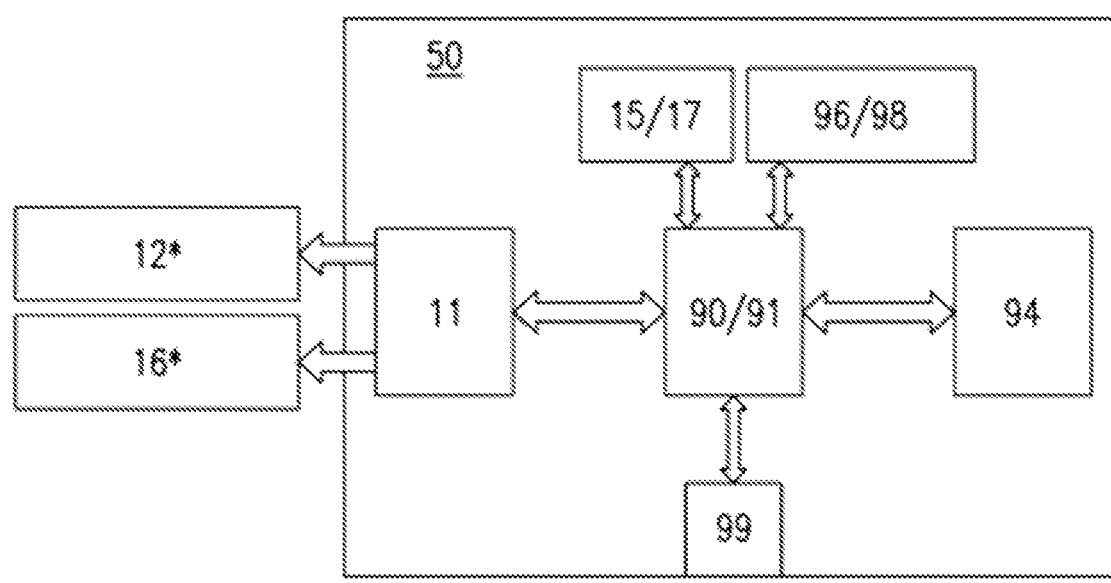
FIG. 16 is a Block diagram of an illustrative embodiment of these teachings.

A block diagram of one embodiment is shown in FIG. 16. Controller circuit 90 monitors the DC source 94 and depending upon direction of the current establishes either anodal-spinal down-regulate mode or the opposite up-regulate mode, and illuminates either a down-regulate indicator 96 or an up-regulate indicator 98 for the reverse. Controller 90 has memory 91 and communications link 99. Meters 15/17 provide an indication of electrical power supplied in stimulation. The controller component 90 is further configured to initiate stimulation, initiation of stimulation determined by whether the sensed value is less than or exceeds a predetermined value denoting the specific state. The controller component being also configured to provide peripheral direct current stimulation and spinal direct current stimulation for a predetermined time period and repeat stimulation a predetermined number of times over a predetermined number of days. The predetermined time period, the predetermined number of times and the predetermined number of days can be selected to regulate biological activity including at least one of protein expression level and cell behavior to promote at least one of proliferation, differentiation, migration and expression.

Although the above described embodiments illustrate a pair of electrodes being applied by each stimulation components, embodiments in which a plurality of pair of electrodes are applied with one stimulation component are also within the scope of these teachings. For example, in some embodiments, a plurality of pair of electrodes are applied with the first stimulation component, where one of each pair of electrodes is applied to a different spinal or cranial location.

While these teachings have been described in terms of specific embodiments, it is evident in view of the foregoing description that numerous alternatives, modifications and variations will be apparent to those skilled in the art. Accordingly, these teachings are intended to encompass all such alternatives, modifications and variations which fall within the scope and spirit of the present teachings and the following claims.

EXAMPLES

Example 1: Materials and Methods

Animals

Adult female CD-1 mice (n=120 weight, 27-37 g) were used for all of the animal studies performed. A total of 51 animals were used for the long-term stimulation studies that included four groups. Animals with SCI were randomly divided into three groups: a-tsDCS-treated group (n=16), a c-tsDCS-treated group (n=15), and a sham-treated group (n=10), and a non-injured control group (n=10). Subgroups of these animals were also used to study long-term changes in expression for KCC2, pKCC2, NKCC1, and pNKCC1. Injured animals with spasticity were used to test the immediate effect of tsDCS on rate-dependent depression (RDD)

(n=6), while the relatively short-term effects of tsDCS on the expression of NKCC1 and pNKCC1 were studied in non-injured animals (n=10). Pharmacological studies involving bumetanide (NKCC1 blocker) were conducted with SCI animals (n=9) and non-injured control animals (n=3). Meanwhile, qPCR studies were conducted with non-injured control animals (n=41). All of the study protocols were approved by the College of Staten Island IACUC committee.

Spinal Cord Contusion Injury

Following administration of a ketamine/xylazine cocktail (90/10 mg/kg, i.p.) to achieve deep anesthesia, a laminectomy at thoracic T10 vertebra was performed to expose the T13 spinal segment. An infinite horizon (IH) spinal cord impactor (IH-0400, Precision Systems & Instrumentation, VA, USA) was used to induce a contusive SCI force. The impact force level was 60 kdyn and was selected based on data collected from exploratory experiments that were conducted with this impactor. In these preliminary studies, contusion injuries were induced with increasing impact forces in order to optimize the SCI contusion force needed to produce spastic mice. Mice impacted at 60 kdyn produced ideal spastic behavior at approximately 2-3 weeks post-injury. Impact was applied by using a standard mouse tip (diameter=1.3 mm). Following the contusion procedure, overlying muscles and skin were sutured and the surgical site was covered with a layer of gentamicin sulfate ointment to prevent infection. Each mouse subsequently received a number and then was placed on a warming pad (30° C.) for recovery.

Stretch Apparatus

A computer-controlled stretch device was assembled in our laboratory from a stepper motor (DMX-UMD-23m, ARCUS Technology Inc., CA. USA), a foot presser mounted on a force-displacement transducer (FT03, GRASS Technologies/NATUS, CA, USA) connected to a bridge amplifier (ADInstruments, Colorado Springs, CO, USA), and a mouse holder (FIG. 1). The transducer was permanently fixed to a linear rail-guided carriage (SGB15NUU, ZNT Automatic Technology Co, Zhejiang, China). The rotational movement of the stepper motor is converted into linear displacement at the carriage by using a set of jointed flat-aluminum rods that are connected with swivel hub bearings. Two computer software programs were utilized to control the stepper motor and to perform the online (during) stretch and electromyogram (EMG) recordings. First, a stepper motor control software (DMX-UMD GUI, ARCUS Technology Inc.) was re-written to permit the execution of three consecutively timed stretches, with each stretch separated by two 10-s recovery intervals. The stepper motor was also programmed to provide three different stretch speeds: 18/s, 180/s, and 1800/s, which correspond to 3 RPM, 30 RPM, and 300 RPM, respectively. The second software package used was LabChart-7 bundled with PowerLab data acquisition system software (ADInstruments) which was used to gather and analyze data.

Mouse Holder

A mouse restraining system was fabricated in our laboratory (FIG. 1) from three components. 1) A clear Plexiglas acrylic tube served as the mouse holding chamber. 2) An internally adjustable support system made of a clear acrylic concave stabilization plate. The location of the plate was able to be adjusted linearly along the length of the chamber via a handle that protruded through a cutout that ran the entire length of the tube. In addition, the concave surface of the plate was designed to contour to the back of the animal, thereby securing it dorsally. This surface could also be adjusted externally to accommodate various sizes of mice. 3) Four over-skin stimulating electrodes with each composed of a wick-covered 1 cm×1.5 cm stainless-steel plate. One of the electrodes was permanently fixed to the floor of the holding chamber (for the abdominal reference electrode), while a second electrode was permanently fixed to the middle of the stabilization plate (for the dorsal active spinal electrode) and the location of this plate could be adjusted. The remaining two electrodes could be adjusted linearly by sliding them along cutouts present on the long sides of the stabilization plate, and these served as left and right sciatic nerve conductors, respectively. The abdominal surface of the holding chamber had two openings, one for each of the animal's hind limbs. Each opening was equipped with a knee stabilizer pad to ensure full knee extension during testing. Prior to testing, a cap with an opening in the center was placed on the anterior end of the holding chamber for breathing and for isoflurane administration. To limit hind limb movement to the ankle joint during stretching, another acrylic stand was created to secure the distal leg. The stand had an adjustable stainless steel ankle stabilizer clamp that could be moved in the x, y, and z axes to achieve proper alignment of the foot under the presser, and to adjust the hip angle of the animal before stretching.

Circuit and Power Source

Passing current to peripheral nerves is required to attenuate muscle tone (Ahmed, 2014). Moreover, the direction and distribution of this current can be regulated (Ahmed. 2017). The tsDCS protocols of the present study required a modification of the trans-spinal circuit that was originally designed in our laboratory to be used with anesthetized animals (Ahmed, 2014). Briefly, the circuit was modified to noninvasively pass direct current (DC) to the spinal cord and the sciatic nerve of the most affected limb by using over-skin electrodes. To prevent evoking nerve activity, the current passing into the sciatic nerve electrode was attenuated by dividing the reference source into two branches: the first branch connected directly to the abdominal electrode and carried un-attenuated current, while the second branch passed through a 300 KO resistor to attenuate current to the sciatic nerve. Current was supplied by a GRASS stimulator with a dedicated DC unit (S88, GRASS Technologies/NATUS). By switching the polarity of the current source, this circuit design could provide instant reversal of the current direction from anodal to cathodal, and vice versa. The circuit design was also effective in attenuating sciatic nerve current. For example. For each 1.5 mA that passed through the spinal-abdominal electrodes, 300 pA passed through the sciatic nerve circuit. Monitoring of current parameters and verification of DC attenuation was performed at the beginning, during, and upon completion of each experiment by using a bench-top digital multi-meter (34401A, Agilent/Keysight Technologies, CA USA).

Repeated-Session tsDCS (Long-Term) Procedure

One week before treatment, all of the animals underwent initial baseline testing and the following data were recorded: the peak resistances at three different stretch speeds, concurrent EMG activity, and skill and ground locomotion testing. To apply stimulation, nine mouse holders were fabricated to provide tsDCS to multiple animals simultaneously. Animals in the anodal and cathodal groups received 20-min tsDCS (1.5 mA) treatments daily for 7 d. Animals in the sham-treated group were treated in parallel, although they did not receive tsDCS intervention. Meanwhile, the intact control group was only exposed to the testing procedure. Animals were reevaluated immediately after the 7-d tsDCS treatment period, then also two weeks and four weeks post-treatment. After the last evaluation, the animals were tested for RDD of the Hoffman reflex.

Ground Locomotion Testing

The DigiGait system (Mouse Specifics Inc, Framingham, MA, USA) was used to quantify locomotor recovery following SCI and tsDCS treatment. All of the groups were tested four times with the DigiGait system: before, immediately after, and two and three weeks after tsDCS intervention. The control group was tested twice with a two week interval between the tests.

During testing, a minimum of 20 steps were collected at two speeds: 10 cm/s and 20 cm/s. Three parameters were considered to be sensitive to spasticity in the triceps surae muscle during locomotion: peak area and rising and falling slopes of the paw area. Peak paw area was calculated based on the maximum contact area of the foot of the mouse with the DigiGait treadmill belt. Rising slope was considered an indicator of the speed of transition during the first half of the stance phase of the mouse locomotion cycle, while falling slope was considered an indicator of the speed of transition during the second half of the stance phase of the mouse locomotor cycle. The stance phase is the segment of the locomotion cycle when a mouse's paw is in contact with the treadmill belt.

Skill-Locomotion Testing

A ladder-wheel was assembled in our laboratory from a stepper motor, a driver, and a controller (DMX-UMD-23, ARCUS Technology Inc.). The speed and direction of the wheel was controlled with custom-written software. The wheel was made from Plexiglas to allow side visualization and the spaces between the rungs were variable to prevent learning. A camera was placed on the underside of each animal to record foot faults. Animals were tested prior to stimulation and once a week for three weeks after the stimulation ended. For each recorded session, a continuous 90 s video was analyzed frame-by-frame according to a previously described foot fault scoring system (Farr et al., 2006: Metz and Whishaw, 2002; Metz and Whishaw, 2009) (Table 1). A score for each of the animal's hind limbs was calculated for each criteria by multiplying the total number of foot faults by the corresponding score for each criterion according to Table 1. Scores for all of the criteria were subsequently added to obtain a total score for each of the hind limbs.

RDD of the Hoffman Reflex

After the last evaluation, the mice were anesthetized with a mixture of ketamine and xylazine (90 mg/kg). The animals were then shaved at the hind limb and pelvic area and two sets of recording electrodes were applied to record EMG, heart rate, and breathing activity. Stimulation of the tibial nerve was achieved by using a concentric needle-stimulating electrode. After positioning the animal on the recording station, heart rate (HR) and respiratory rate (RR) were monitored online. When an animal was deeply anesthetized, both their HR and RR were generally faster, while their respiration was shallower. At this level of anesthesia, reflexes were difficult to evoke. Moreover, if reflexes were evoked, the RDD was very high, even in the animals that expressed severe spasticity. Therefore, in the exploratory experiments that were performed, the procedure was standardized by monitoring the relationship between both HR and RR and the levels of awareness of the animal and RDD. For example, as the animals awaken their HR becomes regular at 2 Hz and then it becomes more irregular between 2 Hz and 4 Hz, while the r RR becomes deeper and slower. When an irregular HR and deeper RR phase were first observed, the RDD protocol was started. It consisted of five trains of five pulses. The frequencies of the trains were: 0.1 Hz, 0.5 Hz, 1 Hz, 2 Hz, and 5 Hz. The waiting intervals between the trains were 1-min long. Testing was performed on both hind limbs. Stimulation intensity was gradually increased until maximum H-wave relative to M-wave was observed, followed by the RDD protocol. Data were collected by using the PowerLab system (ADInstruments), recorded at a sample rate of 10 KHz, and LabChart software (ADInstruments). Peaks of the averaged H-wave were measured and percent of change was calculated relative to baseline values. RDD was calculated as the percentage reduction based on the difference calculated between the H-wave amplitude induced by the fifth pulse and the first pulse in a train divided by the −1 to inverse the values.

Western Blot

Spinal cord tissues were collected and immediately placed in dry ice. The samples were subsequently homogenized in RIPA buffer (Cat. #: BP-115, Boston Bio Products, Ashland, MA, USA) containing a Protease Inhibitor Cocktail (SC-29131, Santa Cruz Biotechnology Dallas Tex., U.S.A.), Phosphatase Inhibitors Cocktail 11 (Cat. #: BP-480, Boston Bio Products), 100 mM PMSF (Cat. #: BP-481, Boston Bio Products), and 500 mM EDTA. Following the addition of RIPA cocktail to each sample (100 mg/ml), the lysates were incubated on ice for 15 min before being sonicated for 0.5-1 min to achieve complete homogenization using Sonic Dismembrator (Fisher Scientific Springfield Township, NJ USA). The samples were then centrifuged at 13000 rpm in a Sorvall Legend Micro 21R Centrifuge for 30 min to collect the supernatant fraction of each sample. Total protein concentrations were determined by using an iMark™ Microplate Absorbance Reader (Bio-Rad, Hercules Calif.). Twenty micrograms of each sample were mixed with an equal volume of 2× sample buffer and electrophoresed on 10% SDS polyacrylamide gels. After the separated proteins were transferred to PVDF membranes (Bio-Rad), the membranes were blocked in 5% skim milk buffer for 2 h, then were incubated at 4° C. with the appropriate primary antibodies overnight. The primary antibodies used included: rabbit polyclonal heat shock protein 70 (HSP70)/HSC-70 (H-300) antibody (1:1000; SC-33575, Santa Cruz Biotechnology); anti-KCC2 antibody (1:1000; ab49917, Abcam Inc Cambridge. Mass. USA); rabbit polyclonal Anti-Phosoho-Ser940 Potassium Chloride Cotransporter (KCC2) antibody (1:1000; p 1551-940, PhosphoSolutions Aurora, CO USA); mouse monoclonal NKCC1 (A-6) antibody (1:1000; SC-514774. Santa Cruz Biotechnology); and rabbit polyclonal Anti-Phospho NKCC1 Thr212/Thr217 antibody (1:1000; ABS 1004, EMD Millipore, Burlington, MA, USA). The membranes were subsequently washed 3× with 1×TTBS and incubated with appropriate secondary antibodies in blocking buffer. The secondary antibodies included: goat anti-rabbit IgG-horseradish peroxidase (HRP) antibody (1:5000; SC-2004, Santa Cruz Biotechnology) and goat anti-mouse IgG-HRP antibody (1:5000; SC-2005, Santa Cruz Biotechnology). After 1 h at room temperature. The membranes were washed 3× with 1×TTBS. Bound antibodies were visualized with Luminol/Oxidizing solution, an HRP-based Chemiluminescent Substrate (Boston Bio Product) and quantified with Image J software (ImageJ, U. S. National Institutes of Health. Bethesda, Maryland, USA). The blots were subsequently incubated with 1× stripping buffer, 1× phosphate-buffered saline (PBS), and 1×TTBS for 30 min, then were incubated in blocking buffer for 1 h. After an additional incubation with mouse monoclonal IgG (i-actin (C4) HRP antibody (1:2500; SC-47778, Santa Cruz Biotechnology) in blocking buffer for 1 h, the blots were washed 3× with 1×TTBS and then were imaged with Luminal/Oxidizing solution (Boston Bio Product). Bands were quantified with Image J software.

Immunohistochemistry

HSP 70 Immunohistochemistry: To examine HSP70 expression in motor neurons following anodal and cathodal stimulation, animals were anesthetized with a ketamine/xylazine solution and then perfused with PBS at room temperature, followed by 4% paraformaldehyde. Dissected spinal cord segments were post-fixed overnight in the same fixative and then were transferred to 30% sucrose for cryoprotection. The spinal cord segments were frozen with dry ice, sectioned, and collected in Phosphate Buffer Saline (PBS). After three washes in Tris A buffer, the sections were washed 1× with Tris B for 15 min and then were blocked in 10% Normal Goat Serum (NGS) diluted in Tris B. After 1 h, primary mouse monoclonal HSP70 (F-3) antibody was added (1:500, sc-373867, Santa Cruz Biotechnology) and the sections were incubated overnight on a shaker at 4 C. The next day, the sections were washed 3× and then were incubated with a biotinylated goat anti-mouse antibody (1:500: BA-9200, Vector Laboratories Burlingame, CA USA). After 1 h, DyLight 488 (1:2000: SA-5488, Vector Laboratories) was added. After another 30 min, the sections were washed 2× with Tris A before the slices were mounted with medium containing DAPI (H-1200: Vector Laboratories).

Choline acetyltransferase (ChAT) Immunohistochemistry: Spinal cord sections were washed 3× with PBS before being incubated with 10% rabbit serum/0.1'Y° Triton X-100/0.1 M PBS for 1 h at room temperature. The sections were then incubated with an anti-ChAT primary antibody (1:500, AB144P, EMD Millipore Corp.) in 0.1% Triton X-100/0.1 M PBS for 48-72 h at 4 C. The sections were thoroughly washed 3× with PBS and then were incubated with rabbit anti-goat 568 nm antibodies (1:500) in 0.1% Triton X-100/0.1 M PBS for 1 h at room temperature. After an additional three washes with PBS, the sections were mounted with medium containing DAPI (H-1200; Vector Laboratories).

q-PCR

RNA was isolated from spinal cord samples by using a Trizol-based method (Rio et al., 2010), followed by extraction with chloroform and isopropyl alcohol. Briefly, each RNA sample was dissolved in diethyl dicarbonate (DEPC) water and then purified with a Qiagen RNAeasy kit (Qiagen, Hilden Germany), according to the manufacturer's instructions. RNA concentrations were measured with a Nanodrop 2000c instrument (Thermofisher Scientific, Waltham, MA, USA). Total RNA was converted to complementary DNA (cDNA) with the iScript™ Reverse Transcription Supermix (Bio-Rad, Hercules, CA, USA). For each reaction, 2 pg of total RNA was combined with gene specific primers (PrimePCR Assay Slc12a2). Samples that were obtained from stimulated and unstimulated animals were always assayed on the same plate. For each sample, amplified product differences for each transcript were measured from three replicates by using SYBR Green chemistry-based detection. Beta-actin (ACTB), TATA box binding protein (TBP), and hypoxanthine phosphoribosyltransferase 1 (HPRT1) were used as endogenous reference genes, and the primers used for amplification of these genes were PrimePCR Assay ACTB, PrimePCR Assay TBP, and PrimePCR Assay HPRT1, respectively. The resulting three transcripts were selected for analysis based on a previous demonstration of their stable expression in the central nervous system (Valente et al., 2014; Walder et al., 2014). The total reaction volume was 10 μl and it included: 5 μl of the supermix, primers, cDNA template, and nuclease-free water. The qPCR reactions were carried out in 384-well plates with the CFX384 Real Time System (Bio-Rad) and SsoADVANCED Universal SYBR Green Supermix (Bio-Rad). CFX manager software (Hercules, CA USA) was used with automatic baseline and threshold detection options selected. The resulting data were exported to Microsoft Excel and relative normalized expression was calculated for each sample by using the geometric mean of the triplicates against the endogenous reference genes as a normalization factor.

Experimental Design and Statistical Analysis

Based on exploratory experiments that were performed, the ankle was stretched from an initial angle of 109° plantarflexion to 81° dorsiflexion (stretched by 28°) to induce a stretch reflex without damaging the muscle. The corresponding knee joint angle was at full extension and this was consistently maintained across all of the measurements. For each stretch parameter that was tested using the apparatus, two sets of data were collected: one set of data were collected while the animal was awake, and a second set of data were collected while the animal was under full isoflurane anesthesia. Data were collected while the animal was anesthetized in order to represent the passive resistive forces of muscles and connective tissues. To isolate the neuronal-produced component of stretch resistance from that caused by passive tissues, the value of the tested parameter collected during anesthesia was subtracted from the value collected while the animal was awake. This method ensured that only the neuronal contribution of the stretch response would be analyzed. Subtraction of the tail-pinch and pedal reflexes were used to standardize the anesthesia level at which the stretches were performed. However, isoflurane anesthesia did not completely remove the reflex response during the higher speed stretches. The following stretch parameters were collected: active resistance peak amplitude and active slope and root mean square EMG (RMS EMG) area and amplitude (FIG. 1). Active peak resistance was calculated as the height of the resistance trace relative to baseline (before the stretch). Active slope was calculated based on the first derivative of the rising phase of the muscle resistance in response to stretching. RMS EMG amplitude was calculated based on the height of the EMG trace relative to baseline. RMS EMG area was calculated based on area under the curve.

Four investigators transferred the stretch apparatus data collected in LabChart software to Excel sheets and calculated the scores for each animal using embedded Excel sheet formulas. One investigator analyzed the DigiGait (locomotion) and ladder wheel (skilled locomotion) videos, while another investigator analyzed the data with embedded Excel sheet formulas to calculate animal scores. All six investigators were blinded to the study hypothesis. RMS equations were embedded in LabChart with a window of 0.5 ms to generate the RMS for EMG.

To study the effects of repeated tsDCS on muscle tone, a mixed factorial repeated measures experimental design was used in which treatment (cathode, anode, or sham) was the between-subjects independent variable, and time and speed were the within—subjects independent variables. Mixed factorial ANOVA (split-plot ANOVA) was used to assess differences in peak resistance, slopes. EMG amplitude, and area among the groups. Bonferroni confidence interval adjustment was also applied. Mixed factorial ANOVA was used to analyze the RDD data. Between groups comparison was performed using Tukey's post-hoc test, One-way repeated measures ANOVA (RM ANOVA) was used to analyze paw area and the rising and falling slopes in ground locomotion data. All assumptions for use of repeated-measures ANOVA were fulfilled. Holm-Sidak post-hoc correction was used to test differences between speeds for the stretch responses and skill locomotion. The two-tailed paired t-test was used to analyze the difference in skilled locomotion between the two evaluations of the control groups. SPSS software was used to perform all of the statistical tests (IBM Statistics, SPSS version 23). To test for sphericity, Mauchly's test in SPSS was applied (p>0.05). The critical level of significance was set at p<0.05. Data are presented as the mean±standard error of the mean (SEM).

Long-Term Effects of DCS on Spasticity Outcome Measures

Differences in the amplitudes of active muscle resistance were assessed by using mixed factorial ANOVA, with time (4 levels: pre, E1 E2, and E3) and speed (3 levels: speeds 1, 2, and 3) being within-subjects variables, and treatment (three levels: anode, cathode, and sham) being a between-subjects variable. No significant interaction between treatment and speed was observed (F=0.4, p=0.81). In contrast, a significant interaction between treatment and time of evaluation was observed (F=2.36, p=0.03). After adjustment for multiple comparisons (Bonferroni), a significant marginal mean difference between the anode- and cathode-treated animals was identified (p<0.001), as well as between the anode- and sham-treated groups (p<0.001). However, there was no significant difference between the cathode- and sham-treated groups (p=0.13) during E2, E3, and E4. There was also no significance difference between the anode-, cathode-, and sham-treated animals at E1 (p>0.05). As shown in FIG. 2, a within-groups analysis showed that animals treated with anodal tsDCS exhibited significant reductions in the amplitude of active muscle resistance_ The mean scores at the different time intervals versus the pre-treatment score according to speed were significant: speed 1 (E1, p<0.001; E2, p=0.003; E3, p=0.002), speed 2 (E1, p<0.001: E2, p=0.038; E3, p=0.027), and speed 3 (E1, p<0.001; E2, p=0.004; E3, p=0.046), each according to the Holm-Sidak method.

Figure 2A:
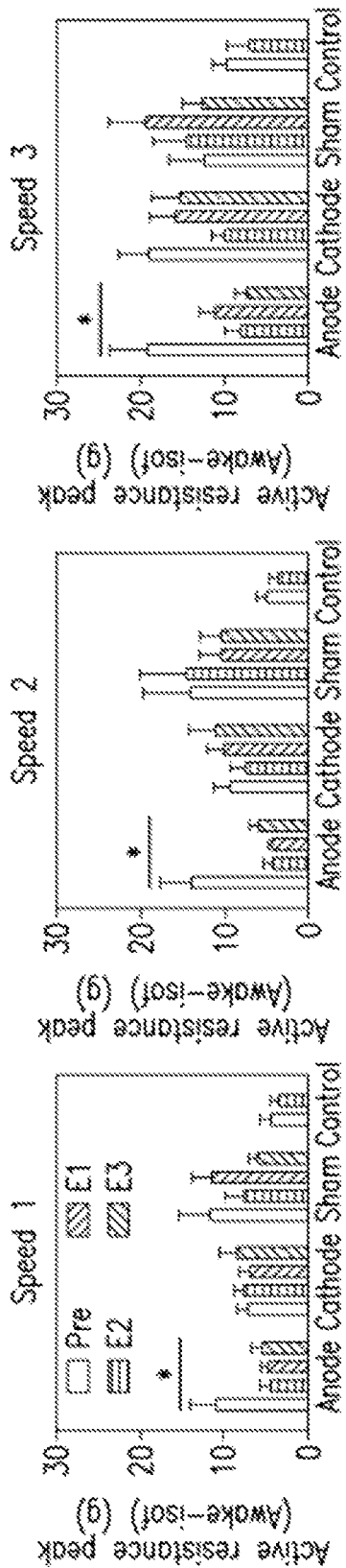
FIGS. 2A-2D represent repeated treatment with anodal tsDCS results in long-term reduction of spasticity in mice with SCI. Animals were divided into four groups: an anodal-tsDCS group (n=16); a cathodal-tsDCS group (n=15); a sham-treated group (n=10), and an intact control group (n=8). A-C, Anodal tsDCS caused a significant reduction in peak muscle resistance (FIG. 2A), rising slope (FIG. 2B), EMG area (FIG. 2C), and EMG amplitude (FIG. 2D). For FIGS. 2B-2D, cathodal and sham treatments did not significantly differ. "$p<0.05$, Holm-Sidak method. Data are presented as mean±SEM.
Figure 2B:
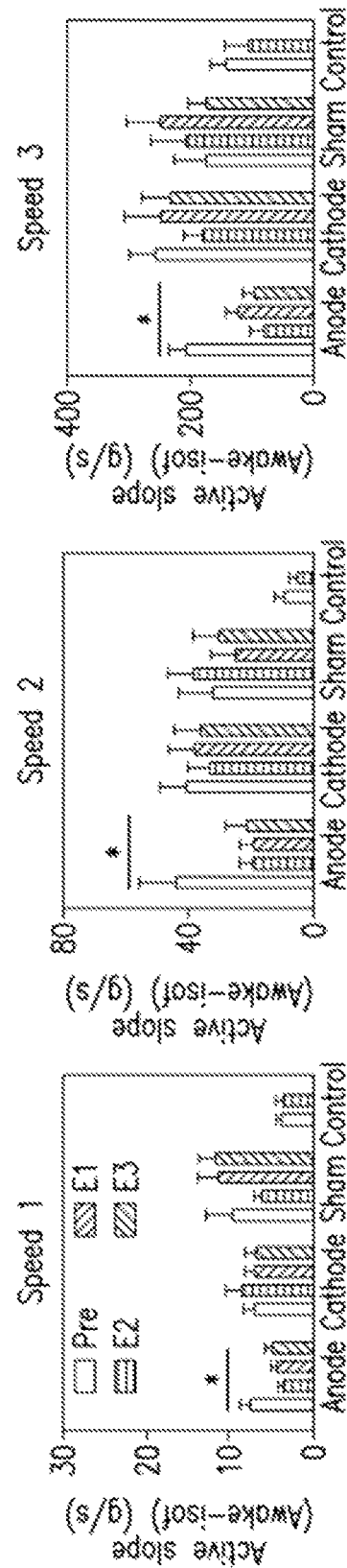
Figure 2C:
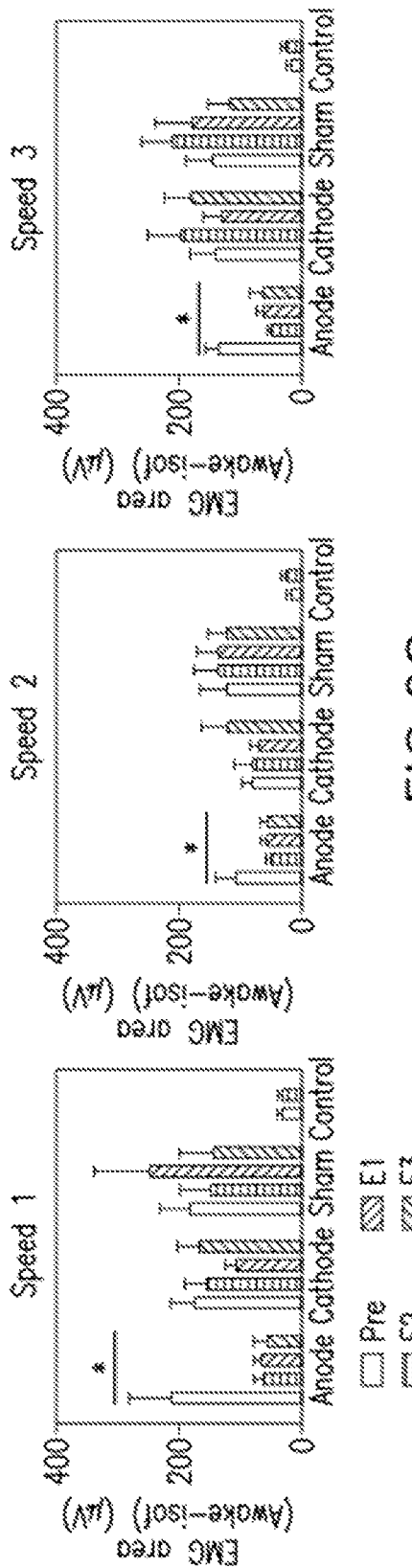
Figure 2D:
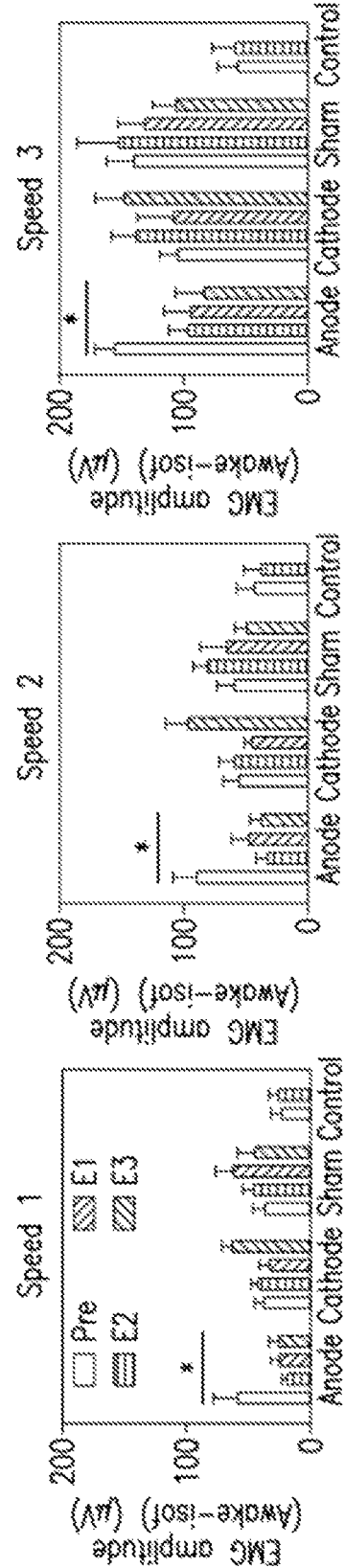
Figure 3A:
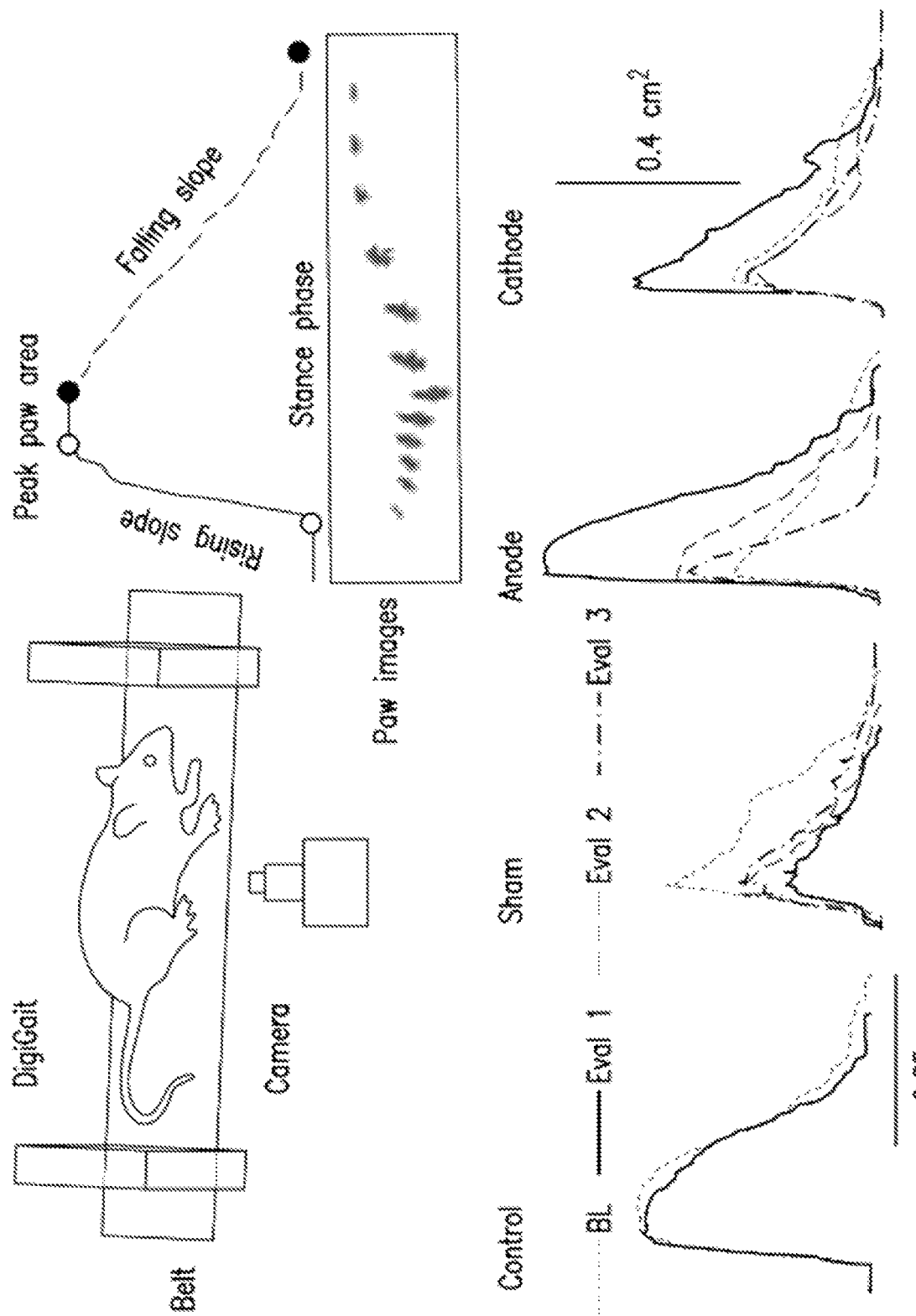
FIGS. 3A-3E depict repeated treatment with anodal tsDCS leads to changes in locomotion patterns.
Figure 3B:
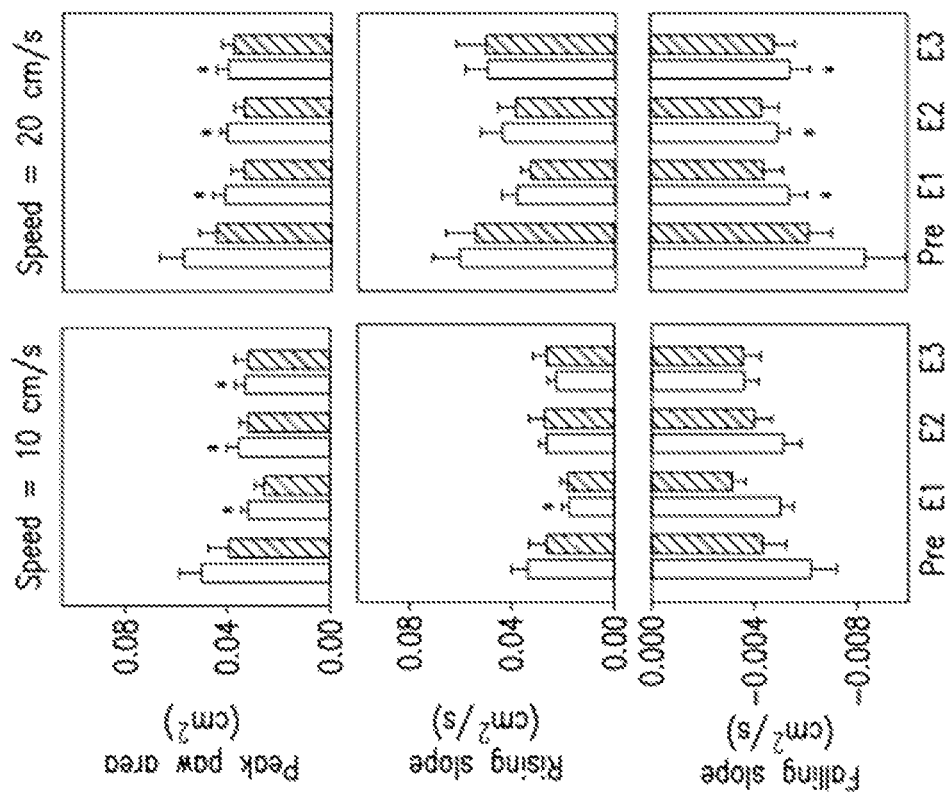
Figure 3C:
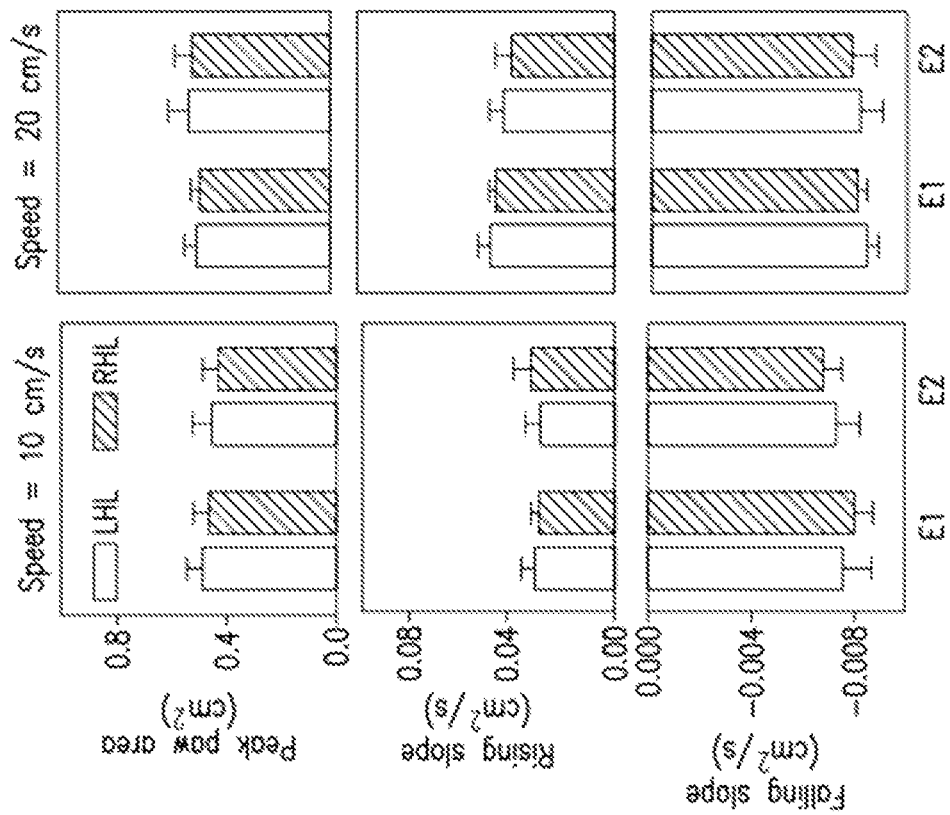
Figure 3D:
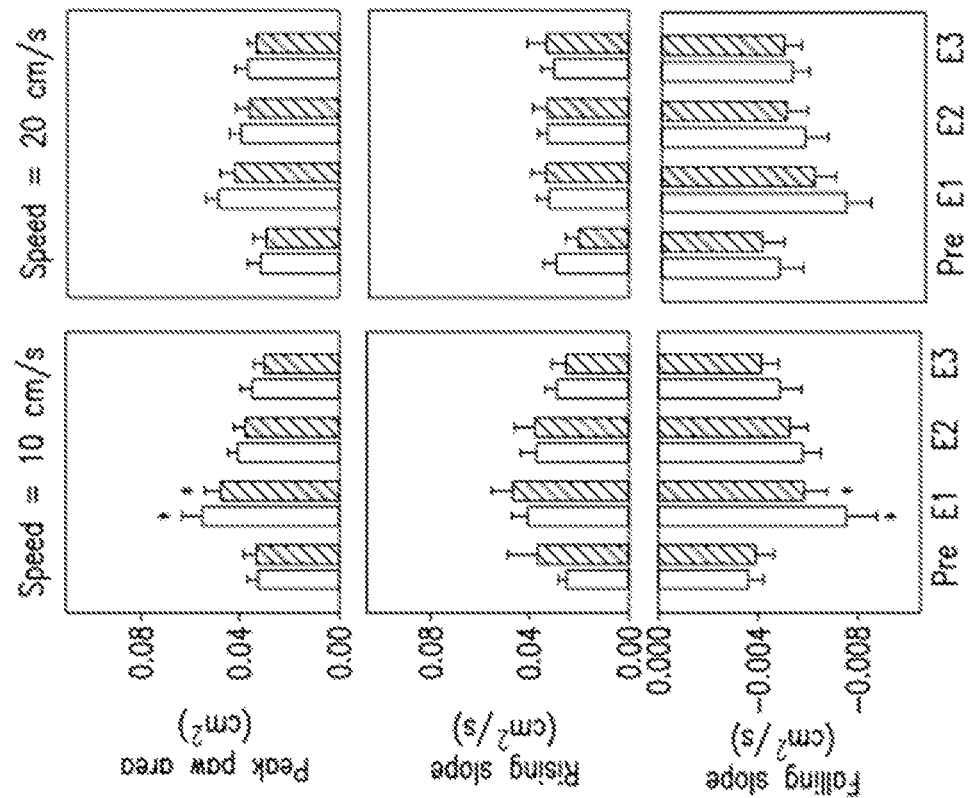
Figure 3E:
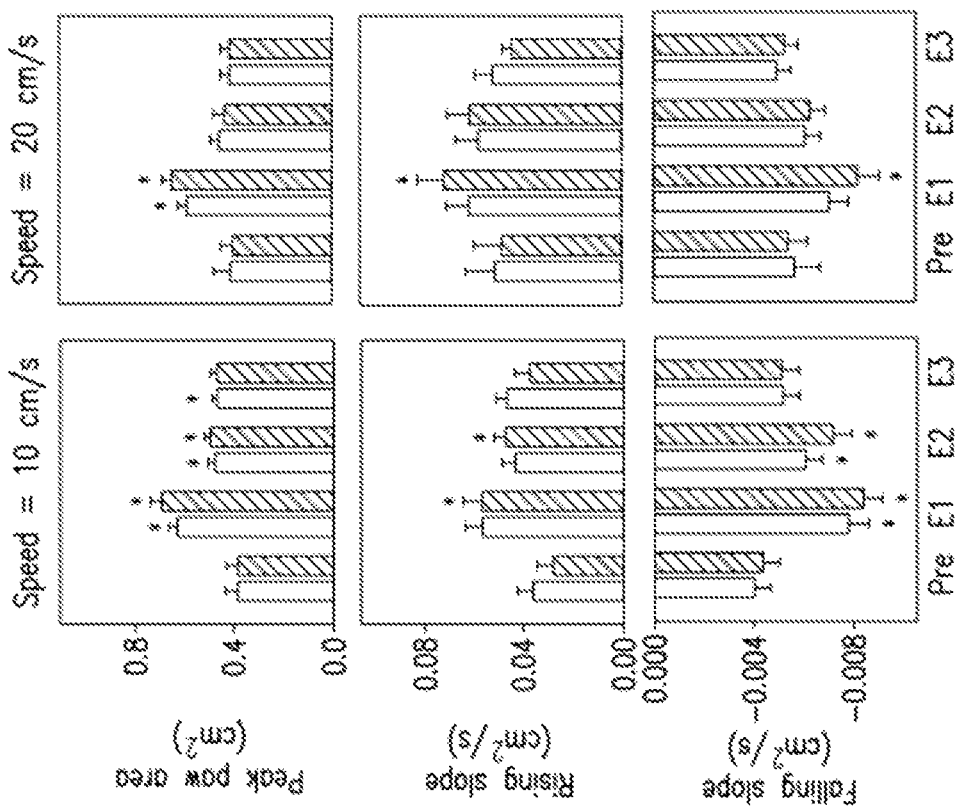

Differences in active slope were assessed by using mixed factorial ANOVA (FIG. 2B). The analysis showed significant interactions between time and treatments (F=3.59, p=0.03), yet no interaction between speed and treatments (F=1.02, p=0.41). Between-group analysis further showed significant differences between the anode- and cathode-treated groups (p=0.015), and between the anode-treated and sham-treated groups (p=0.04), during E2. E3, and E4. However, there was no difference between the sham-treated and cathode-treated animals (p=0.829). A within-subjects analysis also revealed that the anode-treated group underwent a decrease in active slope over time (p<0.01), and this was not observed for the other groups (p>0.05). The difference in EMG area was assessed by using mixed factorial ANOVA (FIG. 2C).

There was a significant interaction between time and treatments (F=4.4, p=0.0002), yet no interactions between speed and treatment (F=0.6, p=0.8). There were also no interactions between time, speed, and treatments (F=1.1, p=0.34). A post-hoc analysis identified a significant difference between the anode-treated and cathode-treated groups (p=0.001), and between the anode-treated and sham-treated groups (p=0.0001). In contrast, there was no difference between the cathode-treated and sham-treated groups (p=0.34). A within-subjects analysis further revealed that the anode-treated group exhibited a decrease in EMG area over time (p<0.01), and this was not observed for the other groups (p>0.05).

The difference in EMG amplitude (awake minus isoflurane) was assessed by using mixed factorial ANOVA (rig. 2D). A significant interaction was observed between time and treatments (F=3.63, p=0.007). Meanwhile there was no interaction between speed and treatments (F=0.61, p=0.66), nor between speed, time, and treatments (F=0.19, p=0.9). A post-hoc analysis identified a significant difference between the anode-treated and cathode-treated groups (p<0.001), and between the anode-treated and sham-treated animals (p=0.001). In contrast, there was no difference between the cathode-treated and sham-treated animals (p=0.96). A within-subjects analysis further identified that the anode-treated group exhibited a decrease in EMG amplitude over time (p<0.01), and this was not observed for the other groups (p>0.05).

Repeated Treatment of Anodal tsDCS Changes Ground Locomotion Patterns

Locomotor characteristics were investigated by using the DigiGait system (FIG. 3). Animals were assessed at two speeds, 10 cm/s and 20 cm/s, prior to injury (pre), and then at three intervals following treatment: immediately following treatment (E1) and at 2 weeks (E2) and 4 weeks (E3) following treatment. Three relevant parameters were analyzed at each of these time points: rising slope, peak paw area, and falling slope. The control animals showed no difference in paw area, rising slope, or falling slope between the two evaluations that were performed for each of the two hind limbs (p>0.05: two-tailed paired t-test). In contrast, the sham-treated animals exhibited significant decreases in paw area for the left hind leg (LHL), yet not for the right hind leg (RHL), at the slower speed during the E1-E3 evaluations (RM ANOVA, F=4.75, p=0.009). At the faster speed, paw area significantly decreased at all of the evaluations (E1-E3) for the LHL (RM ANOVA, F=5.54, p=0.005), while paw area did not significantly change for the RHL. Rising slope significantly decreased during E1 at the slow speed for the LHL (RM ANOVA, F=3.20, p=0.039), and not for the RHL. In contrast, rising slope did not change significantly at the faster speed for both hind limbs. Similarly, falling slope did not significantly decrease for either hind limb at the slow speed, yet it significantly decreased during all of the evaluation points at the faster speed for the LHL (RM ANOVA, F=4.47, p=0.012), but not for the RHL (*p<0.05, Holm-Sidak method). Anodal tsDCS-treated animals exhibited a significant increase in paw area for the LHL during all of the evaluations at slow speed (E1-E3), and only during E1 and E2 for the (repeated measures (RM) ANOVA for LHL: F=12.70, p<0.001; RM ANOVA for RHL: F=17.32, p<0.001). Paw area also significantly increased during E1 at the faster speed for both the LHL (RM ANOVA, F=7.04, p<0.001) and the RHL (RM ANOVA, F=13.32, p<0.001). Rising slope significantly increased at the slow speed during E1 and E2 for the RHL (RM ANOVA, F=6.06, p=0.002), but not for the LHL. Meanwhile, at the faster speed, rising slope only significantly increased during E1 for the RHL (RM ANOVA, F=4.19, p=0.011). Falling slope significantly increased during E1 and E2 at the slow speed for both the LHL (RM ANOVA, F=10.03, p<0.001) and the RHL (RM ANOVA. F=13.48, p<0.001). Meanwhile, falling slope significantly increased during E1 at the faster speed only for the RHL (RM ANOVA, F=9.06, p<0.001) (*p<0.05, Holm-Sidak method). In the cathodal tsDCS-treated animals, a significant increase in paw area was observed during E1 at the slow speed compared to baseline (RM ANOVA for LHL: F=7.92, p<0.001; RM ANOVA for RHL: F=8.46, p<0.001), while no change in paw area was observed during E2 or E3. There was also no significant change in paw area at any of the evaluation points at the faster speed, while rising slope remained unchanged at both the slow speed and the faster speed. In contrast, falling slope significantly increased during E1 and E2 for the LHL (RM ANOVA for slow speed: F=6.72, p<0.001), and only during E1 for the RHL (RM ANOVA, for slow speed: F=3.47, p=0.025) (*p<0.05, Holrn-Sidak method). At the faster speed, there was no significant change in falling slope.

Anodal Treatment Enhances Recovery of Skill Locomotion

Figure 4A:
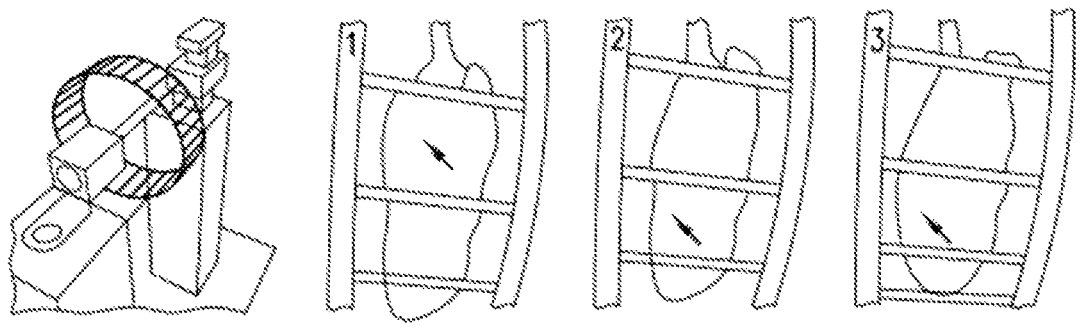
FIGS. 4A-4C exhibit the enhancement of motor control recovery following repeated anode treatment. The left part of FIG. 4A shows an image of the ladder-wheel and the right part of FIG. 4B shows consecutive frames (1-3) showing a total miss by a left hind limb.

A computer-controlled ladder wheel (FIG. 4A) was used to investigate the effect of repeated tsDCS on skill locomotion. Mixed, two-way repeated measures ANOVA (variables: time and limb side) was applied to assess improvements in skill locomotion. Significant differences in skill locomotion were observed across the four time points examined in the anode-treated group (F=6.49, p=0.002). The RHL of the anode-treated group had a significantly higher mean score during E2 compared to E1 (p=0.001, Bonferroni), while the LHL had a significantly higher score during E2 and E3 compared to E1 (p<0.01, Bonferroni) (FIG. 4A). However, significant differences were not observed for any of the other groups across the four time points (p>0.05, Bonferroni).

Figure 4B:
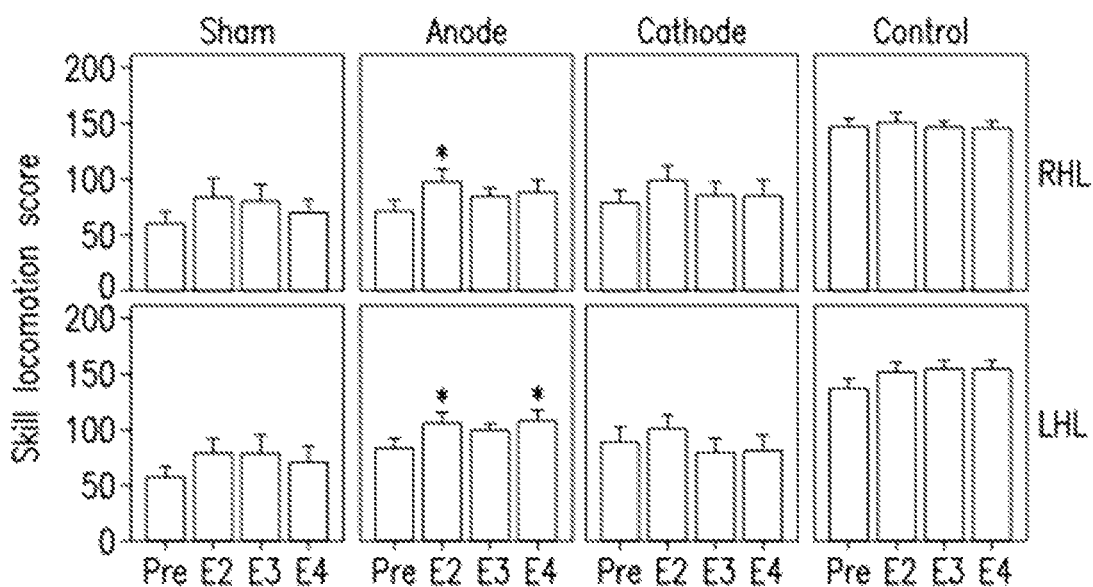

Next, the percent change (from pre-evaluation) between the groups were compared (FIG. 4B). Mixed two-way repeated measures ANOVA detected significant main effects among the groups (F=5.97, p=0.016). For example, the anode-treated group exhibited a significantly higher percent change in their scores compared to the cathode-treated group (p=0.027, Bonferroni) and the healthy group (p=0.048, Bonferroni). For the anode-treated group, a higher percent change was observed compared with the sham group, although the change was not significant (p>0.05). There were no significant differences among the other groups (p>0.05). Overall, these findings reveal that enhanced recovery of motor control of skill locomotion occurred in the animals that were treated with anodal tsDCS.

RDD of H-Reflex Following tsDCS Treatment

Mixed two-way repeated measures ANOVA was also conducted to assess changes in RDD. The treatment conditions (e.g., independent factor, 4 levels: control, sham, anode, and cathode) resulted in significant differences in the main effect among the different levels of treatment (F=3.0, p=0.038). In addition, frequency was identified as a significant main effect (within-subjects repeated factor, 5 levels: 0.1, 0.5, 1, 2, and 5 Hz), (F=13.8, p<0.001). However, there was no statistically significant interaction observed between frequency and treatment condition (F=1.35, p=0.192). Thus, the effects from different levels of treatment do not depend on what level of frequency is present.

A multiple comparison test (Tukey) was applied to identify which group(s) differ from the others. As shown in FIG. 5, the mean scores of RDD at frequencies of 1 Hz, 2 Hz, and 5 Hz were significantly higher compared to the RDD score at 0.1 Hz (5 Hz vs. 1 Hz, p<0.001:4 Hz vs. 1 Hz, p=0.006; 3 Hz vs. 1 Hz, p=0.024). Within the sham group, the mean scores of RDD at all of the frequencies did not significantly differ compared to the RDD score at 0.1 Hz (p>0.05). Within the anode-treated group, the mean scores of RDD at frequencies of 2 Hz and 5 Hz were significantly higher compared to the RDD score at 0.1 Hz (5 Hz vs. 1 Hz, p<0.001:4 Hz vs. 1 Hz, p<0.001), while the mean RDD score at 1 Hz within the cathode-treated group was significantly higher compared to the mean RDD at 0.1 Hz (p=0.017). Between-group comparisons (Tukey) were performed and significant differences in RDD scores at 5 Hz were observed. For example, the RDD score at 5 Hz was significantly higher in the anode-treated group compared to the scores for the sham- and cathode-treated groups (p<0.05). Meanwhile, the control group had a significantly higher RDD score at 5 Hz compared to the cathode-treated group (p=0.016). Overall, these findings provide support for a physiological mechanism to underlie the observed reduction in spasticity that was observed following repeated anode stimulation. In six of the animals with spasticity, the short-term effect of anodal and cathodal tsDCS on RDD was tested. An immediate and significant increase or decrease in RDD was observed during cathodal and anodal tsDCS, respectively (data not shown). These data are consistent with above reported long-term effects of tsDCS on RDD.

Figure 6A:
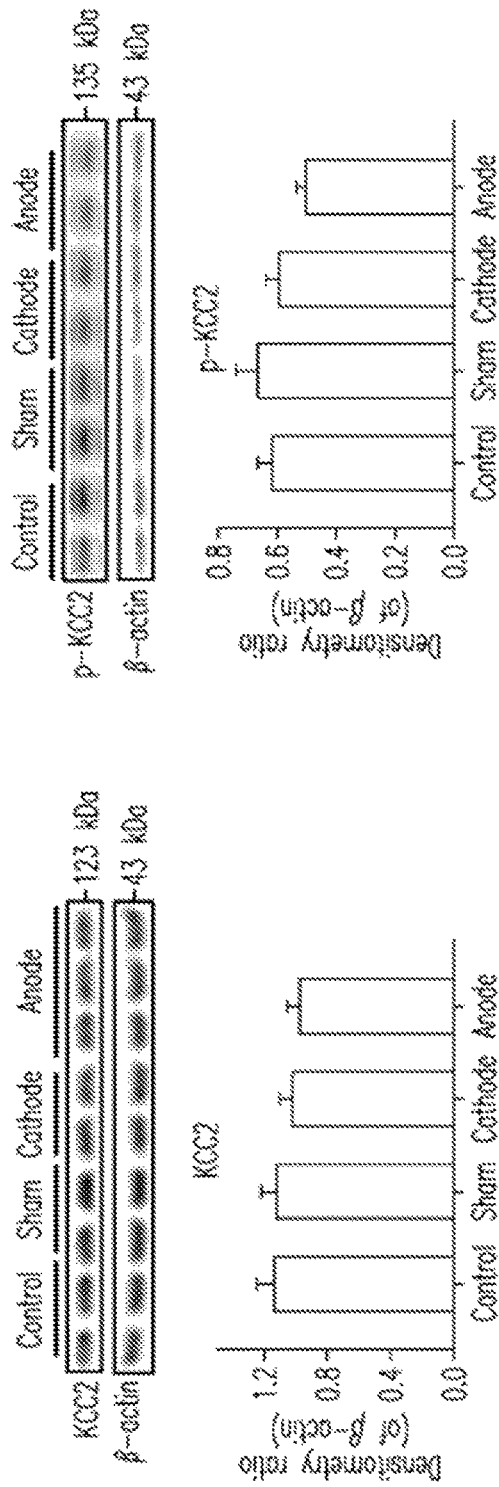
FIGS. 6A-6B show changes in expression detected for KCC2, p-KCC2, NKCC1, and p-NKCC1 following repeated tsDCS. Representative animals from the experimental groups were randomly selected to investigate these molecular changes. The left portion of FIG. 6A shows how KCC2 expression was unchanged in the sham-treated group, and was slightly reduced in the anode- and cathode-treated groups compared to the control group. The right portion of FIG. 6A shows how pKCC2 expression moderately increased in the sham-treated group and was slightly reduced in the cathode-treated and anode-treated groups compared to the control group.
Figure 6B:
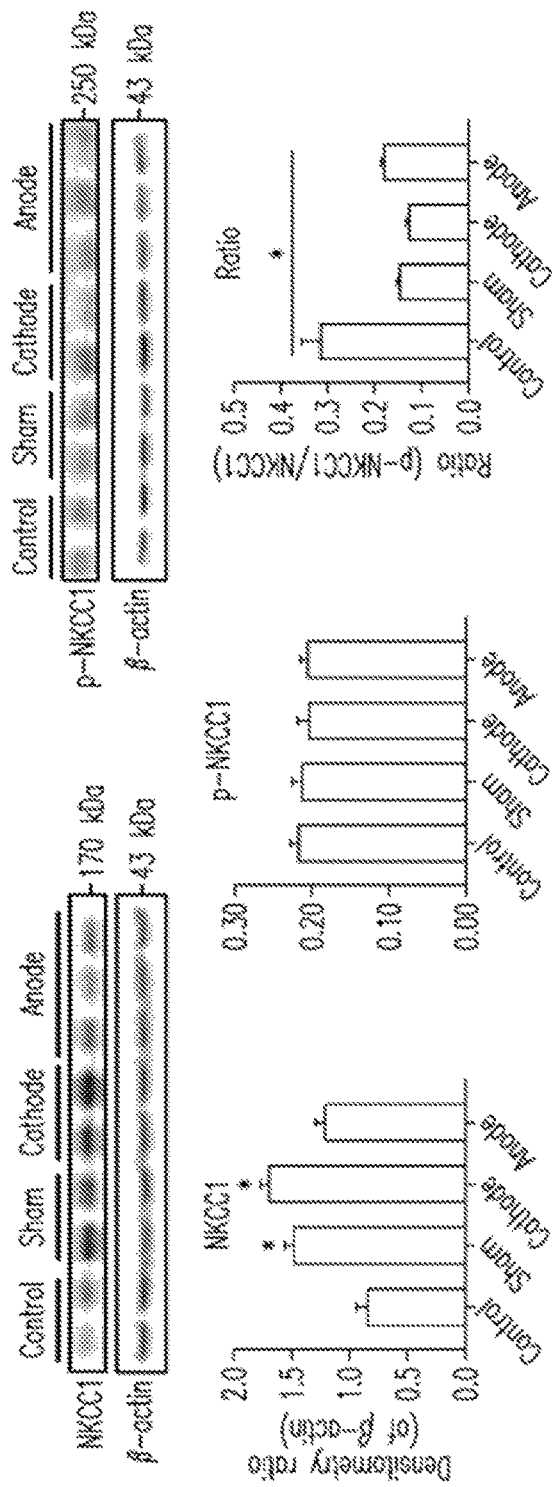

Example 2: Expression of KCC2, p-KCC2, NKCC1, and p-NKCC1 Following Repeated tsDCS Treatment Changes in KCC2 protein levels were investigated in the lumbosacral region of the spinal cord below the site of injury four weeks after the animals received 7 d of repeated tsDCS treatment. Reductions in KCC2 and pKCC2 protein levels were observed following cathodal and anodal tsDCS treatments compared to the control healthy group (FIG. 6A). However, there were no significant differences between the protein levels among the groups (p>0.05). The level of the co-transporter, NKCC1, was also examined (FIG. 6B). Kruskal-Wallis one-way ANOVA detected significant differences between the median values among the treatment groups for NKCC1 (H=31.4, p<0.001). In the control healthy animals, low levels of NKKC1 expression were detected in their lumbosacral spinal cord regions. In contrast, the levels of NKCC1 protein in the sham-treated animals with SCI and spasticity and in the cathodal-treated groups were significantly higher compared to the control group (p<0.05. Dunn's method). In the anodal-treated group, a lower level of NKCC1 protein was detected, and the difference between this level and that of the control group was not significant (p>0.05, Dunn's method).

Figure 7A:
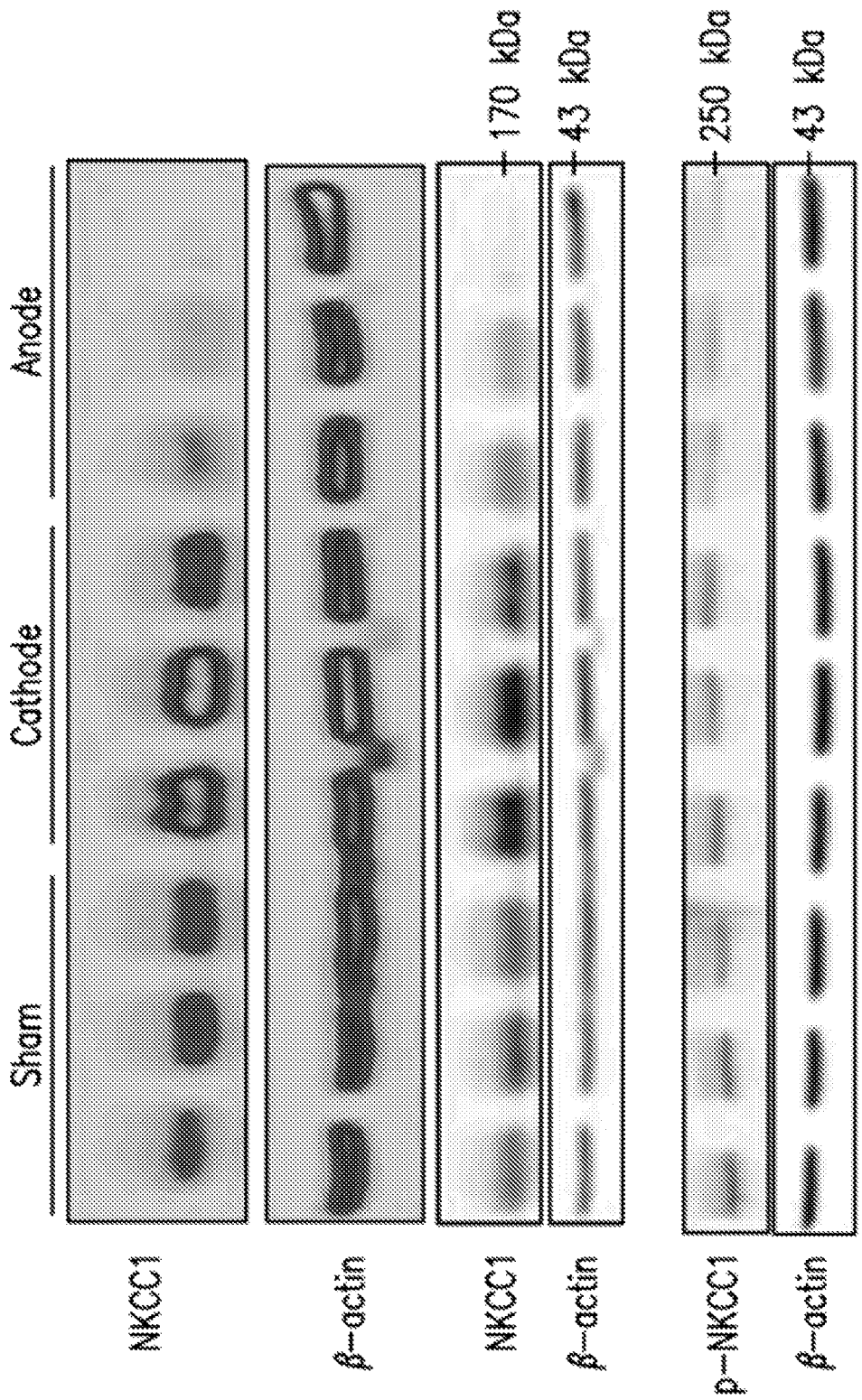
FIGS. 7A and 7B summarize the NKCC1 and p-NKCC1 expression following one stimulation session in intact mice.
Figure 7B:
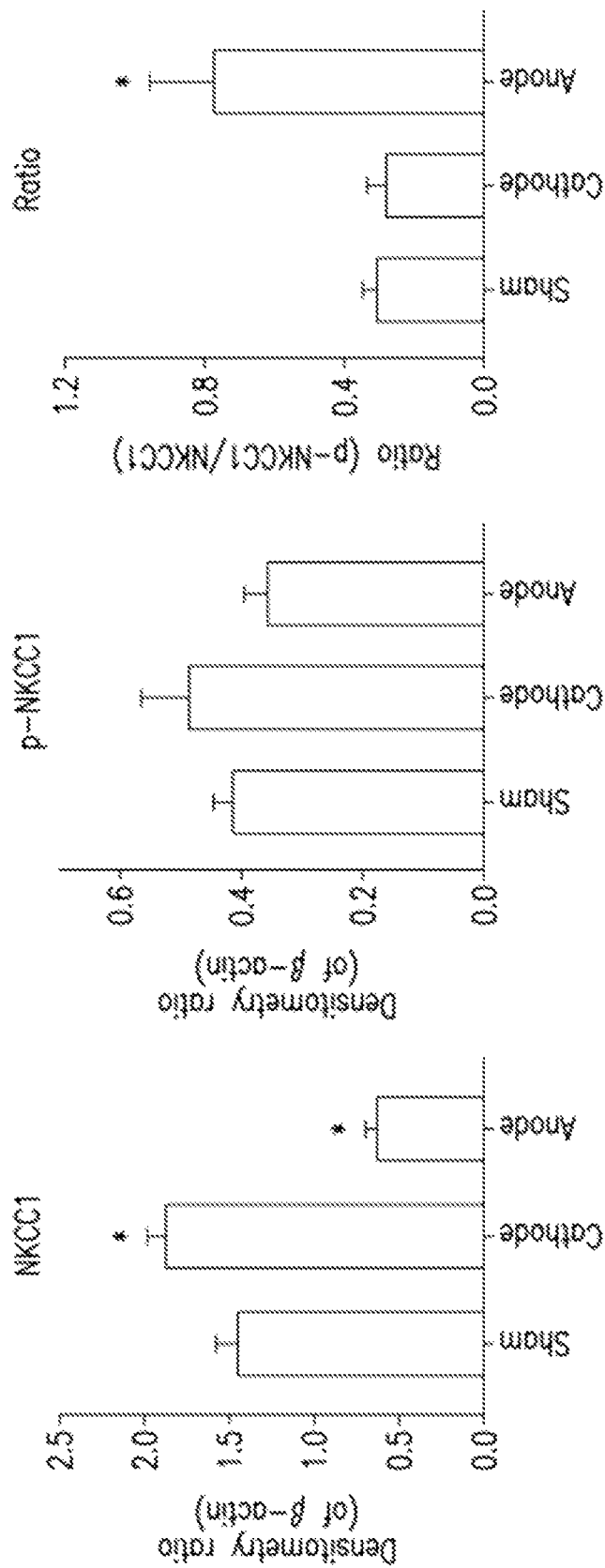
Figure 9A:
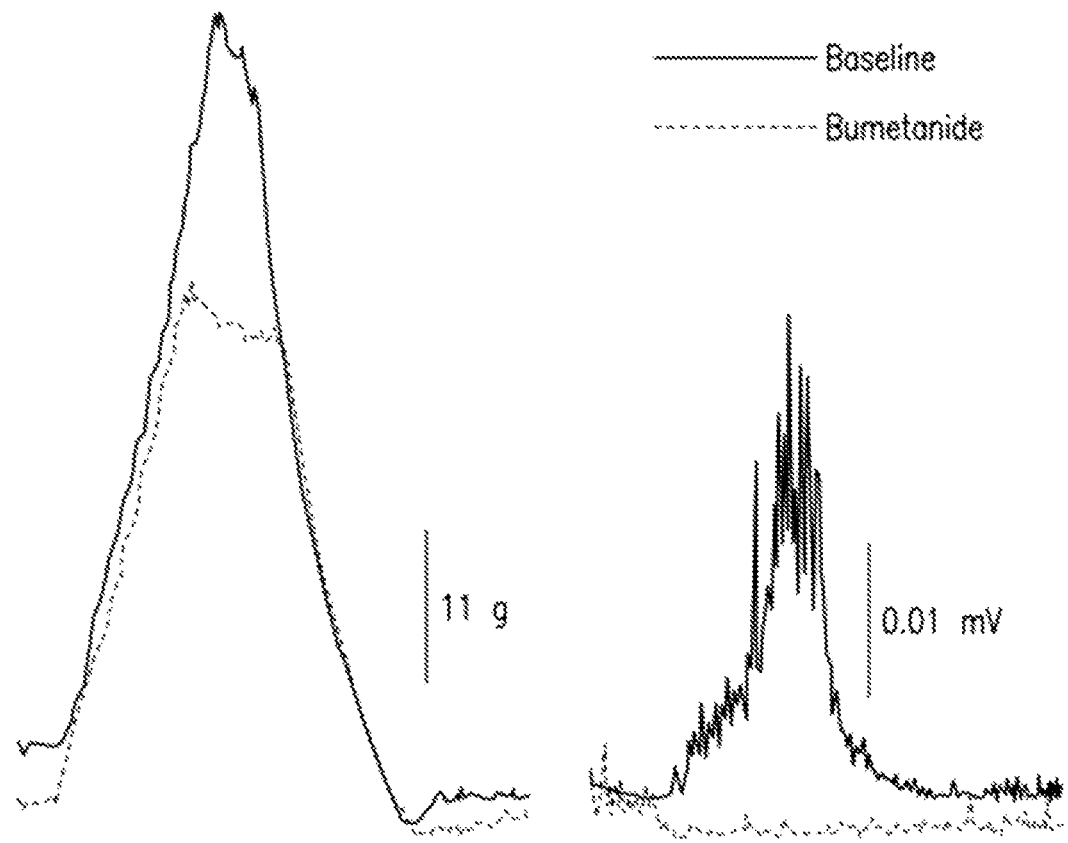
FIGS. 9A-9F summarize how the NKCC1 blocker, bumetanide, reduced spasticity in animals with SCI. Representative traces of muscle resistance (left) and concurrent EMG (right) at low speed (FIG. 9A) and high speed (FIG. 9B) are shown.
Figure 9B:
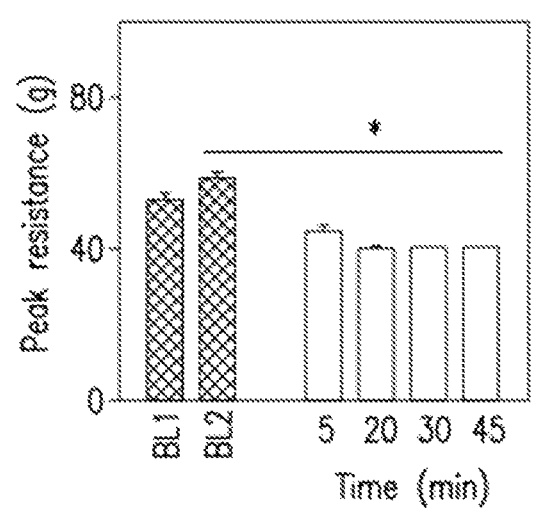
Figure 9C:
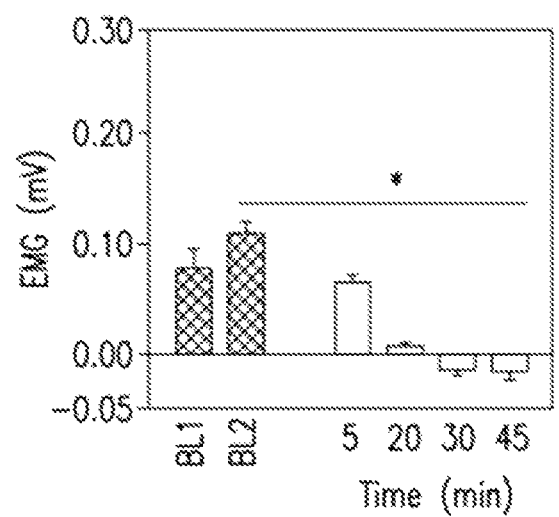
Figure 9D:
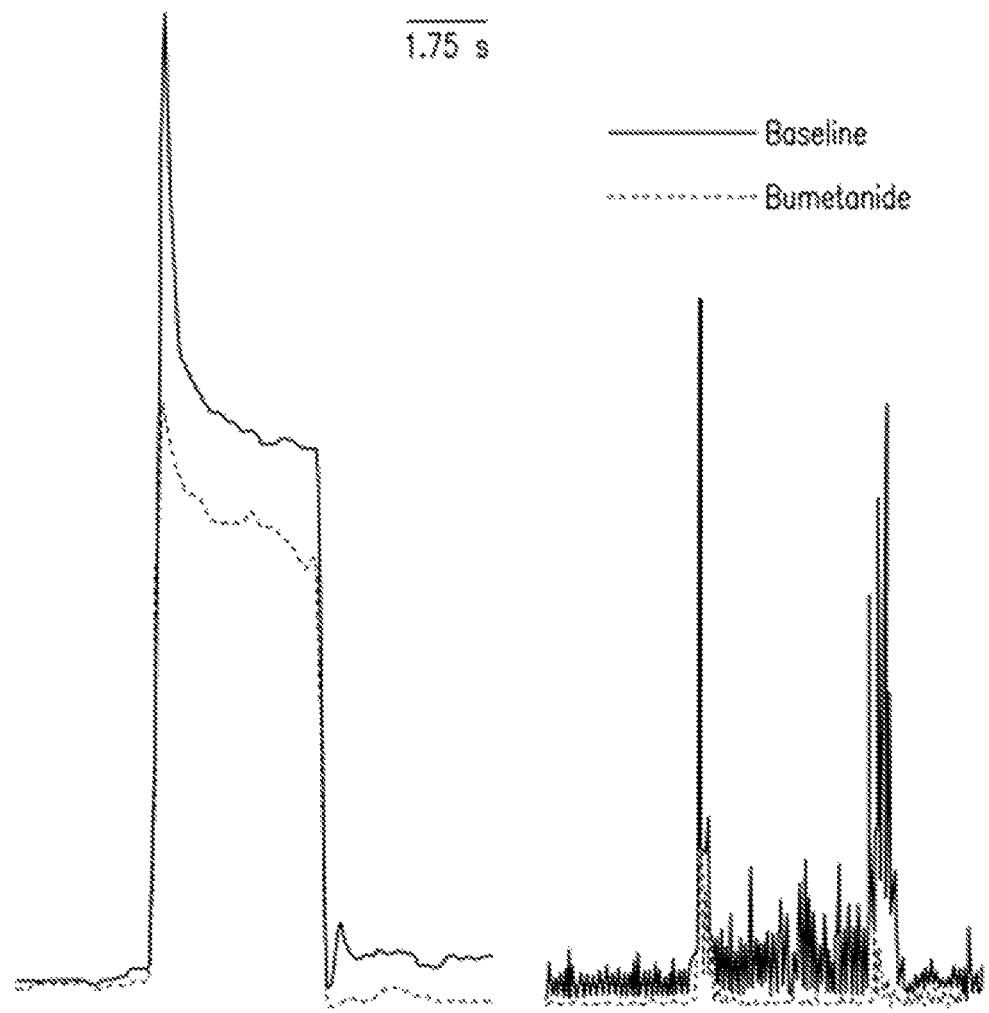
Figure 9E:
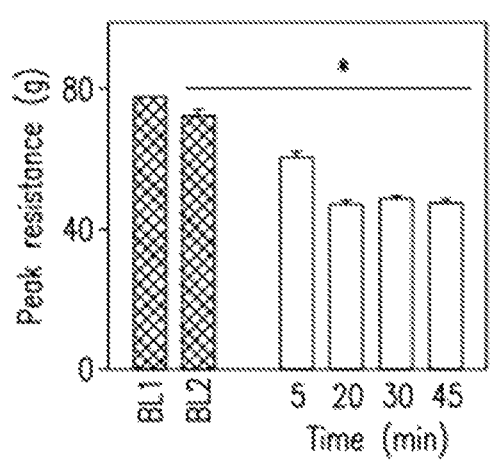
Figure 9F:
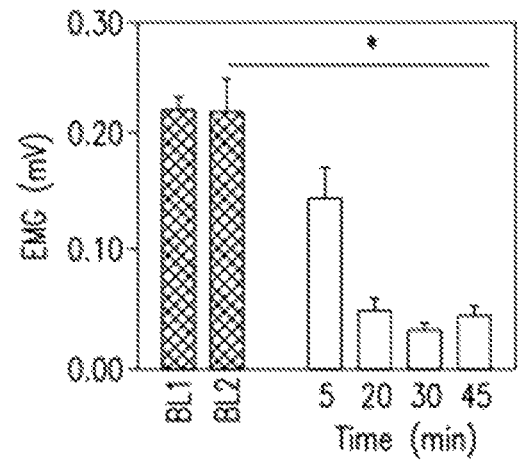

Next, levels of phosphorylated NKCC1 (p-NKCC1) were investigated. Among the groups examined, there were no differences in p-NKCC1 levels. However, when the ratio of p-NKCC1 to total NKCC1 was calculated, one-way ANOVA detected a statistically significant difference among the treatment groups (F=16.4, p<0.001), with the anodal-treated group (0.17±0.01, p<0.001), the cathodal-treated group (0.12±0.01, p<0_001), and the sham-treated group (0.14±0.01, p<0.001) exhibiting significantly lower ratios compared to the control group (0.31±0.04) (Holm-Sidak method). To establish a temporal association between stimulation and expression of NKCC1, the immediate effect of stimulation on NKCC1 expression was investigated in intact animals. Briefly, three groups of animals received either anodal, cathodal or sham tsDCS treatments and then spinal cord samples from the stimulated sites were collected 2.5 h later. The stimulation-induced changes in NKCC1 expression were similar to those observed in the animals that received repeated treatment as described above (FIG. 7). Moreover, the absolute value of p-NKCC1 was slightly increased in the cathodal-treated group, and was slightly reduced in the anodal-treated group, compared to the sham-treated group. When the ratio of p-NKCC1 to total NKCC1 was calculated, one-way ANOVA detected a statistically significant difference among the treatment groups (F=5.96, p=0.006). For example, the ratios for the anodal-treated and cathodal-treated groups were 0.77±0.18 (p=0.01) and 0.28±0.5 (p=0.8), respectively. In comparison, the ratio for the sham-treated group was 0.31±3.6 (Holm-Sidak method). Taken together, these data indicate a possible mechanism by which anodal tsDCS may cause long-term changes in spinal cord excitability.

Example 3: Detection of NKCC1 mRNA

The effect of tsDCS on mRNA levels of NKCC1 was also examined in the spinal cord tissues that were collected 2.5 h after stimulation. According to one-way ANOVA, the mean values among the treatment groups significantly differed ($F=3.8$, $p=0.03$). It was observed that anodal tsDCS did not cause a significant change in NKCC1 mRNA levels (0.85±0.37, $p=0.45$, $n=14$), while cathodal tsDCS led to a significant increase in NKCC1 mRNA levels (1.14±0.49, $p=0.03$, $n=15$), compared to the sham-treated group (0.74±0.22; $n=12$). These results are consistent with the protein expression data described above.

Example 4: Anodal tsDCS Induces an HSP70 Response

As described above, anodal tsDCS reduced expression of NKCC1 protein, yet did not affect the level of NKCCC1 mRNA. These results suggested involvement of a degradation process, and HSP70 has been shown to enhance proteasomal and lysosomal pathways of protein degradation (Reeg et al., 2016). Therefore, expression of HSP70 was investigated following anodal tsDCS in order to strengthen and explain the qPCR and Western blot data for NKCC1 levels. For these experiments, intact anesthetized animals received one session of anodal tsDCS and target tissues were collected 2 h later. A robust and significant increase in HSP70 expression was induced in the anodal-treated group compared to the sham-treated group ($p=0.03$, t-test) (FIG. 8). Immunofluorescent staining of motor neurons further demonstrated that an overall increase in HSP70 expression occurred following anodal treatment. These stainings showed localization of HSP70 in and around nuclei, in the cytoplasm, and in dendrites. In addition, staining with ChAT was performed to identify spinal motor neurons and DAPI staining identified nuclei (data not shown).

Example 5: Bumetanide, a NKCC1 Blocker, Reduced Spasticity in Animals with SCI

As described above, NKCC1 was found to be overexpressed in animals with spasticity, and levels of NKCC1 normalized after repeated anodal tsDCS. Therefore, the effect of bumetanide, a NKCC1-specific blocker, on animals with spasticity following SCI was investigated. Bumetanide was tested at two concentrations, 30 mg/kg and 60 mg/kg. One hour after bumetanide was administered at 30 mg/kg ($n=5$), moderate reductions in spasticity were observed (data not shown). Following the administration of 60 mg/kg bumetanide, peak muscle resistance and EMG were measured. One-way RM ANOVA detected significant differences among the various time points assayed (e.g., 5, 20, 30, and 45 min after the injection) ($F=83.8$, $p<0.001$). A multiple comparison test (Holm-Sidak method) also showed a significant reduction in peak resistance (34%) and corresponding EMG at a I of the time points assayed compared to the baseline measurements ($p<0.001$) (FIG. 9). Thirty min after the bumetanide injection, slow stretches were also observed to reduce background activity and resting muscle tone, while these aspects were increased in the spastic animals (FIGS. 9. A & C). Taken together, these findings establish a strong link between high levels of NKCC1 expression and spasticity. Furthermore, when non-injured control animals were injected with 60 mg/kg bumetanide, 21% of the animals exhibited a reduced reflexive stretch response. Thus, NKCC1 may have functional consequences for spinal cords in normal mice as well.

Here, the long-term effects of administering tsDCS for 20-min a day for 7 d was investigated in a mouse model of spasticity induced by SCI. Moreover, because spasticity is velocity-dependent, the triceps surae muscle was stretched at three different speeds in our mouse model. There are four parameters that are considered important when assessing spasticity: 1) peak of active resistance. 2) active slope, 3) amplitude of EMG, and 4) area of EMG. Mice treated with anodal tsDCS exhibited significant reductions in all four of these parameters compared to the other groups (FIG. 2). Ground and skill locomotion also significantly improved in the anodal tsDCS-treated animals following treatment. Furthermore, these functional improvements occurred on a similar time scale as increased RDD, increased walking parameters indicative of reduced spasticity, and reduced NKCC1 protein expression. These results, in combination with the observations that spasticity was reduced following bumetanide treatment and NKCC1 levels were reduced after one session of anodal tsDCS, suggest that NKCC1 has an important role in the ability of anodal tsDCS to reduce spasticity. Spasticity has a major impact on the effectiveness of walking and it can predict patterns of gait abnormalities (Krawetz and Nance, 1996). Spasticity also slows locomotion and interferes with skill movements due to co-contraction (Dyer et al 2011) and associative movements (Mayer. 2002). After a CNS injury, modulation of the stretch reflex, which is essential for maintaining proper progression of the gait cycle (Capaday and Stein, 1986; Crenna and Frigo, 1987), suffers varying levels of impairment depending on the extent of spasticity and the origin of injury (e.g., cerebral vs. spinal) (Faist et al., 1999).

To assess the effects of tsDCS on gait (FIG. 8), three locomotion-related parameters were investigated: rising slope, peak paw area, and falling slope. These parameters were examined based on their sensitivities to changes in the stance phase of the gait cycle. For example, the beginning of the rising slope marks the initiation of the stance phase, which is when an animal's heel strikes the ground. The remainder of the rising slope corresponds to the progressive lowering of the foot to the ground as the animal shifts its body weight (the loading response) to that foot. The shifting continues until midstance—the point at which the middle of the stance phase is achieved and the foot is flat on the ground. Midstance is also when the second parameter, peak paw area, is measured. Falling slope then follows the end of midstance, and it begins as the heel starts to elevate (heel off) and it continues as the foot gradually prepares for push off to propel the animal forward. During most of the stance phase, the TS muscles undergo progressive lengthening as the ankle flexes and the body moves forward (Lamontagne et al., 2001). In spastic animals, this lengthening triggers locomotion-interfering reflexive contractions due to impaired reflex modulation that is associated with spasticity (Faist et al., 1999). Therefore, the significant increases in the falling and rising slopes that were observed following anodal treatment (FIG. 4D, middle and lower graphs) indicate that an enhanced transition and a decreased transition time occurred. Additionally, the peak paw area for a subset of these animals increased during midstance at both of the speeds tested (FIG. 4d, top) compared to the sham-treated animals (FIG. 40, top).

Figure 4C:
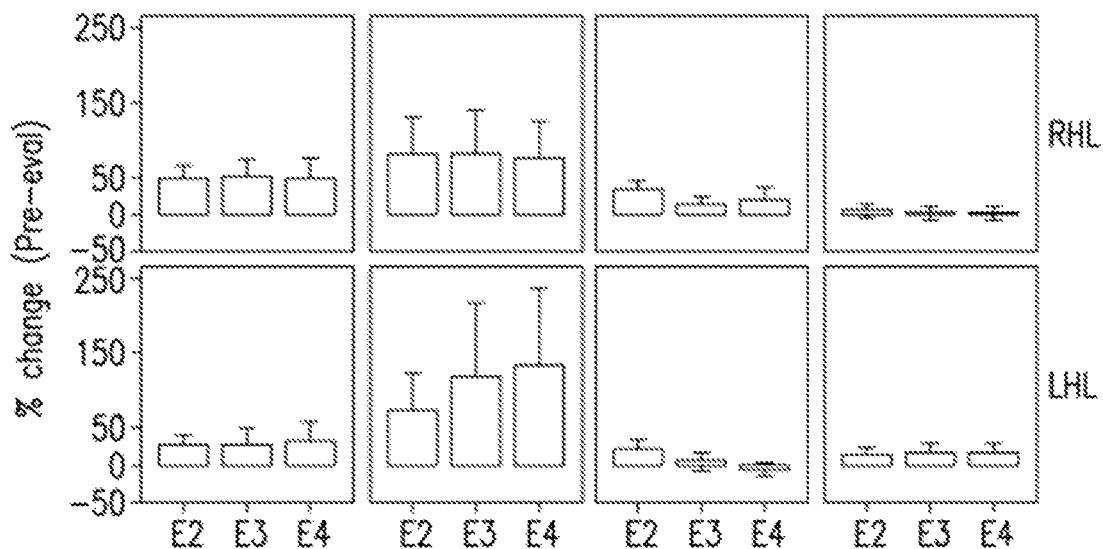
Figure 5A:
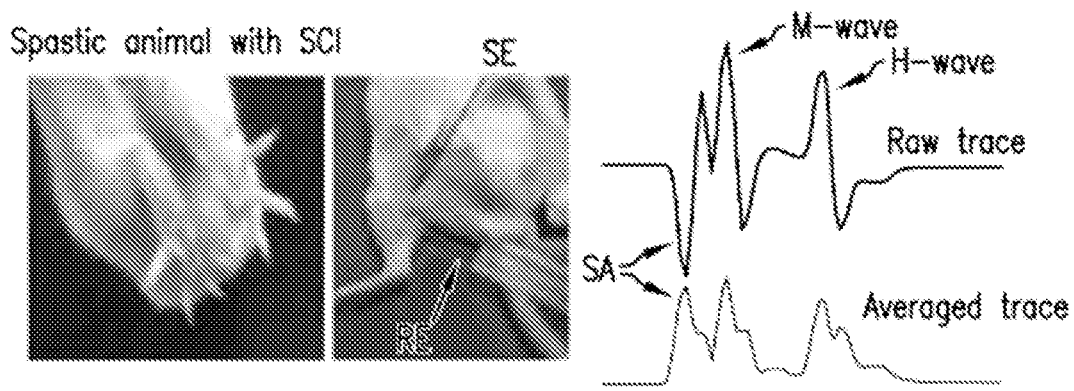
FIG. 5A-5F summarize the RDD of Hoffman reflex after repeated sessions of tsDCS stimulation. The left part of FIG. 5A shows observable characteristics of spasticity (fanning of toes) in an animal with SCI. Right: Recording setup: SE, stimulating electrode; RE, recording electrode. The two recording traces shown at the far right represent a raw trace (top) and the root-mean square calculated trace (bottom).
Figure 5B:
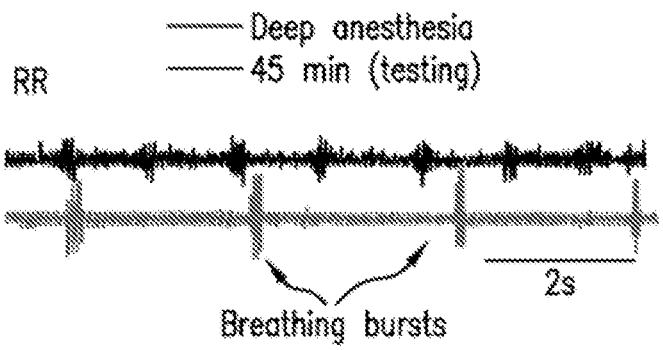
Figure 5C:
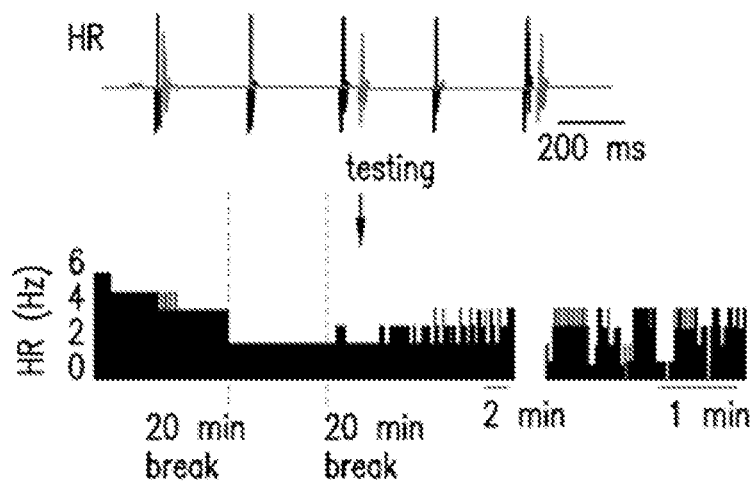
Figure 5D:
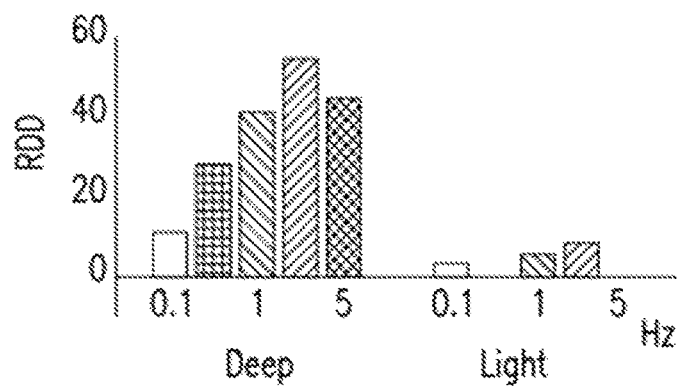
Figure 5E:
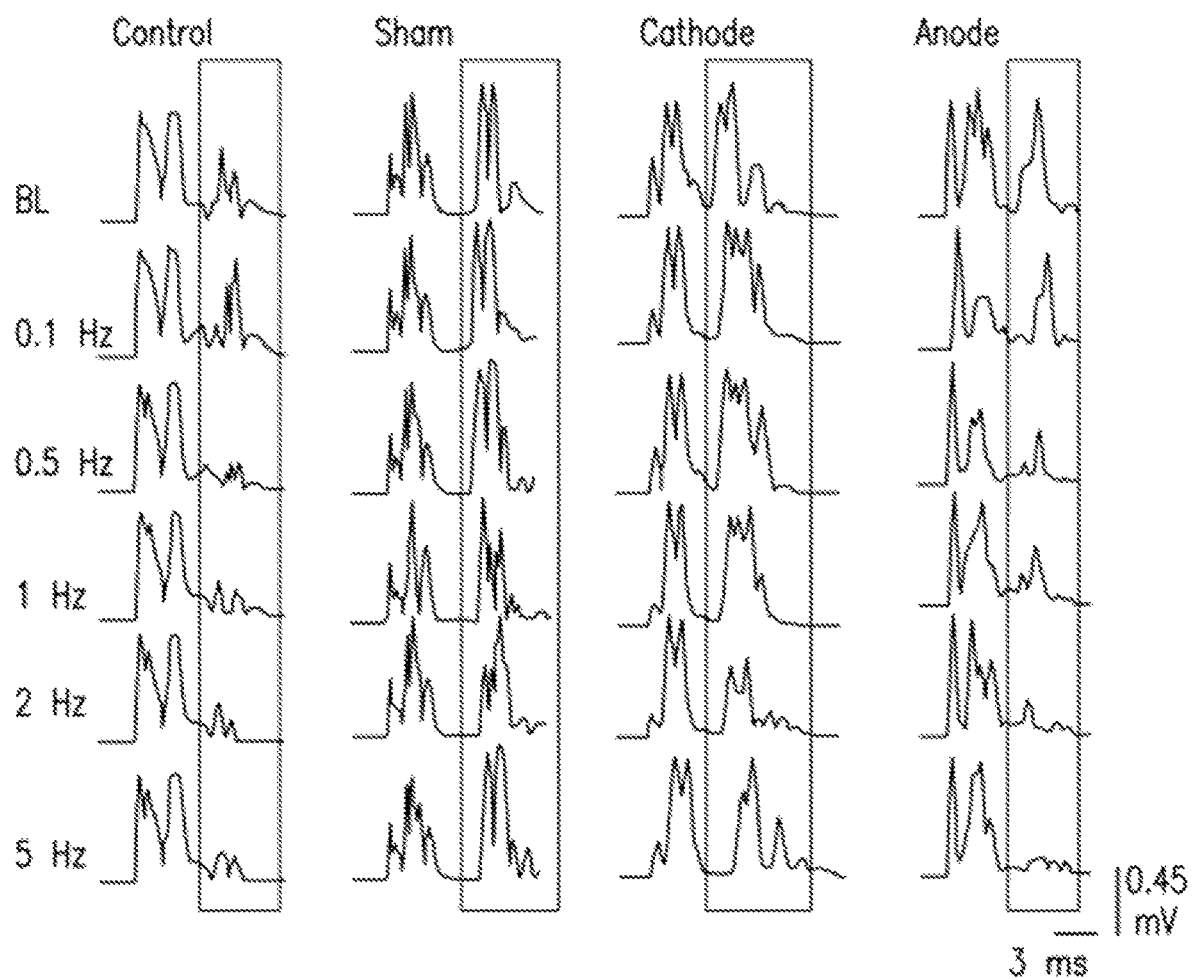
Figure 5F:
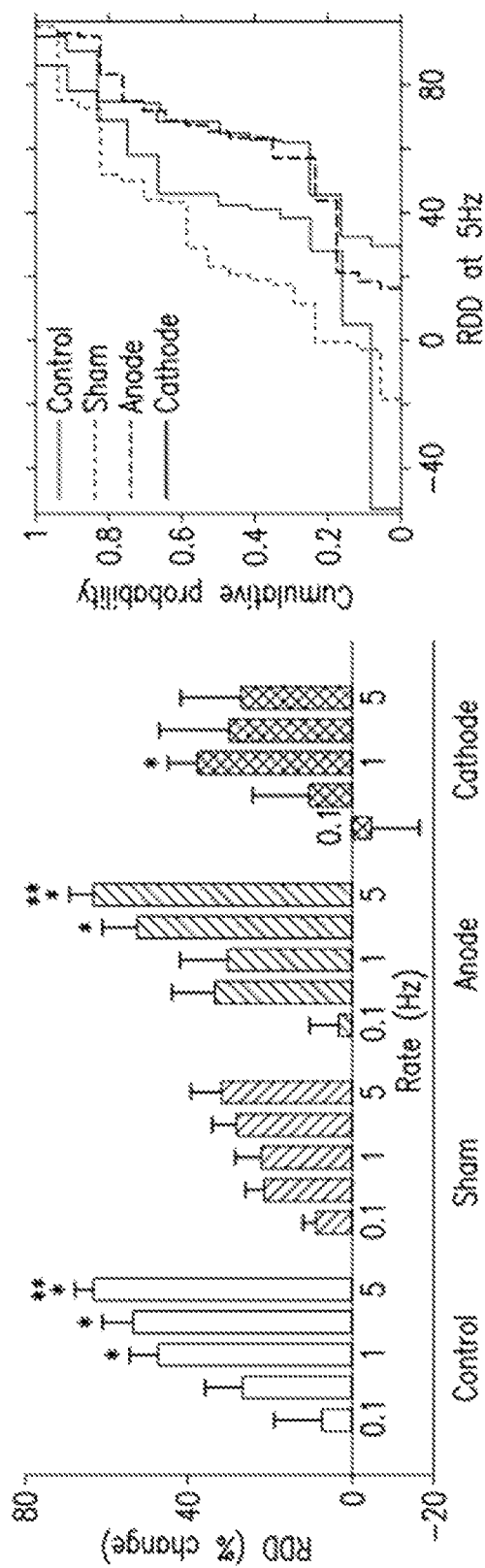

Considering that the anodal-treated animals did not receive any locomotor training, these findings reflect true behavioral recovery. Skill locomotion was tested with a ladder wheel and it was significantly improved in the animals treated with anodal tsDCS (FIG. 4). In contrast, the skill locomotion score for the intact control animals did not improve over time, thereby indicating that learning was not possible in this task. Thus the significant increases in the scores of the anodal-treated animals reflect true recovery of skill locomotion and this was training-independent. Furthermore, given that skill locomotion in mice involves the brain (Farr et al., 2006), the current results indicate that anodal tsDCS treatment may potentially uncover and/or strengthen certain corticospinal connections. RDD involves an attenuation of H-reflex amplitude following repetitive stimulations (Ishikawa et al., 1966; Lloyd and Wilson, 1957; Meinck, 1976) and it is reduced in spastic humans (Aymard et al., 2000; Nielsen et al., 1993) and animals (Hedegaard et al., 2015; Lee et al., 2014b).

It is hypothesized that the mechanisms that underlie post-activation depression involve a decrease in the probability that neurotransmitter quantal release from Ia afferent will occur due to its prior activation (Hirst et al., 1981; Kuno, 1964a; Kuno, 1964b; Lev-Tov and Pinco, 1992). In the present RDD study, there were no significant differences in RDD reduction between the different frequencies in the sham group. In contrast, there was a significant difference between the intact control and sham groups at 5 Hz (FIG. 10F), and these findings are consistent with those of a previous study (Lee et al., 2014b). Post-activation depression is functionally beneficial during voluntary movement since it lowers synaptic efficacy of Ia afferent, thereby preventing clonus and oscillations (Hultborn and Nielsen, 1998). However, decreased post-activation depression can potentially increase synapse efficacy, and this in turn could lead to hyper-excitability that is commonly associated with spasticity (Hultborn and Nielsen, 1998). Significant increases in RDD were observed in the anode group compared to the sham group following short-term tsDCS (data not shown) and long-term tsDCS (FIG. 6). The short-term effect is consistent with functional modulation of DC current at the synaptic level. When anodal DC current is applied to the dorsum of the spinal cord, it depolarizes the presynaptic terminals of Ia afferents and decreases motor neurons' excitatory postsynaptic potential (EPSP). Conversely, cathodal DC current hype repolarizes presynaptic terminals of Ia afferents and increases motor neurons' EPSP (Eccles et al., 1962). Anodal current also increases the frequency of miniature end-plate potentials due to enhanced spontaneous release (Del Castillo and Katz, 1954), which likely causes depletion of presynaptic neurotransmitters. The long-term results observed in the present study may be explained by a persistent modification of synaptic strength following anodal tsDCS, and this could be achieved with restoration of spinal inhibition by reducing expression of NKCC1. Following SCI, expression levels of KCC2 and NKCC1 have been found to be altered (Cramer et al., 2008; Hasbargen et al., 2010; Lee et al., 2014a). Furthermore, an imbalance between these cotransporters can lead to spinal hyperexcitability, and hence, spasticity, spasms, and/or pain (D'Amico et al., 2014; Hasbargen et al., 2010). In rats, SCI causes down regulation of KCC2, and this has been shown to correlate with spasticity (Boulenguez e: al., 2010).

In the present study, an insignificant reduction in the expression of KCC2 or p-KCC2 was observed in the sham-treated injured animals. Since this result is inconsistent with previously published data (Boulenguez et al., 2010), Western blots were performed twice with all of the samples. In general, our KCC2 results are in agreement with previously reported results (Modal et al., 2014). It should also be noted that an anti-phospho-serine 940 KCC2 antibody was used in the present study. Phosphorylation at this site is mediated by protein kinase C (PKC) and it enhances the stability of KCC2 at the cell surface and increases ion transport (Lee et al., 2007). Meanwhile, expression of NKCC1 was markedly elevated in our SCI animals without a significant change in the absolute level of p-NKCC1. These results indicate that in CD-1 mice, an elevated level of NKCC1 expression is probably a crucial factor in modulating spinal excitability following SCI. This conclusion is supported by the observation that spasticity was reduced following treatment with the NKCC1-specific blocker, bumetanide (FIG. 8). Repeated anodal tsDCS resulted in a significant reduction in spasticity parameters in CD-1 mice with SCI (FIG. 2) and a permanent reduction in the level of NKCC1 (FIG. 6B). Conversely, the mice that received the opposite polarity exhibited slight worsening in spasticity and skill locomotion and a permanent increase in the level of NKCC1 compared to sham-treated animals. To demonstrate a contemporaneous effect of tsDCS on NKCC1 expression, short-term experiments were performed 2.5 h after a single session of stimulation was applied to anesthetized control animals. A robust polarity-dependent effect of tsDCS was observed (FIG. 7), and neither injury nor wakefulness was critical to this effect. Furthermore, a significant reduction in the level of NKCC1 was detected after anodal stimulation, and this was not accompanied by any significant change in the level of NKCC1 mRNA. These results suggest that a mechanism involving protein degradation should be considered, and this may be a $Ca+^2$-dependent process (Reynolds et al., 2007). Moreover, in our previous study, $Ca+^2$ accumulation was found to significantly increase in nervous tissue following anodal stimulation (Wieraszko and Ahmed, 2016), and this may be due to increased glutamate release in spinal cord tissue (Ahmed and Wieraszko, 2012). In the present study, no evidence of a direct link between calcium accumulation and NKCC1 degradation was observed, although the simultaneous occurrence of the two events following anodal stimulation suggests a strong association. Previously, calcium-dependent degradation of NKCC1 was observed (Reynolds et al., 2007), as well as a degradation of proteins following glutamate treat-rent (Guo and Wang, 2007). To strengthen this association, HSP70, a protein which is known to enhance the flow of substrates through proteasomal or lysosomal pathways for degradation was investigated. In the present study, anodal tsDCS was found to induce a significant HSP70 response (FIG. 9). Thus, the observations that anodal tsDCS increases glutamate release, increases calcium accumulation, induces an HSP70 response, and down-regulates NKCC1 protein, yet not its mRNA, strongly suggest that anodal tsDCS-induces protein degradation processes.

Figure 10:
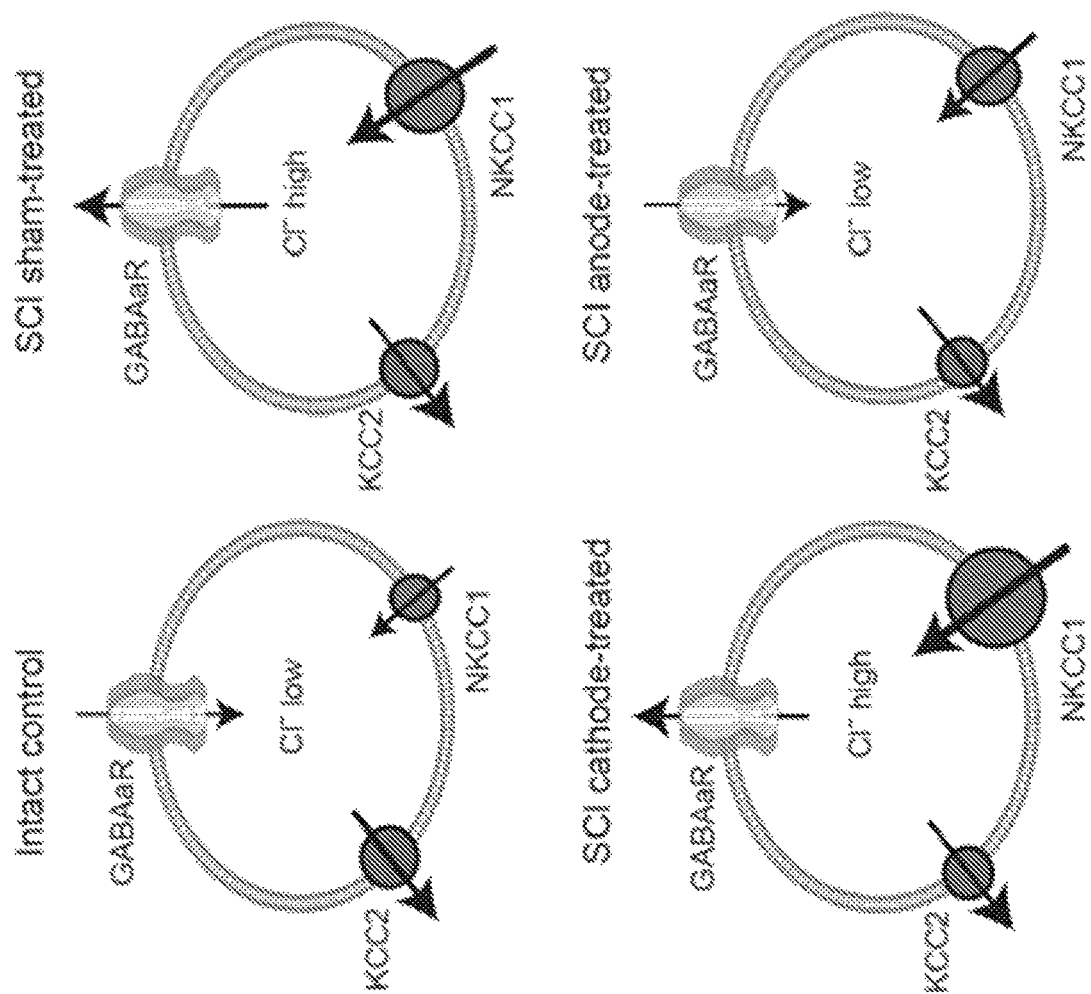
FIG. 10 comprises an illustration showing tsDCS-mediated changes in protein expression for KCC2 and NKCC1 in the experimental models tested in the current study and in relation to intracellular chloride concentration. In the healthy controls, the level of NKCC1 was lower than the level of KCC2, thereby leading to a lower intracellular concentration of Cl. However, in spastic animals with a SCI that were in the sham- and cathodal-treated groups, NKCC1 was found to be upregulated, thereby leading to an increase in intracellular CI and disinhibition. In contrast, anodal tsDCS-treated animals had lower levels of NKCC1 and inhibition was restored.
Figure 11:
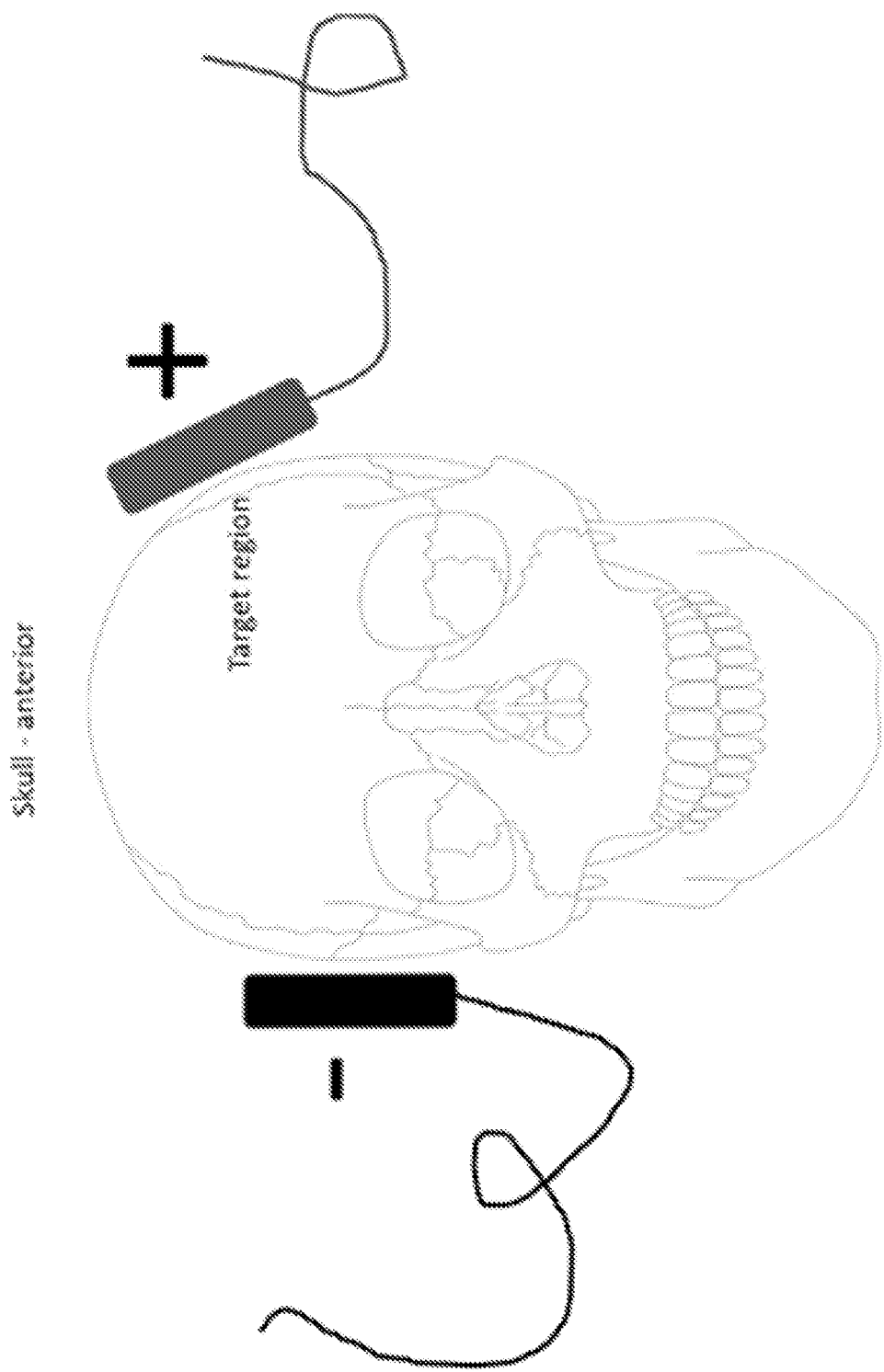
FIG. 11 is an illustration of a representative example of anodal trans-cranial direct current stimulation of a target region. The exact location of the anode and cathode depends on the type of disease being treated and the cranial region being targeted.

However, further studies are needed to investigate the details of the signal transduction mechanisms potentially involved in mediating the actions of anodal tsDCS. Meanwhile, the observations that cathodal tsDCS increased levels of NKCC1 protein and mRNA indicate that cathodal tsDCS mediates a distinct mechanism involving de novo protein synthesis. P-NKCC1 is a dimer of the mature form of NKCC1 that has a molecular weight of ~250 kDa. Since this form is distinct from NKCC1 based on molecular weight (MW, 135/170 kDa), p-NKCC1 is not part of NKCC1. Currently, the role of phosphorylation in relation to the activity of NKCC1 in nervous tissue remains unknown. It has been demonstrated that up-regulation of NKCC1 in brain tissue contributes to ischemic damage in the absence of elevated NKCC1 activity by phosphorylation (Yan al., 2003), thereby indicating that NKCC1 is an active form. Correspondingly, the upregulation of NKCC1 that was detected in the current study may be implicated in spinal disinhibition. Moreover, the absolute level of p-NKCC1 remained unchanged between the groups examined, and a 34% reduction in reflexive muscle resistance was observed in the animals with SCI versus a 21°/0 reduction in controls after bumetanide injection. These results support the hypothesis that NKCC1 is active in the absence of phosphorylation. In another study, phosphorylation of NKCC1 by P KC (a serine-threonine kinase) was found to induce the internalization of NKCC1, and this was accompanied by a loss of NKCC1 units from the basolateral membrane (Tang et al., 201C). Thus, the relative increase in p-NKCC1 that was observed in the anode group in the present study may be related to its degradation. FIG. 10 illustrates a potential mechanism of action mediating the effect of tsDCS on spinal excitability, and a possible role for p-NKCC1 I included.

In summary, the present results demonstrate that anodal tsDCS can cause a permanent reduction in spasticity in CD-1 mice with SCI. In addition, ground and skill locomotion were improved without additional training, while increased expression of NKCC1 was associated with spasticity. A specific role for NKCC1 was further demonstrated with pharmacological inhibition of NKCC1, and with down-regulation of NKCC1 by anodal tsDCS, both of which led to reduced spasticity. Taken together, the results of the present study provide strong evidence that downregulation of NKCC1 expression has an important role in mediating the action of anodal tsDCS.

The invention claimed is:

1. A system for treatment of at least one of spasticity, hypertonia, dystonia, ALS and neuronal hyperexcitability in a vertebrate being, the system comprising:
   a first stimulation component configured to provide peripheral direct current stimulation of a peripheral nerve or nerves associated with at least one of spasticity, hypertonia, dystonia, ALS and neuronal hyperexcitability in a vertebrate being; said first stimulation component including a neural stimulation circuit having at least one neural stimulation pole configured to stimulate at least one said peripheral nerve;
   a second stimulation component configured to provide spinal direct current stimulation at a spinal location associated with treatment of said at least one said peripheral nerve, said second stimulation component defining a spinal stimulation circuit having an active spinal stimulation pole and a spinal reference pole, said spinal stimulation circuit configured to provide trans-spinal direct current stimulation between said active spinal stimulation pole and said spinal reference pole for stimulating said spinal location; the active spinal stimulation pole being relatively proximal to said spinal location; the spinal reference pole being relatively distal to said spinal location; and
   a controller component configured to ensure that said active spinal stimulation pole and said at least one neural stimulation pole are excited at opposite polarities, and forming a resulting polarization circuit, said resulting polarization circuit being configured to provide a polarizing current flow between said active spinal stimulation pole and said proximal neural pole according to said opposite polarities, for changing biological activity of and/or level of gene expression of and/or protein expression of a target molecule according to said polarizing current flow; said controller component being further configured to provide said polarizing current flow for a predetermined time period to change said at least one of said biological activity, said gene expression, and said protein expression and to achieve at least one of cell proliferation, cell differentiation, cell migration, and cell expression, associated with a treatment delivered for at least one of the neurological conditions including spasticity, hypertonia, dystonia, ALS and neuronal hyperexcitability in said vertebrate being; wherein said target molecule is NKCC1 and wherein the change in said at least one of said biological activity, said gene expression, and said protein expression is one of increased and decreased.

2. The system of claim 1, wherein said controller component is configured to provide said polarizing current flow including at least one of constant, continuous, pulsed, intermittent, varying and non-varying current flow.

3. The system of claim 1, wherein said controller component is further configured to simultaneously control a range of current supplied by the first and second stimulation components.

4. The system of claim 1, wherein at least one of the controller component and an electrical source are disposed in a wearable housing.

5. The system of claim 1, wherein said controller component is further configured to repeat said direct current stimulation a predetermined number of times over a predetermined number of days, wherein said predetermined number of times and said predetermined number of days are selected to change biological activity of or level of gene expression and/or protein expression of NKCC1.

6. The system of claim 1, wherein the controller component is configured to provide direct current flow for stimulation of said current path across at least one of a spinal cord, a cranium and the peripheral nerve of the vertebrate being.

7. The system of claim 1, further configured having:
   a plurality of A stimulation components configured to provide at least one of i) peripheral direct current stimulation of said peripheral nerve at a plurality of locations along the peripheral nerve, and ii) peripheral direct current stimulation of a plurality of peripheral nerves of said being; each of said a stimulation components including a neural stimulation circuit having neural stimulation poles configured to stimulate said peripheral nerve or plurality of peripheral nerves; and
   a plurality of B stimulation components configured to provide spinal direct current stimulation at a plurality of spinal locations associated with regulation of said peripheral nerve or plurality of peripheral nerves, each of said B stimulation components defining a respective spinal stimulation circuit having a respective active spinal stimulation pole and a respective spinal reference pole, said respective spinal stimulation circuit configured to provide trans-spinal direct current stimulation between said respective active spinal stimulation pole and said respective spinal reference pole for stimulating a respective one of said plurality of spinal locations.

8. The system of claim 7, further configured as a stimulation device, comprising:
   a direct current voltage source having a plurality of terminals including;
   a plurality of A terminals for connecting a plurality of A electrodes to the direct current voltage source; the plurality of A electrodes being configured for affixation at any of a plurality of locations including i) at a dorsal aspect of a spinal cord of a vertebrate being and ii) at a plurality of locations on a cranium of said vertebrate being;

a plurality of B terminals for connecting a plurality of B electrodes to the direct current voltage source; the plurality of B electrodes being configured for affixation at a plurality of positions remote from said plurality of A electrodes; respective ones of said A and B electrodes being oppositely charged; and said controller component being configured to control current flow between said respective ones of oppositely charged electrodes; said controller component being configured to provide direct current stimulation at least one of for a predetermined time period and fora predetermined number of times for said treatment delivered.

* * * * *